United States Patent
Lee et al.

(10) Patent No.: US 11,678,577 B2
(45) Date of Patent: Jun. 13, 2023

(54) ORGANIC ELECTRONIC ELEMENT COMPRISING COMPOUND FOR ORGANIC ELECTRONIC ELEMENT AND AN ELECTRONIC DEVICE THEREOF

(71) Applicant: DUK SAN NEOLUX CO., LTD., Cheonan-si (KR)

(72) Inventors: Yun Suk Lee, Cheonan-si (KR); Nam Geol Lee, Cheonan-si (KR); Jae Wan Jang, Cheonan-si (KR); Jae Duk Yoo, Cheonan-si (KR); Soung Yun Mun, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 128 days.

(21) Appl. No.: 17/212,886

(22) Filed: Mar. 25, 2021

(65) Prior Publication Data

US 2022/0131090 A1 Apr. 28, 2022

Related U.S. Application Data

(63) Continuation of application No. 17/096,790, filed on Nov. 12, 2020, now Pat. No. 11,063,226.

(30) Foreign Application Priority Data

Oct. 26, 2020 (KR) .................. 10-2020-0139441

(51) Int. Cl.
*H01L 51/00* (2006.01)
*H01L 51/50* (2006.01)
(Continued)

(52) U.S. Cl.
CPC ....... *H10K 85/6574* (2023.02); *C07D 251/24* (2013.01); *C09K 11/06* (2013.01); *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02); *H10K 50/15* (2023.02); *H10K 50/16* (2023.02);
(Continued)

(58) Field of Classification Search
None
See application file for complete search history.

(56) References Cited

U.S. PATENT DOCUMENTS

| 2014/0367654 | A1* | 12/2014 | Kim | ............... H01L 51/0052 257/40 |
| 2015/0303379 | A1* | 10/2015 | Lee | ............... C07D 405/04 548/440 |
| 2016/0133674 | A1* | 5/2016 | Lee | ............... H01L 27/3244 257/40 |

FOREIGN PATENT DOCUMENTS

| KR | 10-2009-0079134 A | 7/2009 |
| KR | 10-2016-0111780 A | 9/2016 |
| WO | 2017/171420 A1 | 10/2017 |

\* cited by examiner

*Primary Examiner* — Vu A Nguyen
(74) *Attorney, Agent, or Firm* — Vorys, Sater, Seymour and Pease LLP; Mih Suhn Koh

(57) ABSTRACT

Provided are an organic electronic element including an anode, a cathode, and an organic material layer between the anode and the cathode, and an electronic device including the organic electronic element, wherein the organic material layer includes each of the compounds represented by Formulas 1 and 2 and the driving voltage of the organic electronic element is lowered, and the luminous efficiency and lifetime of the element are improved.

4 Claims, 3 Drawing Sheets

(51) Int. Cl.
  *C09K 11/06* (2006.01)
  *C07D 251/24* (2006.01)
(52) U.S. Cl.
  CPC ......... *H10K 50/18* (2023.02); *H10K 2101/10* (2023.02); *H10K 2101/90* (2023.02)

ORGANIC ELECTRONIC ELEMENT COMPRISING COMPOUND FOR ORGANIC ELECTRONIC ELEMENT AND AN ELECTRONIC DEVICE THEREOF

TECHNICAL FIELD

The present invention relates to compound for organic electronic element, organic electronic element using the same, and an electronic device thereof.

BACKGROUND ART

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the organic light emitting diode, the most problematic is the lifetime and the efficiency. As the display becomes large, the efficiency and the lifetime problem must be solved. Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in a hole transport layer, an emitting-auxiliary layer must be present between the hole transport layer and an emitting layer, and it is necessary to develop different emitting-auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic device are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against joule heating generated when the device is driven, while delaying penetration of the metal oxide from the anode electrode (ITO), which is one of the causes of shortening the lifetime of the organic electronic device, into the organic layer. The low glass transition temperature of the hole transport layer material has a characteristic that when the device is driven, the uniformity of the surface of the thin film is lowered, which has been reported to have a great influence on the lifetime of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, development of new materials is continuously required, and development of materials for the hole transport layer or the emitting-auxiliary layer is urgently required.

SUMMARY OF INVENTION

Problems to be Solved by the Invention

An object of the present invention is to provide an organic electronic element including a compound capable of lowering a driving voltage of an element and improving luminous efficiency, color purity, stability, and lifetime of the element, and an electronic element thereof.

The present invention provides an organic electronic element comprising a first electrode, a second electrode, and an organic material layer formed between the first electrode and the second electrode, wherein the organic material layer comprises an emitting layer, wherein the emitting layer is a phosphorescent emitting layer and comprises a first host compound represented by Formula 1 and a second host compound represented by Formula 2.

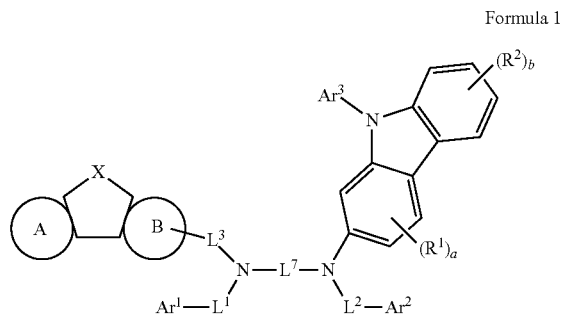

Formula 1

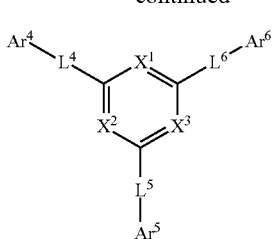

Formula 2

In another aspect, the present invention provides an electronic device including the organic electronic element.

Effects of the Invention

By using the compound according to the present invention, it is possible to achieve a high luminous efficiency, a low driving voltage, and a high heat resistance of the element, and can greatly improve the color purity and lifetime of the element.

DETAILED DESCRIPTION OF THE INVENTION

Figure 1:
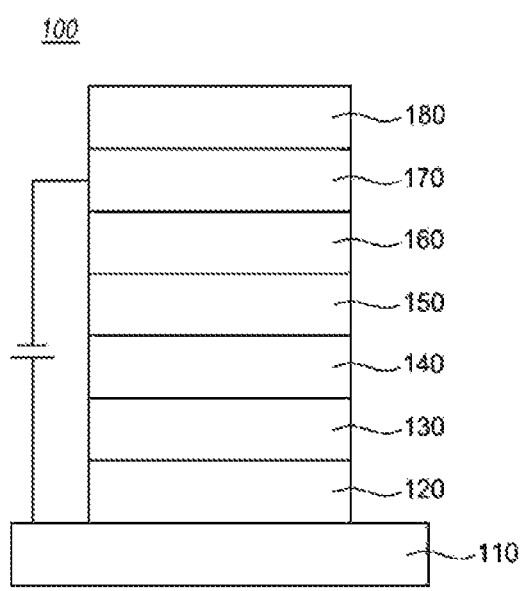
FIG. 1 to FIG. 3 are each an exemplary view of an organic electronic element according to one aspect of the present invention.

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected," "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxycarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

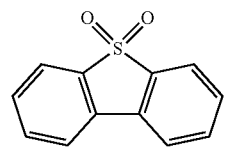 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a Spiro compound together with the carbon to which they are bonded.

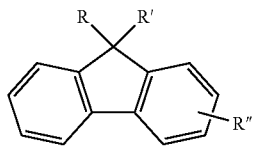

The term "spiro compound", as used herein, has a 'Spiro union', and a Spiro union means a connection in which two rings share only one atom. At this time, atoms shared in the two rings are called 'spiro atoms', and these compounds are called 'monospiro-', 'di-spiro-' and 'tri-spiro-', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

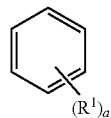

here, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

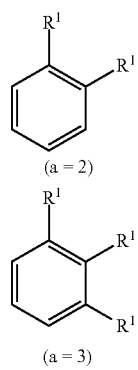

Hereinafter, a laminated structure of an organic electronic device including the compound of the present invention will be described with reference to FIGS. 1 to 3.

In adding reference numerals to elements of each figure, it should be noted that the same elements have the same numerals as possible even if they are indicated on different figures.

In addition, in describing the present invention, when it is determined that a detailed description of a related known configuration or function may obscure the subject matter of the present invention, a detailed description thereof will be omitted.

Figure 2:
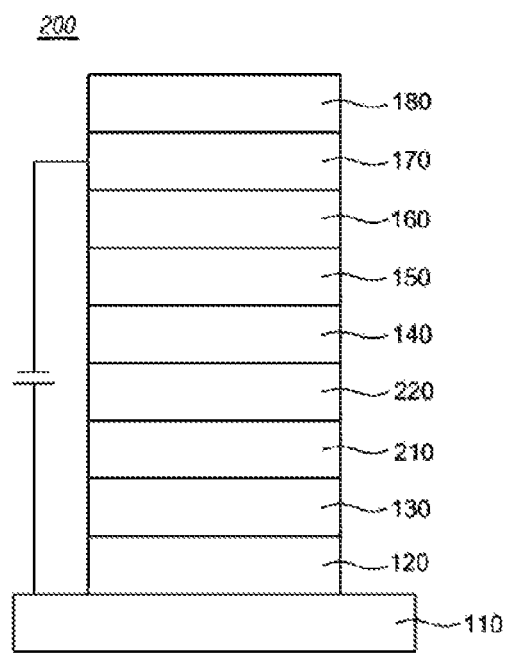
Figure 3:
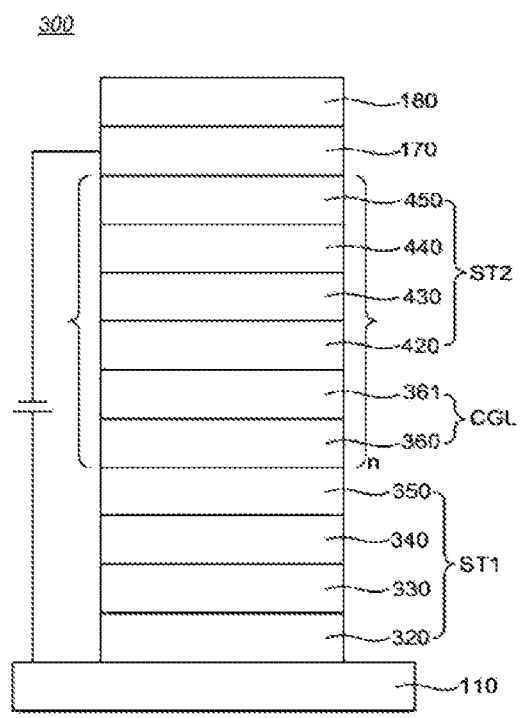

FIG. 1 to FIG. 3 illustrate an example of an organic electronic element according to an embodiment of the present invention.

Referring to FIG. 1, an organic electronic element (100) according to an embodiment of the present invention includes a first electrode (110), a second electrode (170) formed on a substrate (not shown) and an organic material layer formed between the first electrode (110) and the second electrode (170).

The first electrode (110) may be an anode, the second electrode (170) may be a cathode, and in the case of an inverted type, the first electrode may be a cathode and the second electrode may be an anode.

The organic material layer may include a hole injection layer (120), a hole transport layer (130), an emitting layer (140), an electron transport layer (150), and an electron injection layer (160). Specifically, a hole injection layer (120), a hole transport layer (130), an emitting layer (140), an electron transport layer (150), and an electron injection layer (160) may be sequentially formed on the first electrode (110).

The present invention may further include a light efficiency enhancing layer formed on one of not in contact with the organic material layer among one side of the first electrode (110) or of the second electrode (170), and when the light efficiency enhancing layer (180) is formed, the light efficiency of the organic electronic element may be improved.

For example, the light efficiency enhancing layer (180) may be formed on the second electrode (170), and in the case of a top emission organic light emitting device, the light efficiency enhancing layer (180) is formed, thereby reducing optical energy loss due to surface plasmon polaritons (SPPs) in the second electrode (170), and in the case of a bottom emission organic light emitting device, the light efficiency enhancing layer (180) may function as a buffer for the second electrode (170).

A buffer layer (210) or an emitting auxiliary layer (220) may be further formed between the hole transport layer (130) and the emitting layer (140), which will be described with reference to FIG. 2.

Referring to FIG. 2, an organic electric device (200) according to another embodiment of the present invention includes a hole injection layer (120), a hole transport layer (130), a buffer layer (210), an emitting auxiliary layer (220), an emitting layer (140), an electron transport layer (150), an electron injection layer (160), a second electrode (170), sequentially formed on the first electrode (110), and a light efficiency enhancing layer (180) formed on the second electrode.

Although not shown in FIG. 2, an electron transport auxiliary layer may be further formed between the emitting layer (140) and the electron transport layer (150).

Also, according to another embodiment of the present invention, the organic material layer may have a plurality of stacks including a hole transport layer, an emitting layer, and an electron transport layer. This will be described with reference to FIG. 3.

Referring to FIG. 3, in the organic electronic element (300) according to another embodiment of the present invention, 2 or more sets of stacks (ST1 and ST2) made of a multi-layered organic material layer may be formed between the first electrode (110) and the second electrode (170), and a charge generation layer (CGL) may be formed between the stacks of organic material layers.

Specifically, the organic electronic element according to an embodiment of the present invention includes a first electrode (110), a first stack (ST1), a charge generation layer (CGL), a second stack (ST2), and a second electrode. (170) and a light efficiency enhancing layer (180) may be included.

The first stack (ST1) is an organic material layer formed on the first electrode (110) and may include a first hole injection layer (320), a first hole transport layer (330), a first emitting layer (340), and a first electron transport layer (350), and the second stack (ST2) may include a second hole injection layer (420), a second hole transport layer (430), a second emitting layer (440), and a second electron transport layer (450). As described above, the first stack and the second stack may be organic material layers having the same laminated structure, but may be organic material layers having different laminated structures.

A charge generation layer (CGL) may be formed between the first stack (ST1) and the second stack (ST2). The charge generation layer (CGL) may include a first charge generation layer (360) and a second charge generation layer (361). The charge generation layer (CGL) is formed between the first emitting layer (340) and the second emitting layer (440) to increase the current efficiency generated in each emitting layer and smoothly distribute charge.

When a plurality of emitting layers are formed by the multilayer stack structure method as shown in FIG. 3, an organic electronic element that emits white light by a mixing effect of light emitted from each emitting layer can be manufactured, as well as an organic electronic element that emits light of various colors.

The compounds represented by Formulas 1 and 2 of the present invention may be used as a material for a hole injection layer (120, 320, 420), a hole transport layer (130, 330, 430), a buffer layer (210), an emitting auxiliary layer (220), and an electron transport layer (150, 350, 450), the electron injection layer (160), the emitting layer (140, 340, 440), or the light efficiency enhancing layer (180), but preferably, the compounds represented by Formulas 1 and 2 of the present invention may be used as a host of the emitting layers (140, 340, 440).

Otherwise, even if the same or similar core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electronic element according to an embodiment of the present invention may be manufactured using various deposition methods. It can be manufactured using a vapor deposition method such as PVD or CVD. For example, an anode (110) is formed by depositing a metal or a conductive metal oxide or an alloy thereof on a substrate, and after forming an organic material layer including the hole injection layer (120), the hole transport layer (130), the emitting layer (140), the electron transport layer (150) and the electron injection layer (160) thereon, the organic electroluminescent device according to an embodiment of the present invention can be manufactured by depositing a material that can be used as a cathode (170) thereon. Also, an emitting auxiliary layer (220) may be further formed between the hole transport layer (130) and the emitting layer (140), and an electron transport auxiliary layer (not shown) may be further formed between the emitting layer (140) and the electron transport layer (150), and as described above, may be formed in a stack structure.

Also, the organic material layer may be manufactured with a smaller number of layers by using various polymer materials and not by a deposition method, but by a solution process, a solvent process, such as a spin coating process, a nozzle printing process, an inkjet printing process, a slot coating process, a dip coating process or a roll-to-roll process, doctor blading process, screen printing process, or a thermal transfer method. Since the organic material layer according to the present invention can be formed by various methods, the scope of the present invention is not limited by the forming method.

In addition, the organic electric device according to an embodiment of the present invention may be selected from the group consisting of an organic electroluminescent device, an organic solar cell, an organic photoreceptor, an organic transistor, a monochromatic lighting device, and a quantum dot display device.

Another embodiment of the present invention may include an electronic device comprising a display device including the organic electronic element; and a control unit for driving the display device. At this time, the electronic device may be a current or future wired/wireless communication terminal, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electronic element according to an aspect of the present invention will be described.

The present invention provides an organic electronic element comprising a first electrode, a second electrode, and an organic material layer formed between the first electrode and the second electrode, wherein the organic material layer comprises an emitting layer, wherein the emitting layer comprises a first host compound represented by Formula 1 and a second host compound represented by Formula 2 as the phosphorescent emitting layer.

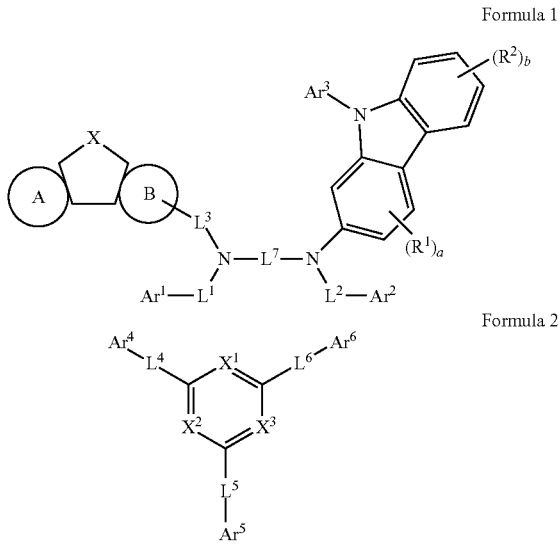

Formula 1

Formula 2

In Formulas 1 and 2, each symbol may be defined as follows.

1) A ring and B ring are each independently a $C_6$-$C_{20}$ aryl group; or a $C_2$-$C_{60}$ heterocyclic group; provided that at least one of the A ring and B ring is a $C_{10}$-$C_{20}$ aryl group, $R^3$ can be substituted in ring A, and $R^4$ can be substituted in ring B.

2) $X^1$, $X^2$ and $X^3$ are each independently CR or N, provided that at least one of $X^1$, $X^2$ and $X^3$ are N.

3) $R^1$, $R^2$, $R^3$, $R^4$ and R are each the same or different, and each independently selected from a group consisting of hydrogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'—N($R^a$)($R^b$);

When $R^1$, $R^2$, $R^3$, $R^4$ and R are an aryl group, it is preferably a $C_6$-$C_{30}$ aryl group, more preferably an $C_6$-$C_{24}$ aryl group, for example, it may be phenylene, biphenyl, naphthalene, terphenyl, and the like.

When $R^1$, $R^2$, $R^3$, $R^4$ and R are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

When $R^1$, $R^2$, $R^3$, $R^4$ and R are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, When $R^1$, $R^2$, $R^3$, $R^4$ and R are an alkyl group, it is preferably a $C_1$-$C_{30}$ alkyl group, and more preferably a $C_1$-$C_{24}$ alkyl group.

When $R^1$, $R^2$, $R^3$, $R^4$ and R are an alkoxyl group, it is preferably a $C_1$-$C_{24}$ alkoxyl group.

When $R^1$, $R^2$, $R^3$, $R^4$ and R are an aryloxy group, it is preferably a $C_6$-$C_{24}$ aryloxy group.

4) $R^a$ and $R^b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

When $R^a$ and $R^b$ are an aryl group, it is preferably an $C_6$-$C_{30}$ aryl group, more preferably an $C_6$-$C_{24}$ aryl group, for example, it may be phenylene, biphenyl, naphthalene, terphenyl, and the like.

When $R^a$ and $R^b$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, When $R^a$ and $R^b$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

5) L', $L^1$, $L^2$, $L^3$, $L^4$, $L^5$ and $L^6$ are each independently selected from the group consisting of single bond; a $C_6$-$C_{60}$ arylene group; a fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_2$-$C_{60}$ heterocyclic group; a $C_1$-$C_{50}$ alkyl group; a $C_2$-$C_{20}$ alkenyl group; a $C_2$-$C_{20}$ alkynyl group;

wherein in case L', $L^1$, $L^2$, $L^3$, $L^4$, $L^5$ and $L^6$ are an arylene group, it is preferably an $C_6$-$C_{30}$ arylene group, more preferably an $C_6$-$C_{24}$ arylene group, for example, it may be phenylene, biphenyl, naphthalene, terphenyl, and the like.

when L', $L^1$, $L^2$, $L^3$, $L^4$, $L^5$ and $L^6$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when L', $L^1$, $L^2$, $L^3$, $L^4$, $L^5$ and $L^6$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, when L', $L^1$, $L^2$, $L^3$, $L^4$, $L^5$ and $L^6$ are an alkyl group, it is preferably a $C_1$-$C_{30}$ alkyl group, and more preferably a $C_1$-$C_{24}$ alkyl group.

6) $L^7$ is an $C_6$-$C_{30}$ arylene group; or fluorenylene group; when $L^7$ is an arylene group, it is preferably an $C_6$-$C_{30}$ arylene group, more preferably an $C_6$-$C_{24}$ arylene group, for example, it may be phenylene, biphenyl, naphthalene, terphenyl, and the like.

7) $Ar^1$, $Ar^2$, $Ar^3$, $Ar^4$, $Ar^5$ and $Ar^6$ are each independently selected from the group consisting of an $C_6$-$C_{60}$ aryl group; a $C_2$-$C_{60}$ heterocyclic group including at least one heteroatom of O, N, S, Si or P; a fluorenyl group; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; $C_6$-$C_{30}$ arylthio group; and $C_6$-$C_{30}$ aryloxy group; however, at least one of $Ar^4$, $Ar^5$ and $Ar^6$ is a substituted or unsubstituted naphthyl group.

When $Ar^1$, $Ar^2$, $Ar^3$, $Ar^4$, $Ar^5$ and $Ar^6$ are an aryl group, it is preferably an $C_6$-$C_{30}$ aryl group, more preferably an $C_6$-$C_{24}$ aryl group, for example, it may be phenylene, biphenyl, naphthalene, terphenyl, and the like.

When $Ar^1$, $Ar^2$, $Ar^3$, $Ar^4$, $Ar^5$ and $Ar^6$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when $Ar^1$, $Ar^2$, $Ar^3$, $Ar^4$, $Ar^5$ and $Ar^6$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, when $Ar^1$, $Ar^2$, $Ar^3$, $Ar^4$, $Ar^5$ and $Ar^6$ are an alkyl group, it is preferably a $C_1$-$C_{30}$ alkyl group, and more preferably a $C_1$-$C_{24}$ alkyl group.

when $Ar^1$, $Ar^2$, $Ar^3$, $Ar^4$, $Ar^5$ and $Ar^6$ are an alkoxyl group, it is preferably a $C_1$-$C_{24}$ alkoxyl group.

when $Ar^1$, $Ar^2$, $Ar^3$, $Ar^4$, $Ar^5$ and $Ar^6$ are an arylthio group, it is preferably a $C_1$-$O24$ arythio group.

when $Ar^1$, $Ar^2$, $Ar^3$, $Ar^4$, $Ar^5$ and $Ar^6$ are an aryloxy group, it is preferably a $C_1$-$C_{24}$ aryloxy group.

8) X is O or S.

9) a is an integer of 0 to 3, b is an integer of 0 to 4.

10) wherein, the aryl group, arylene group, heterocyclic group, fluorenyl group, fluorenylene group, aliphatic ring, fused ring group, alkyl group, alkenyl group, alkoxy group, aryloxy group and arylthio group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; $C_8$-$C_{20}$ arylalkenyl group; and -L'—N($R^a$)($R^b$); the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the present invention provides an organic electronic element wherein at least one of ring A and ring B of Formula 1 is represented by any one of Formulas a-1 to a-6.

Formula a-1

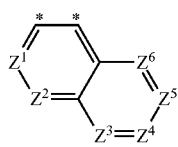

Formula a-2

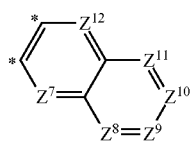

Formula a-3

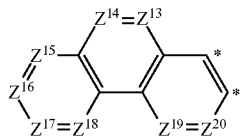

-continued

Formula a-4

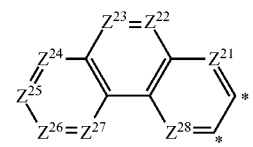

Formula a-5

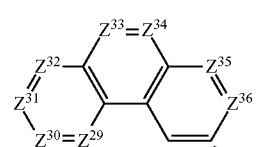

Formula a-6

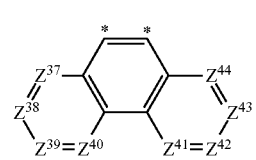

{In Formulas a-1 to a-6,

1) $Z^1$ to $Z^{44}$ are each independently $CR^a$ or N, $Z^1$ to $Z^{44}$ bonded to $L^3$ are carbon (C), 2) $R^a$ is the same as the definition of $R^1$ in Formula 1,

*indicates the position to be condensed.}

Also, the present invention provides an organic electronic element including a compound wherein $L^1$, $L^3$, $L^4$, $L^5$ and $L^6$ are represented by any one of the following Formulas b-1 to b-16.

Formula b-1

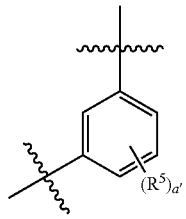

Formula b-2

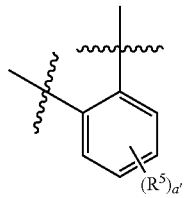

Formula b-3

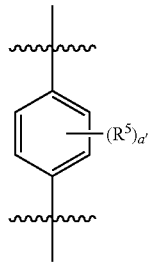

Formula b-4
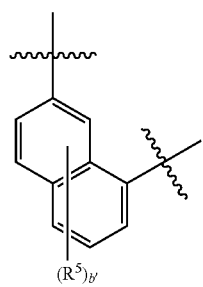
Formula b-5
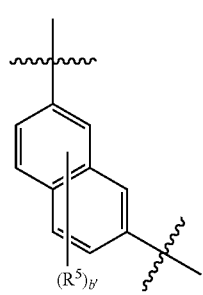
Formula b-6
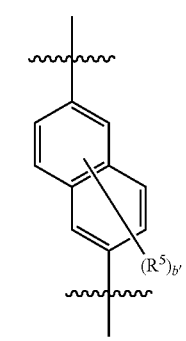
Formula b-7
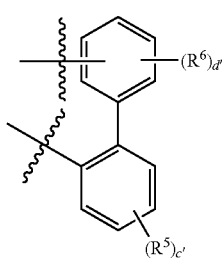
Formula b-8
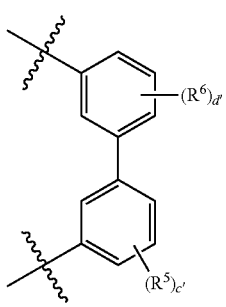
Formula b-9
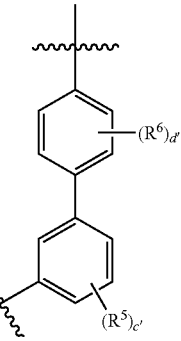
Formula b-10
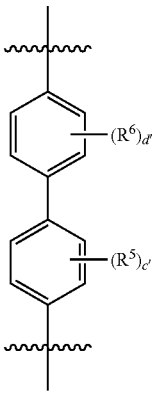
Formula b-11
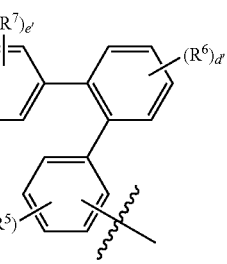
Formula b-12
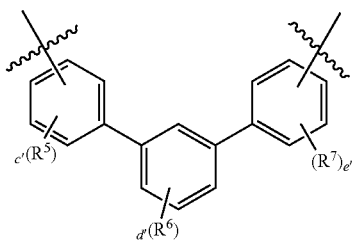
Formula b-13
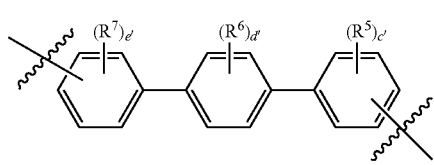
Formula b-14
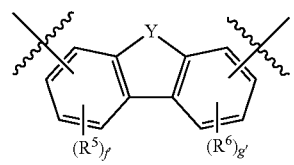

-continued

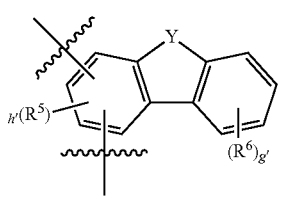
Formula b-15

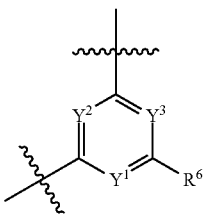
Formula b-16

In Formulas b-1 to b-16, each symbol may be defined as follows.

1) Y is N-$L^8$—$Ar^7$, O, S or CR'R",

2) $L^8$ is the same as the definition of $L^1$ in Formula 1,

3) $Ar^7$ is the same as the definition of $Ar^1$ in Formula 1,

4) R' and R" are the same as definition of $R^1$ in Formula 1, or may be bonded to each other to form a ring, 5) a', c', d' and e' are each independently an integer of 0 to 4, and b' is an integer of 0 to 6, f' and g' are each independently an integer of 0 to 3, h' is an integer of 0 to 2, 6) $R^5$, $R^6$ and $R^7$ are each independently selected from the group consisting of hydrogen; deuterium; tritium; halogen; cyano group; nitro group; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -$L^a$-N($R^c$)($R^d$); or in case a', b', c', d', e', f', g' and h' are 2 or more, $R^5$, $R^6$ and $R^7$ are in plural being the same or different, and a plurality of $R^5$ or a plurality of $R^6$ or a plurality of $R^7$ or adjacent $R^5$ and $R^6$, or adjacent $R^6$ and $R^7$ may be bonded to each other to form an aromatic or a heteroaromatic ring, When $R^5$, $R^6$ and $R^7$ are an aryl group, it is preferably an $C_6$-$C_{30}$ aryl group, more preferably an $C_6$-$C_{24}$ aryl group, for example, it may be phenylene, biphenyl, naphthalene, terphenyl, and the like.

When $R^5$, $R^6$ and $R^7$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when $R^5$, $R^6$ and $R^7$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, when $R^5$, $R^6$ and $R^7$ are an alkyl group, it is preferably a $C_1$-$C_{30}$ alkyl group, and more preferably a $C_1$-$C_{24}$ alkyl group.

when $R^5$, $R^6$ and $R^7$ are an alkoxyl group, it is preferably a $C_1$-$C_{24}$ alkoxyl group.

when $R^5$, $R^6$ and $R^7$ are an aryloxy group, it is preferably a $C_1$-$C_{24}$ aryloxy group.

7) $L^a$ is the same as the definition of $L^1$ in Formula 1,

8) $R^c$ and $R^d$ are the same as the definition of $R^a$ in Formula 1,

9) $Y^1$, $Y^2$ and $Y^3$ are each independently $CR^e$ or N, provided that at least one of $Y^1$, $Y^2$ and $Y^3$ is N, 10) $R^e$ is selected from the group consisting of hydrogen; deuterium; tritium; halogen; cyano group; nitro group; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group;

When $R^e$ are an aryl group, it is preferably an $C_6$-$C_{30}$ aryl group, more preferably an $C_6$-$C_{24}$ aryl group, for example, it may be phenylene, biphenyl, naphthalene, terphenyl, and the like.

When $R^e$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when $R^e$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, when $R^e$ are an alkyl group, it is preferably a $C_1$-$C_{30}$ alkyl group, and more preferably a $C_1$-$C_{24}$ alkyl group.

when $R^e$ are an alkoxyl group, it is preferably a $C_1$-$C_{24}$ alkoxyl group.

when $R^e$ are an aryloxy group, it is preferably a $C_1$-$C_{24}$ aryloxy group.

11) Adjacent $R^5$ and $R^e$ may be bonded to each other to form an aromatic ring or a heteroaromatic ring, 12) ∿∿∿ indicates the position to be condensed.

The first host compound represented by Formula 1 is represented by any one of Formulas 1-1 to 1-8.

Formula 1-1

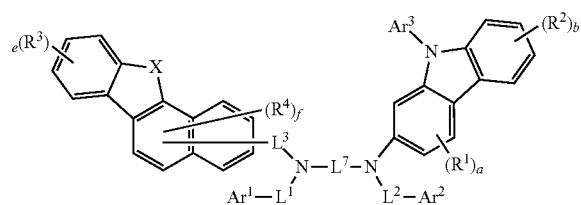

Formula 1-2

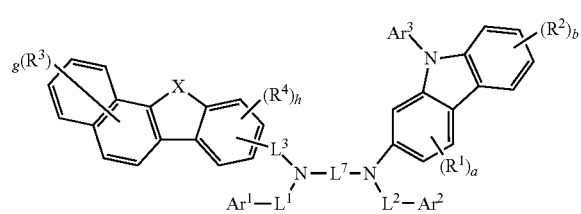

Formula 1-3

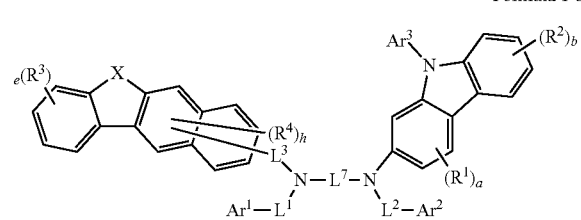

-continued

Formula 1-4
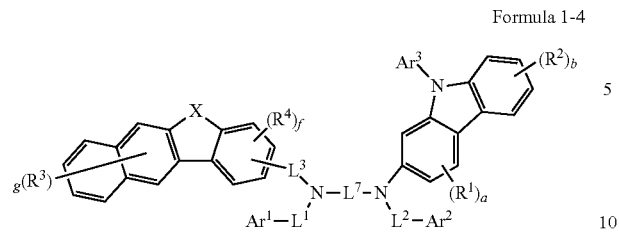

Formula 1-5
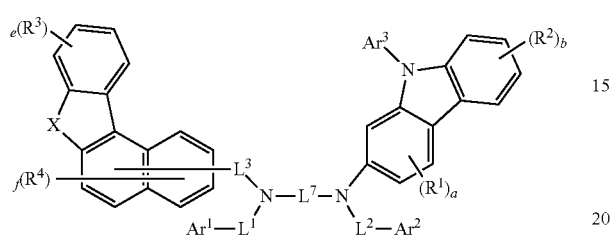

Formula 1-6
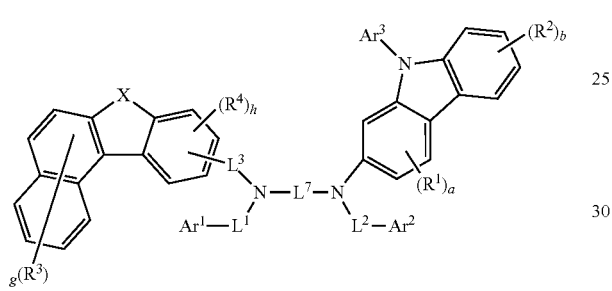

Formula 1-7
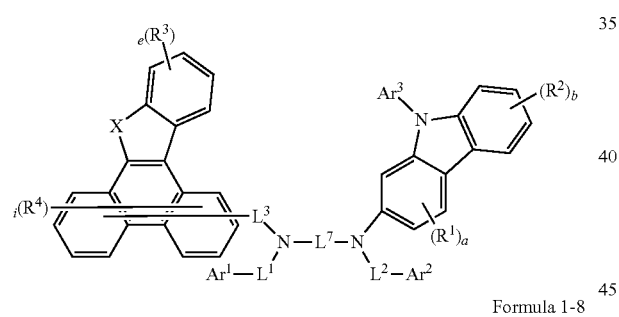

Formula 1-8
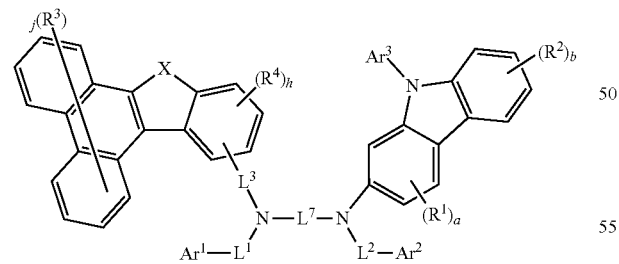

{In Formulas 1-1 to 1-8,

1) X, $Ar^1$, $Ar^2$, $Ar^3$, $L^1$, $L^2$, $L^3$, $L^7$, $R^1$, $R^2$, $R^3$, $R^4$, a and b are the same as defined in Formula 1, 2) e is an integer of 0 to 4, and f is an integer of 0 to 5, g is an integer of 0 to 6, h is an integer of 0 to 3, i is an integer of 0 to 7, j is an integer of 0 to 8.}

Specifically, the compound represented by Formula 1 may be any one of the following compounds.

P-1
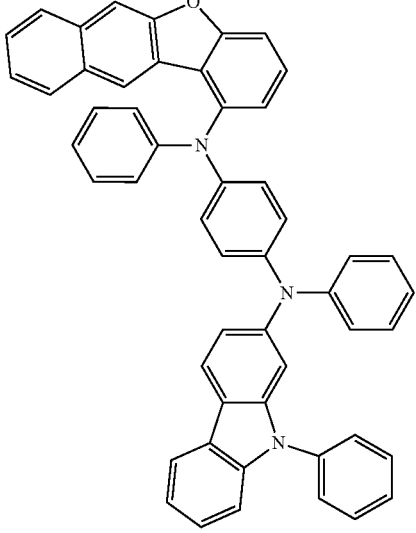

P-2
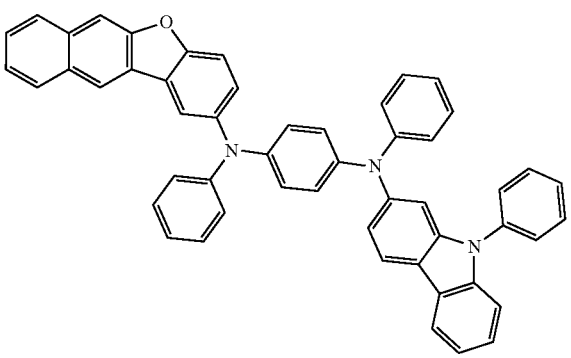

P-3
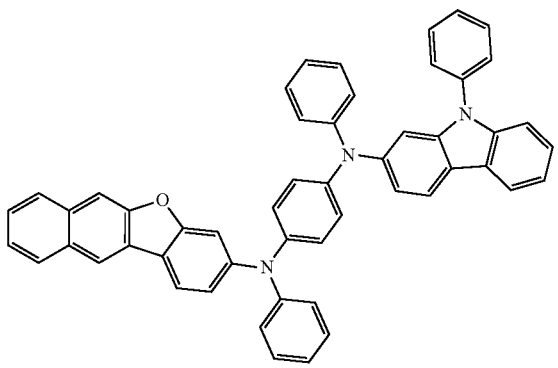

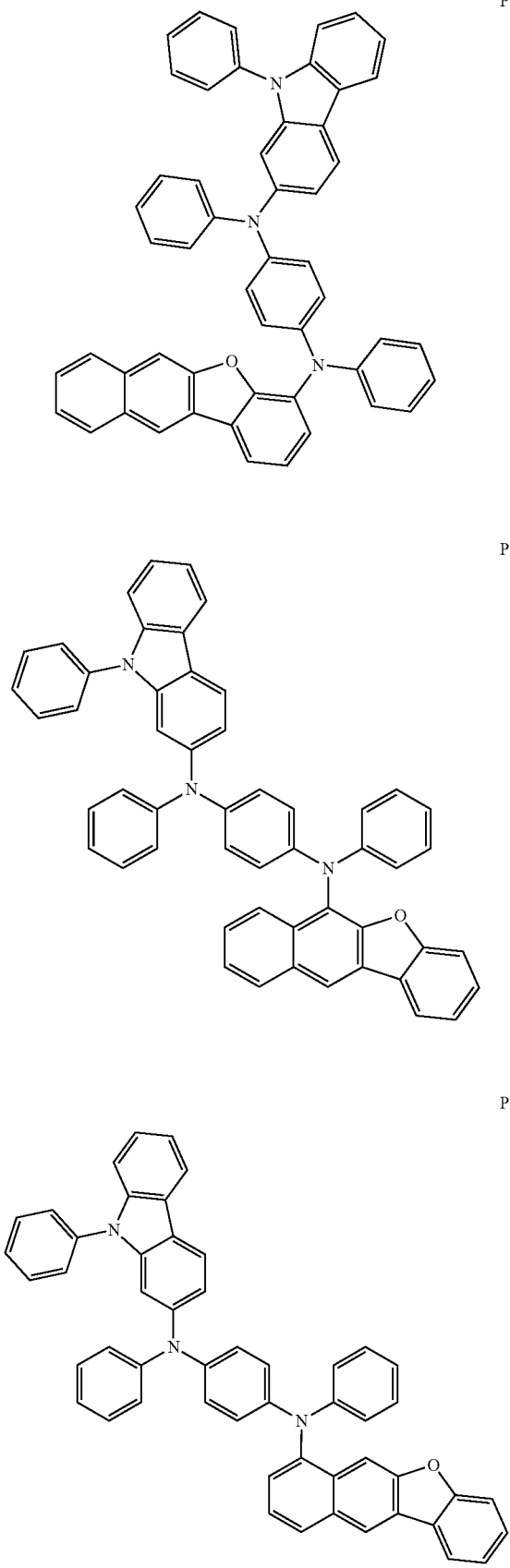
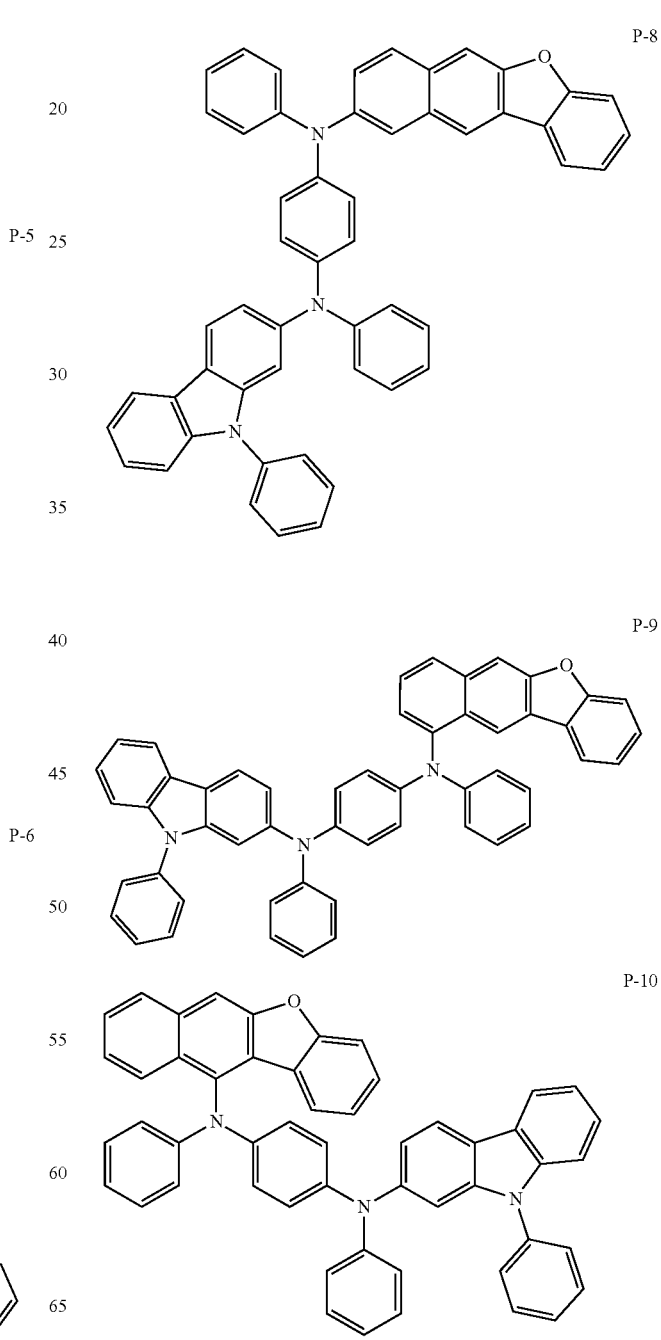

-continued
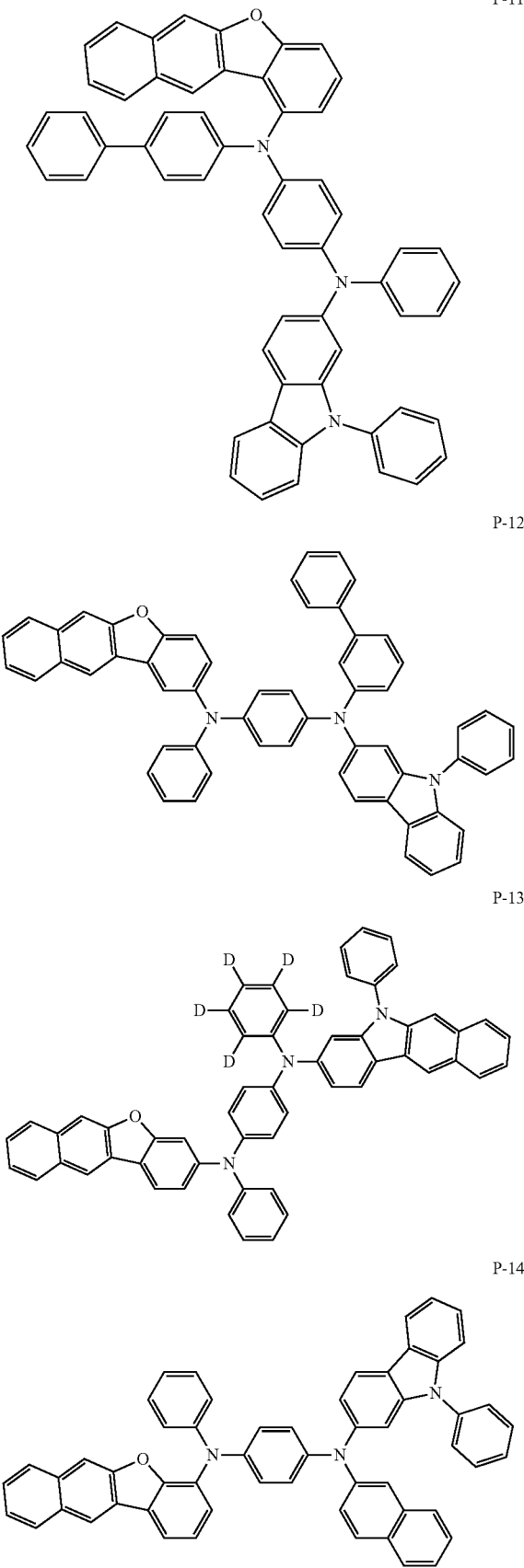
P-11
P-12
P-13
P-14
-continued
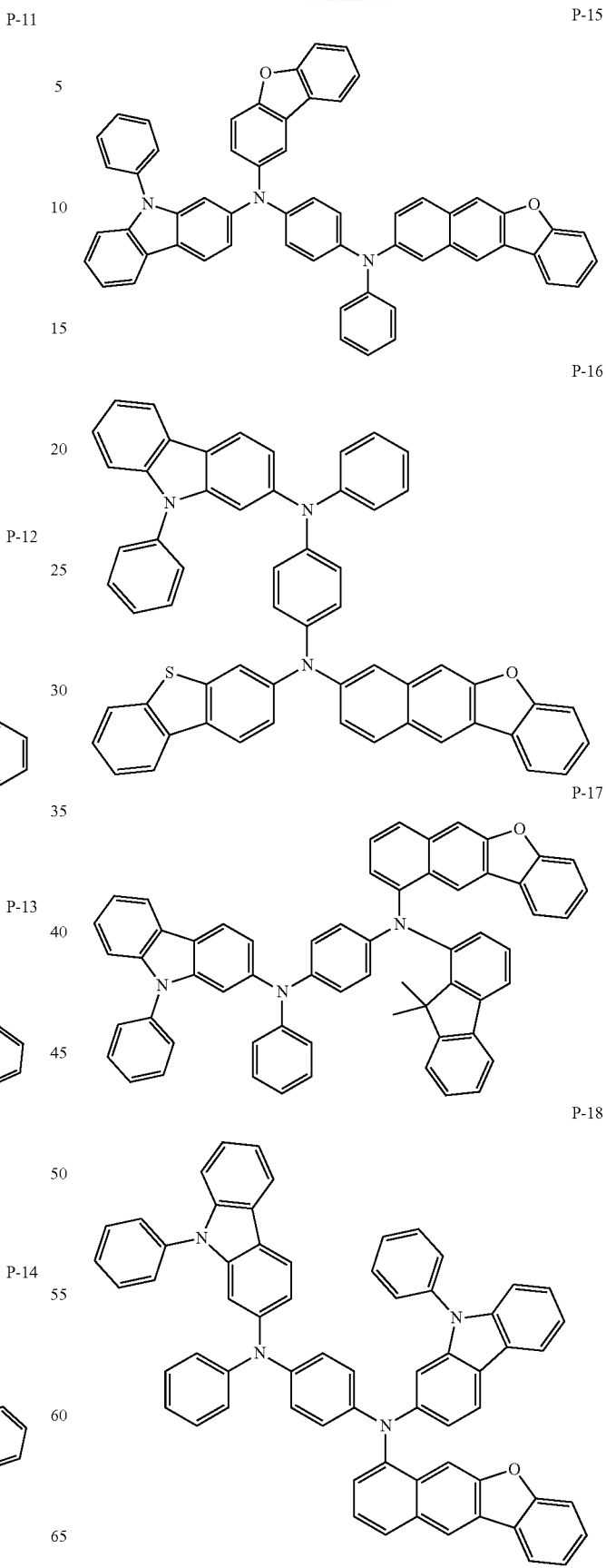
P-15
P-16
P-17
P-18

P-19
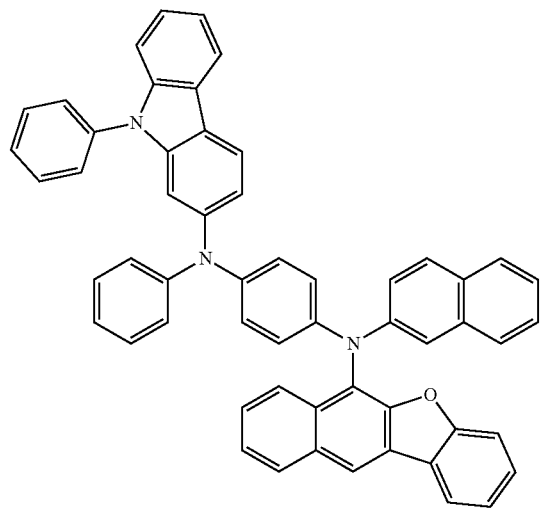
P-20
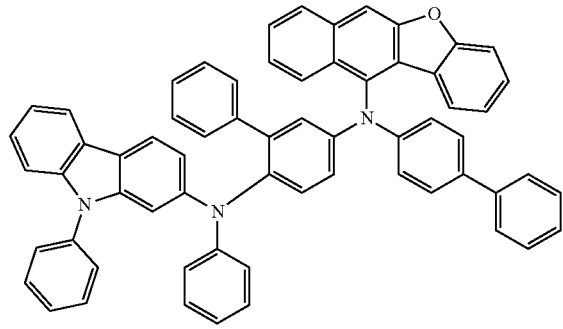
P-21
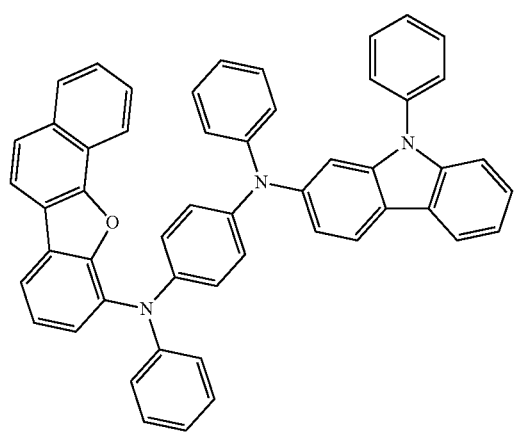
P-22
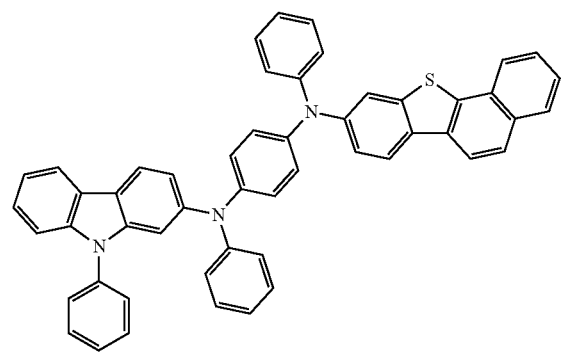
P-23
P-24
P-25
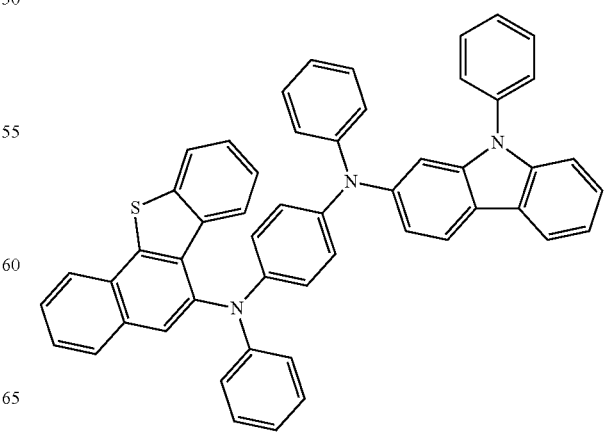

P-26
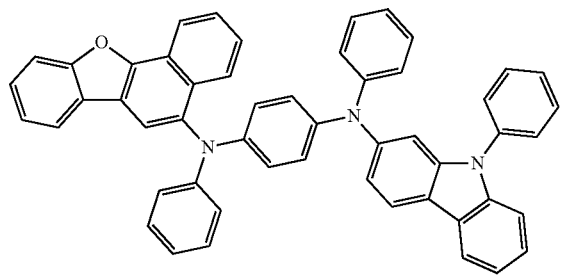
P-27
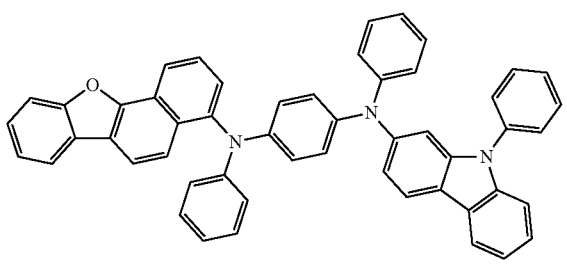
P-28
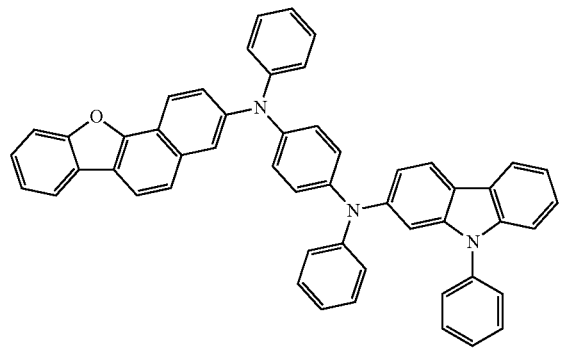
P-29
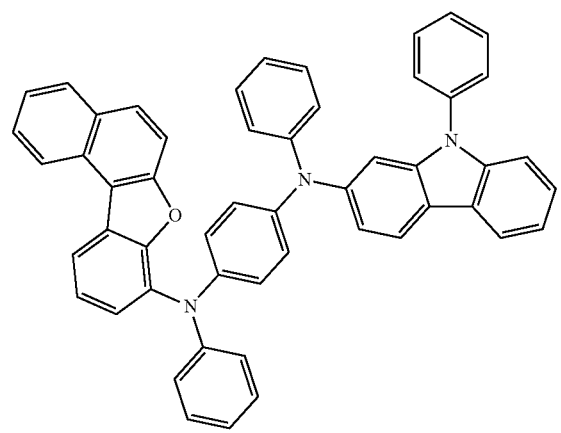
P-30
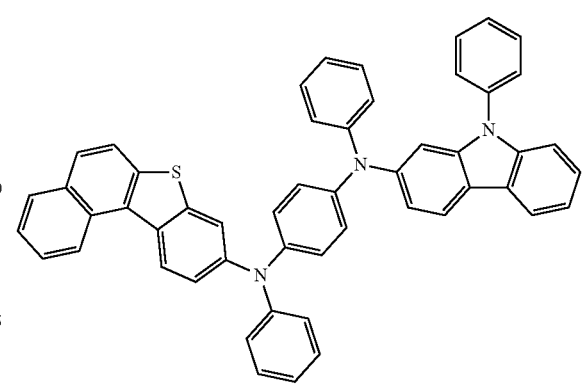
P-31
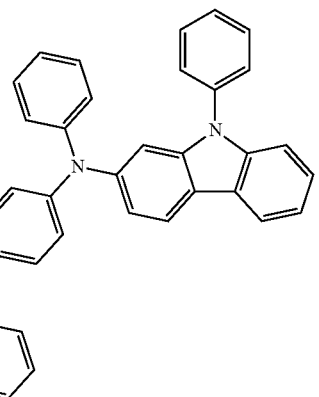
P-32
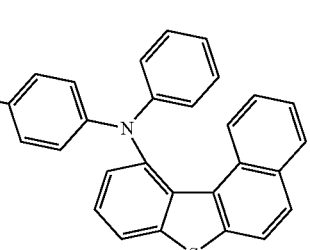
P-33
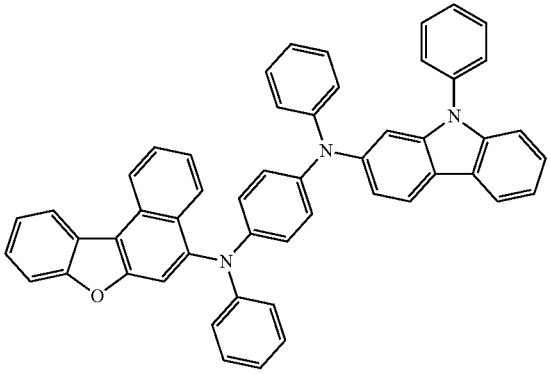

P-34
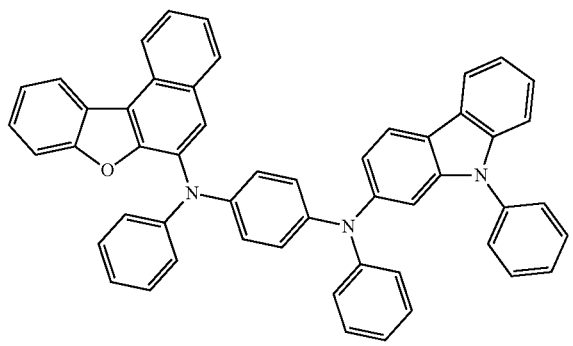
P-35
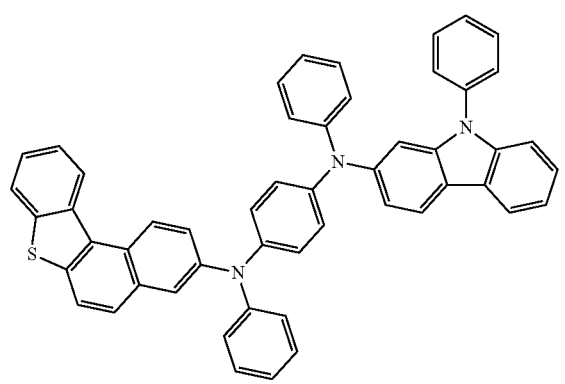
P-36
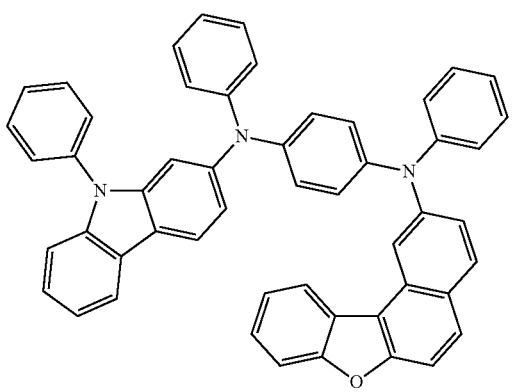
P-37
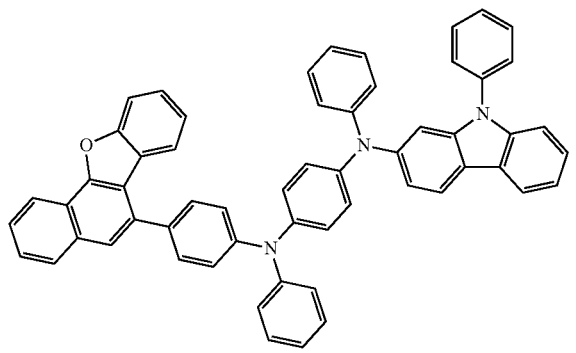
P-38
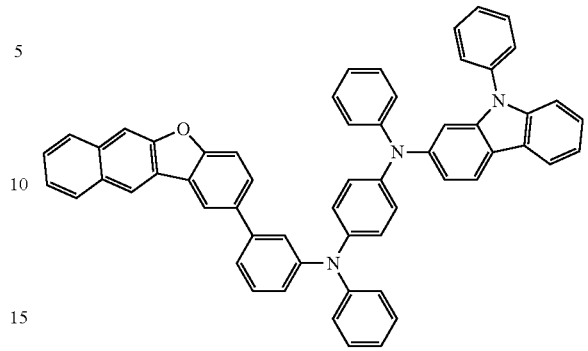
P-39
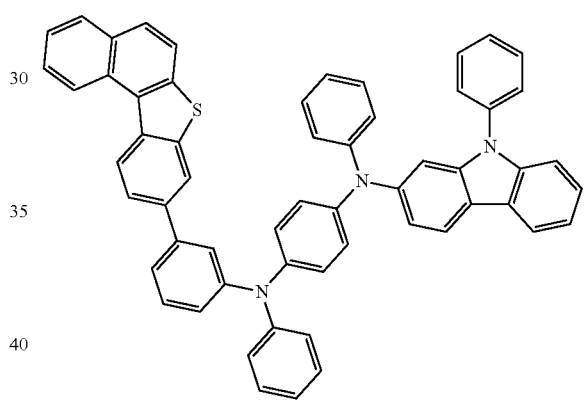
P-40
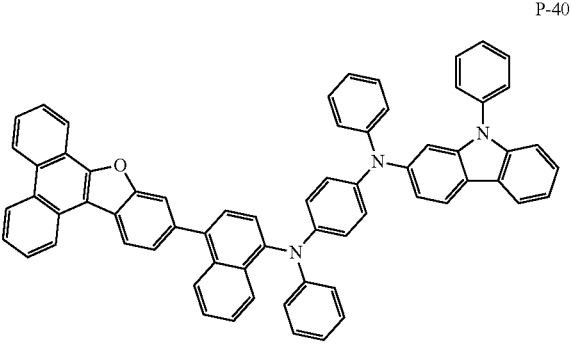

-continued
P-41
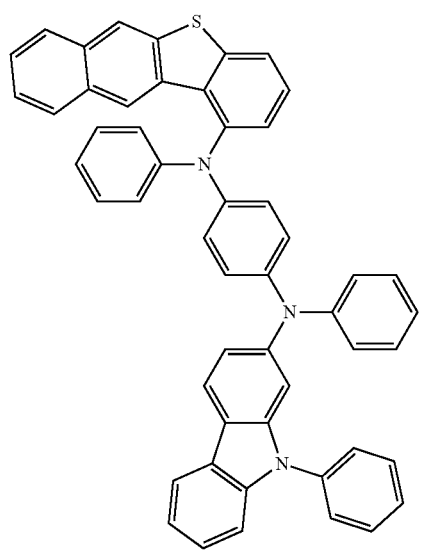
P-42
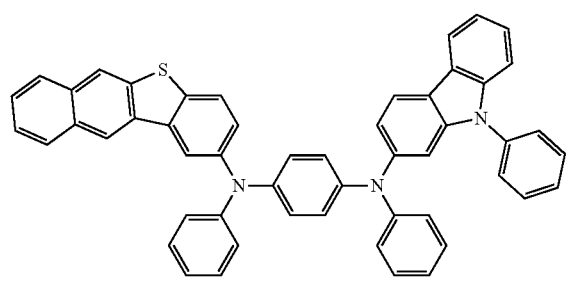
P-43
P-44
P-45
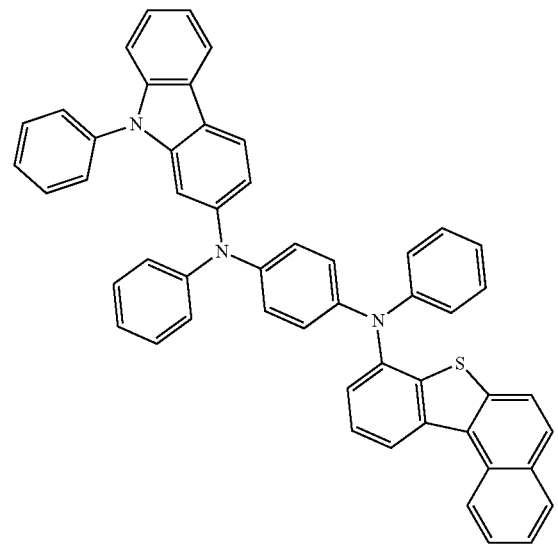
P-46
P-47
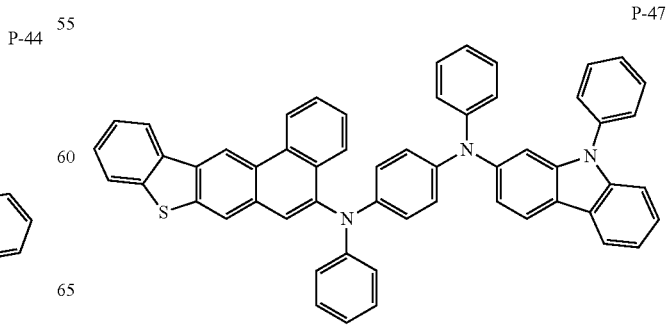

-continued
P-48
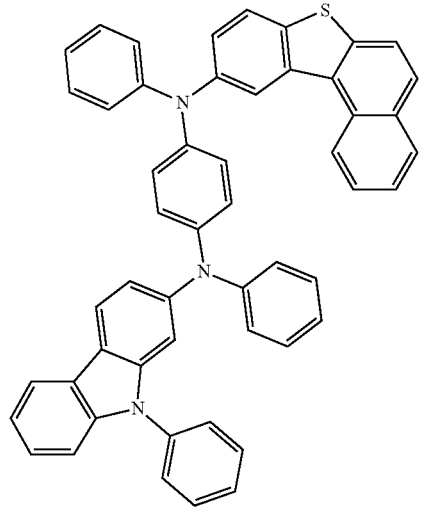
P-49
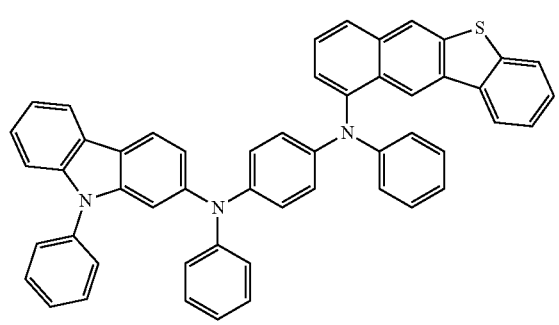
P-50
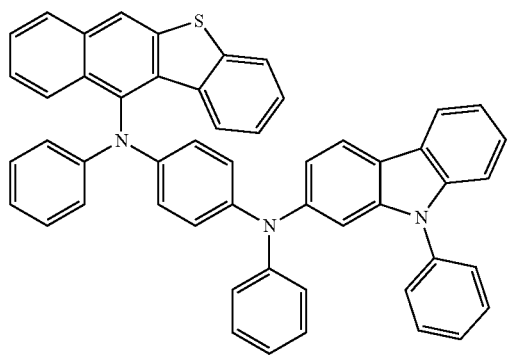
-continued
P-51
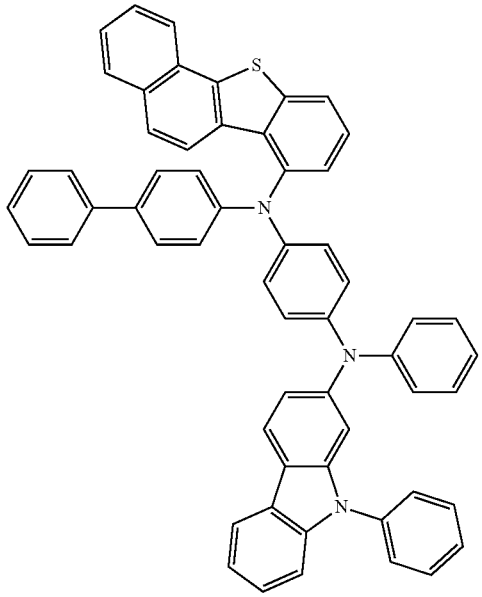
P-52
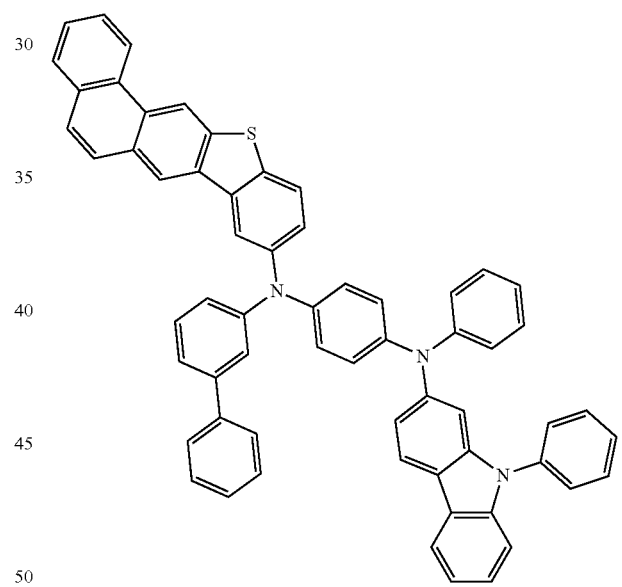
P-53
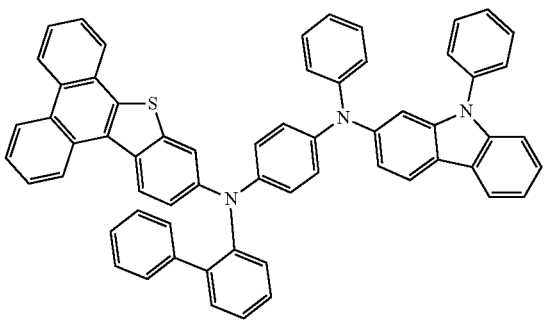

P-54
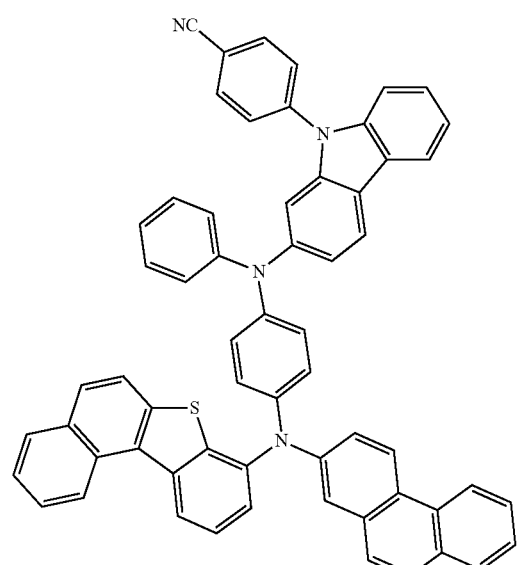
P-57
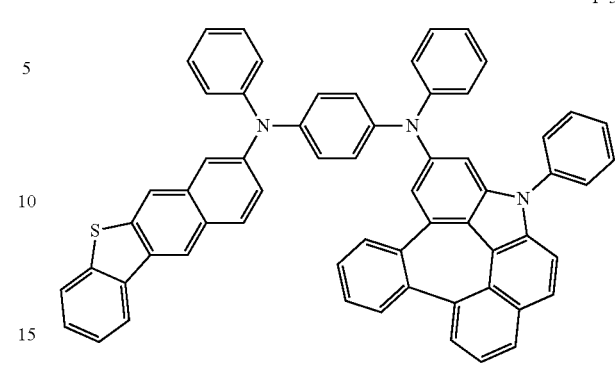
P-58
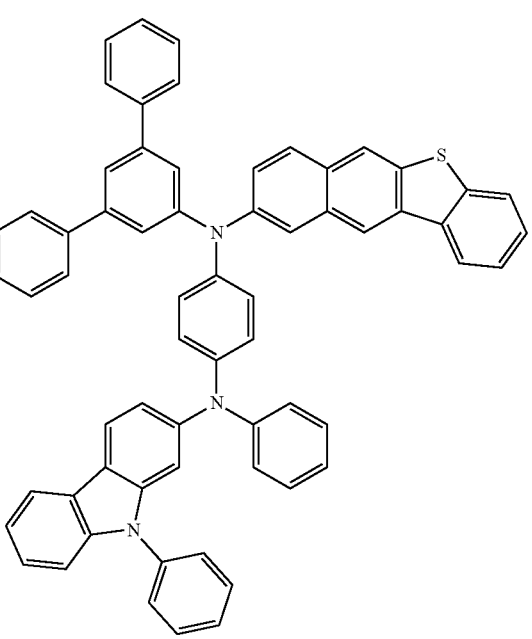
P-55
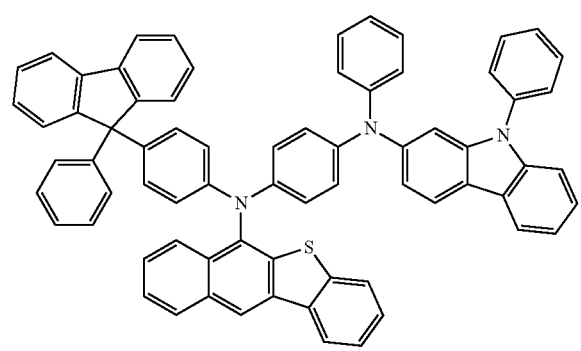
P-56
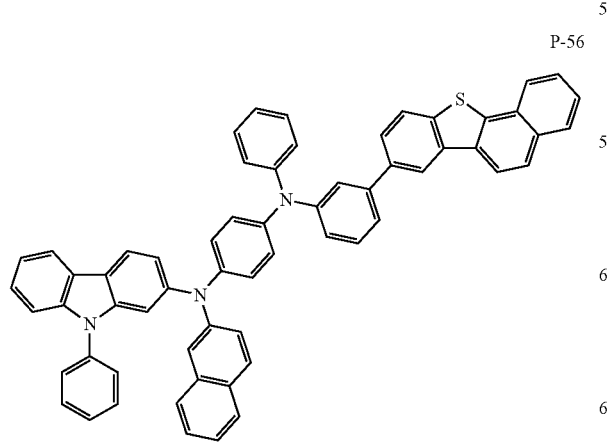
P-59
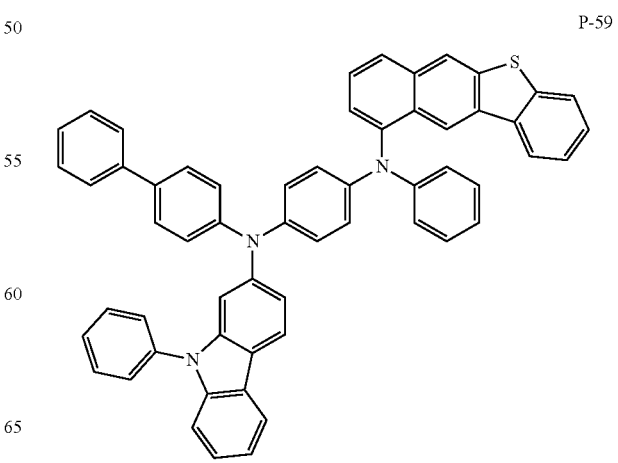

-continued
P-60
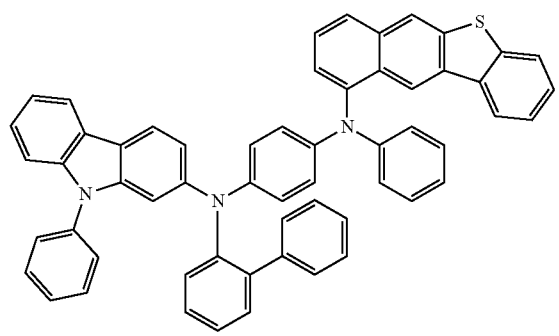
P-61
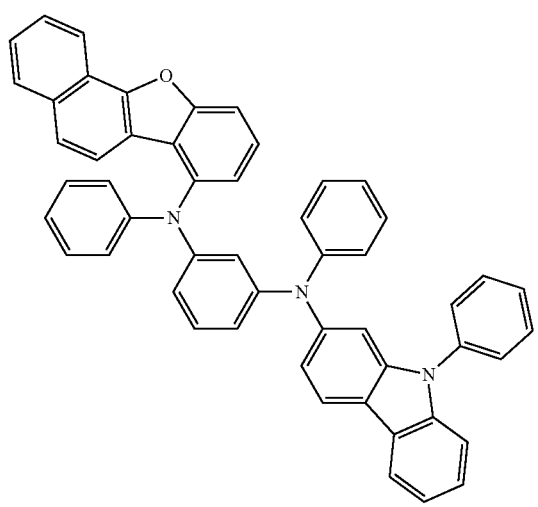
P-62
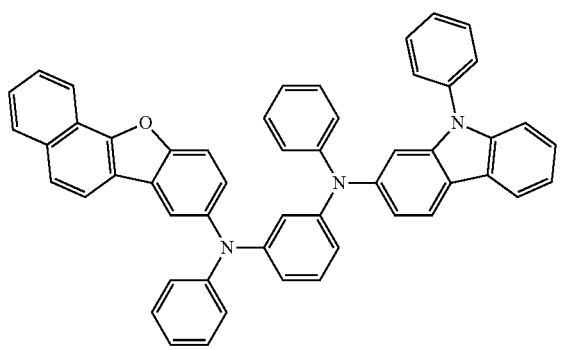
-continued
P-63
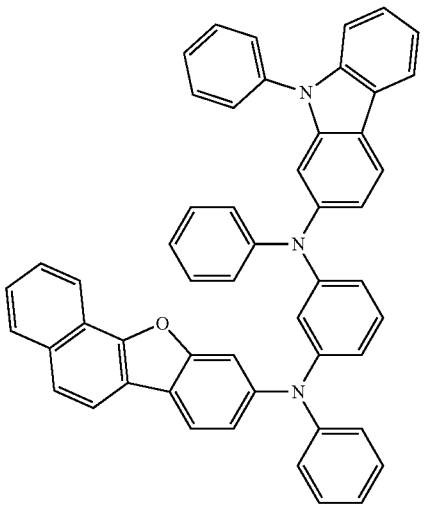
P-64
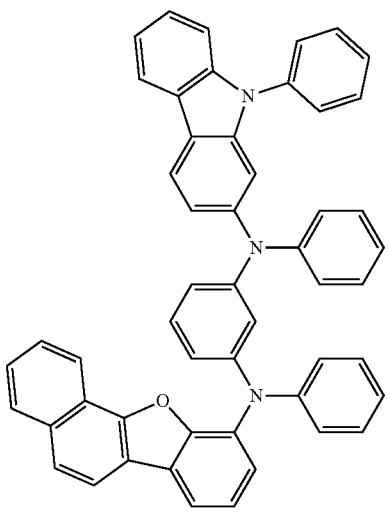
P-65
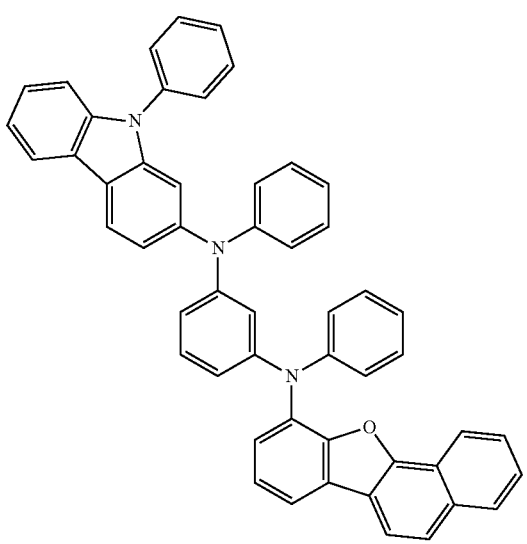

-continued
P-66
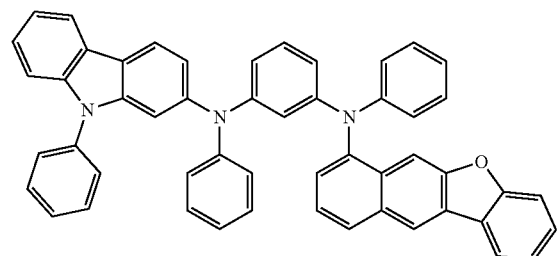
P-67
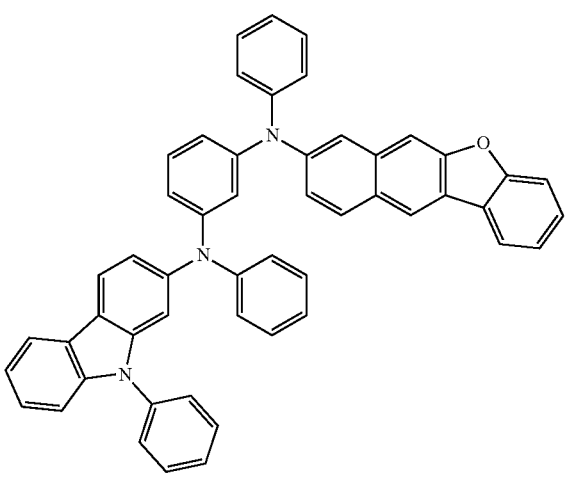
P-68
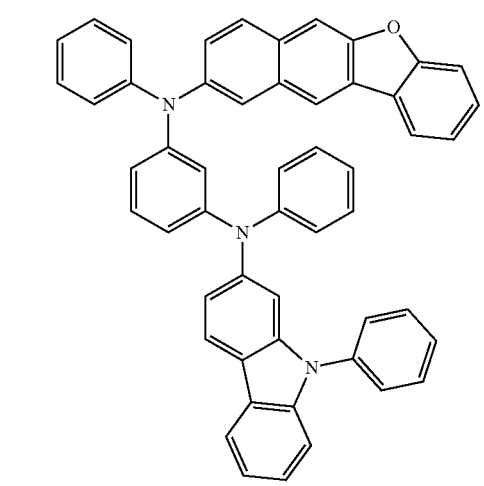
P-69
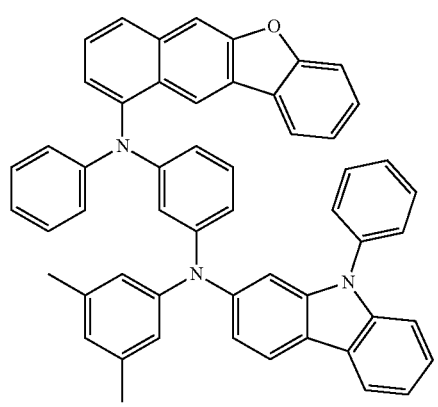
-continued
P-70
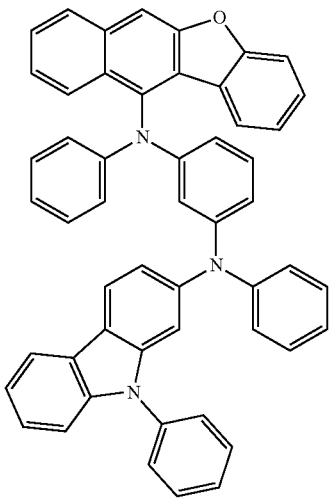
P-71
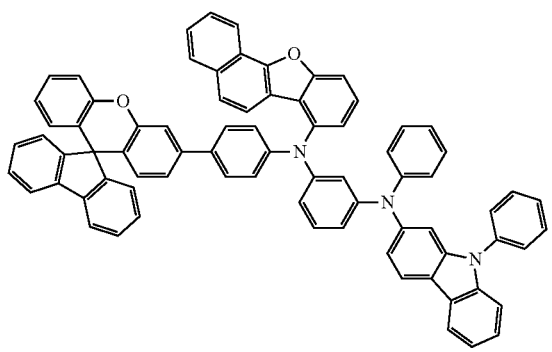
P-72
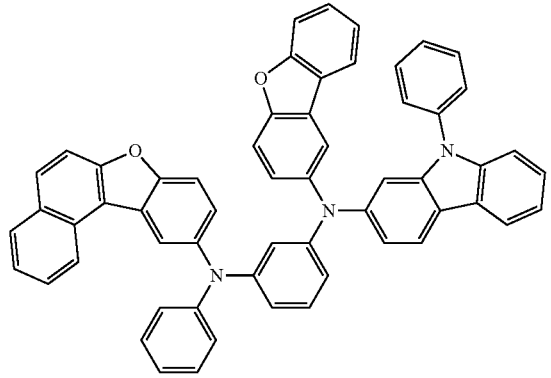

P-73
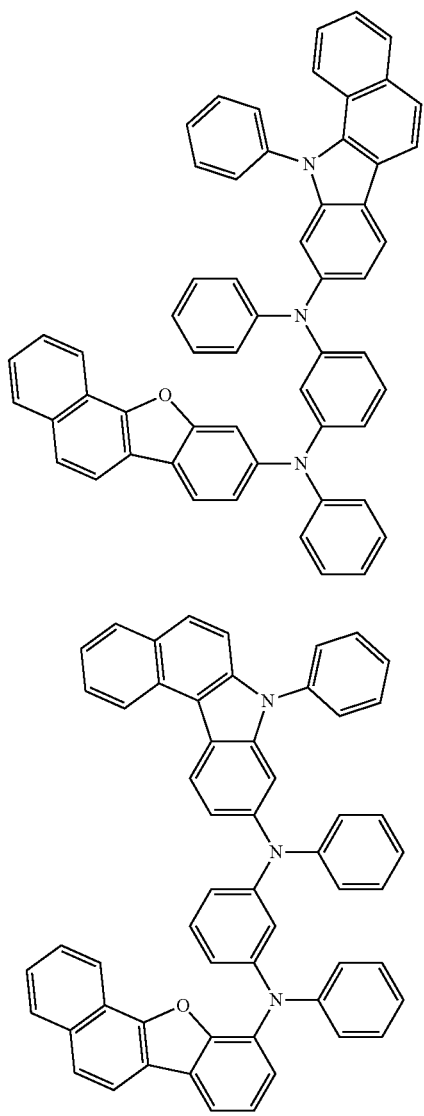
P-74
P-75
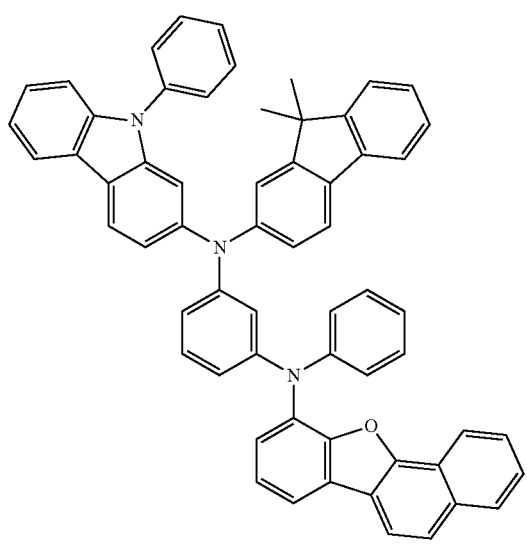
P-76
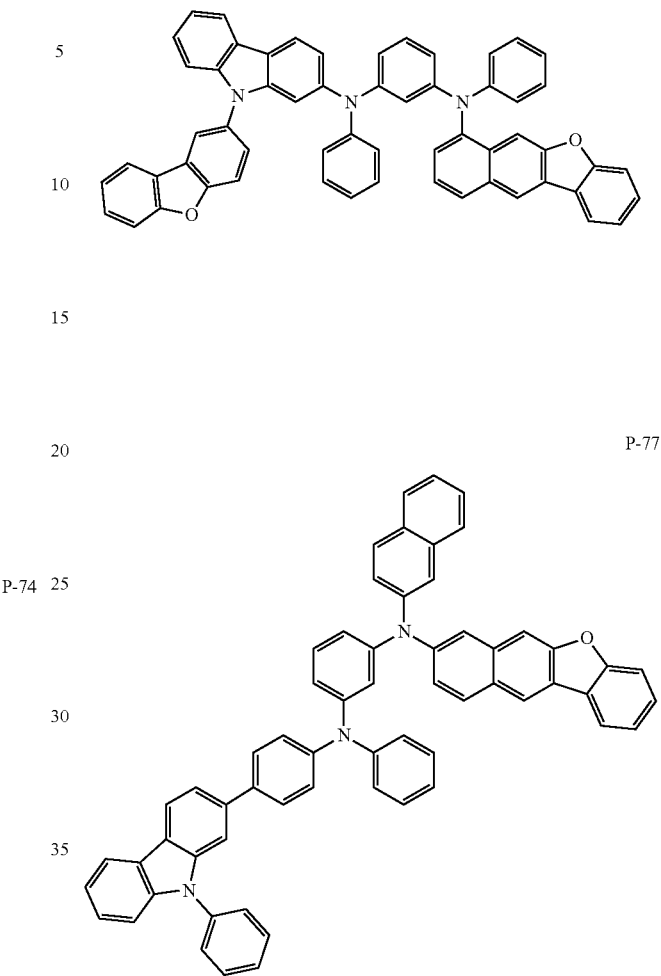
P-77
P-78
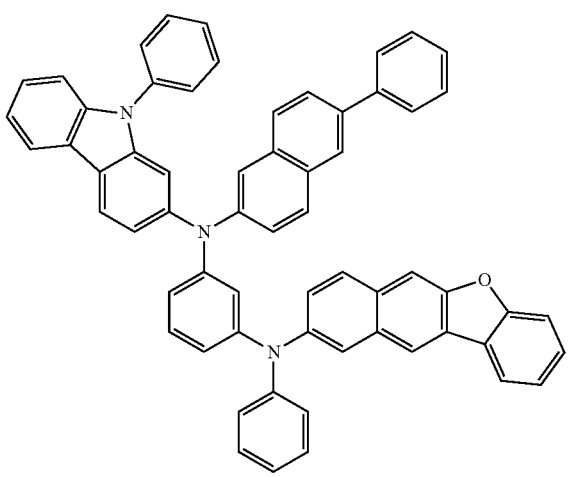

P-79
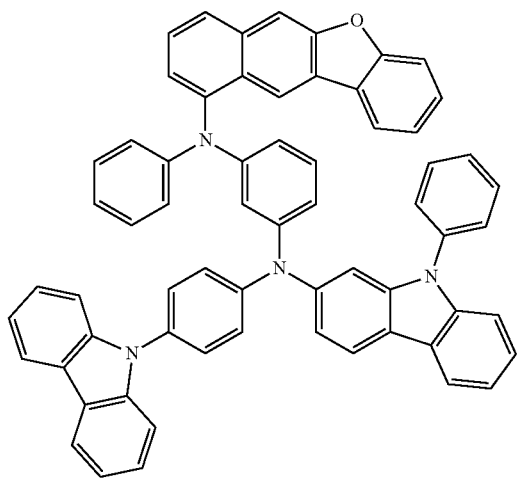
P-80
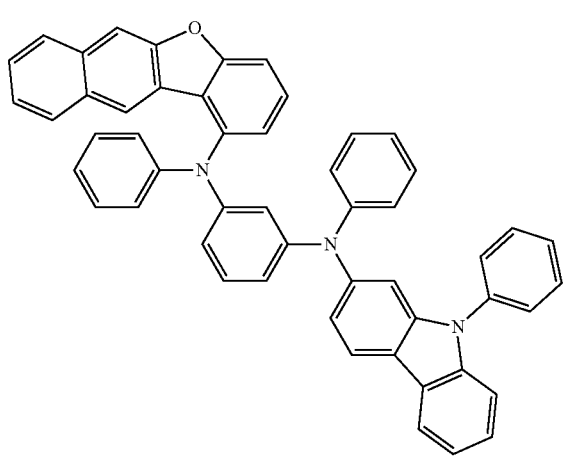
P-81
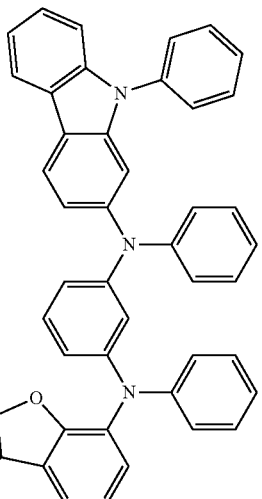
P-82
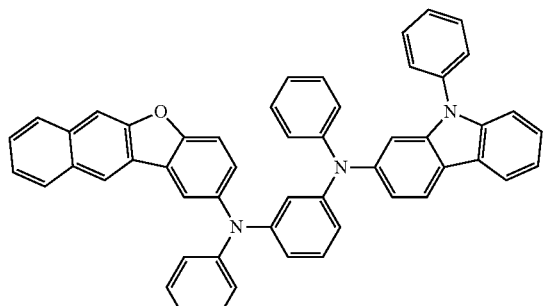
P-83
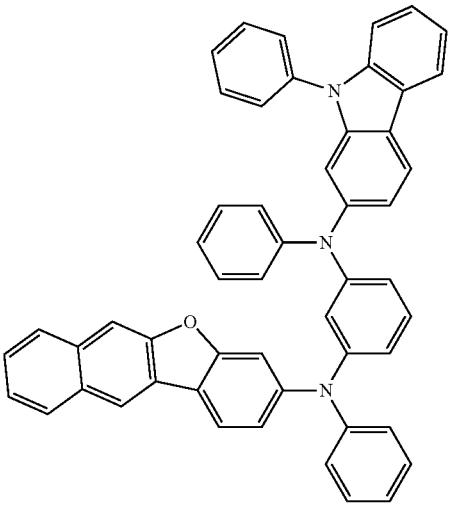
P-84
P-85
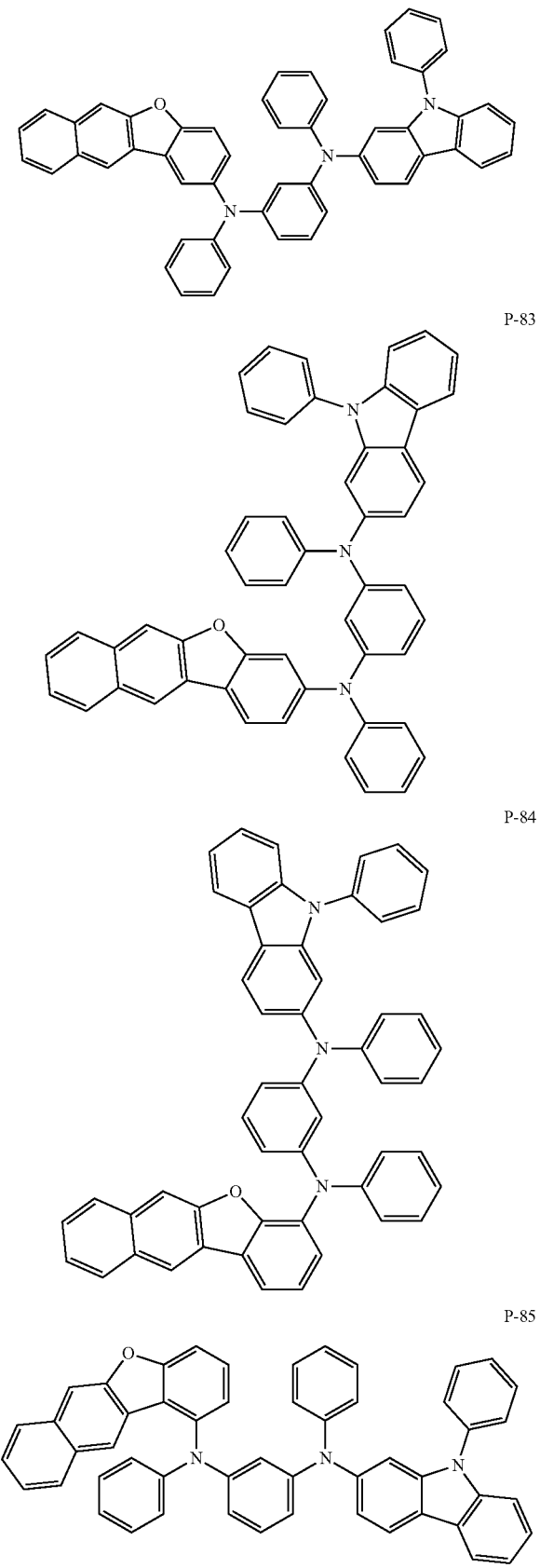

P-86
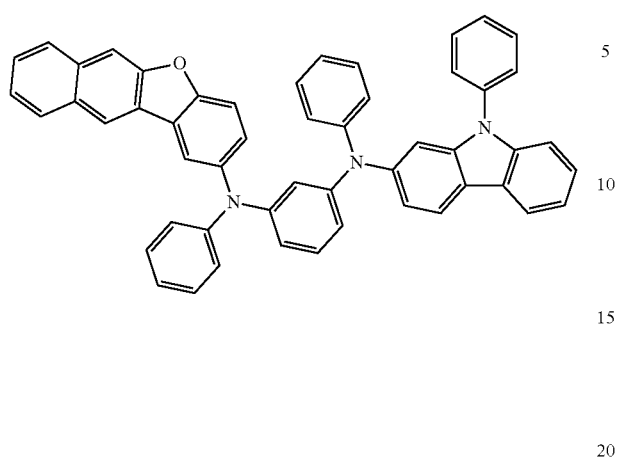
P-89
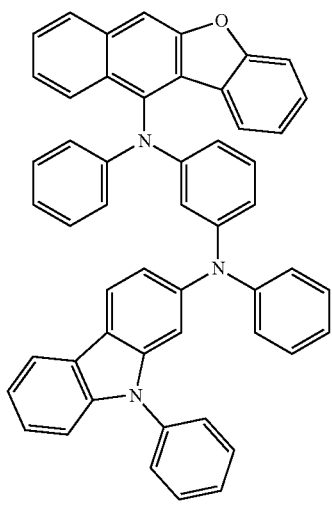
P-87
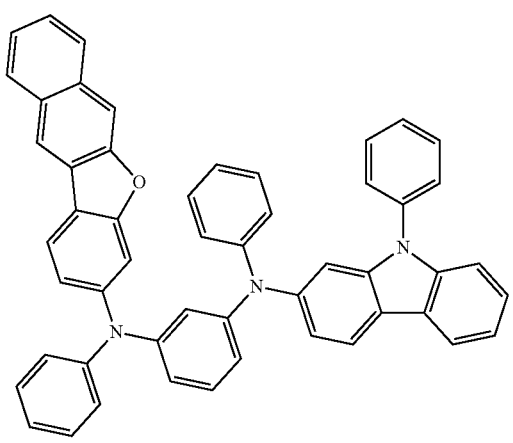
P-90
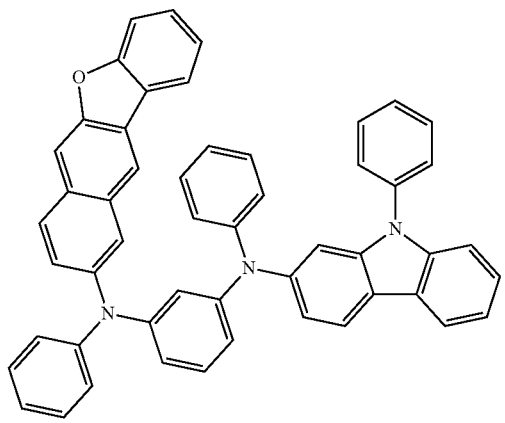
P-88
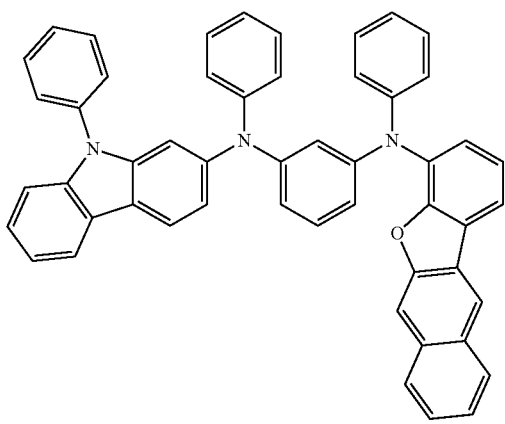
P-91
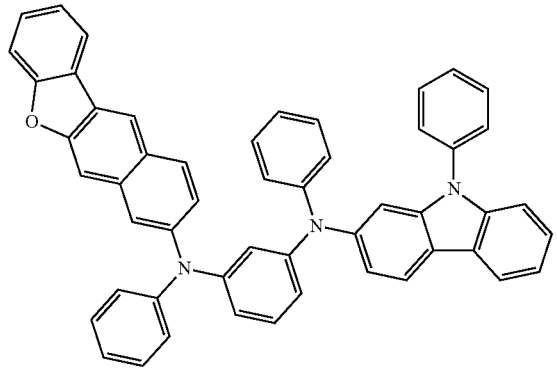

P-92
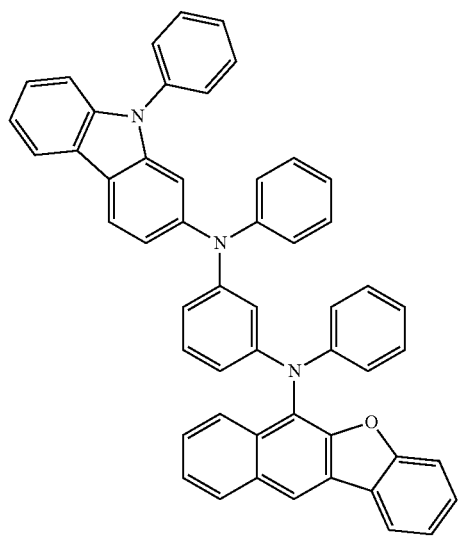
P-96
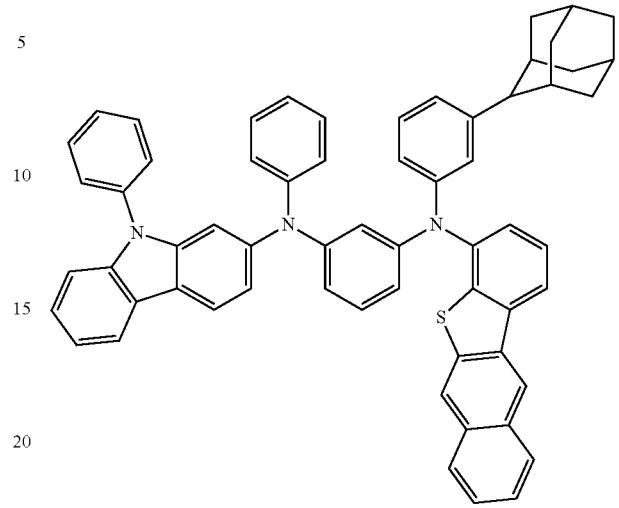
P-93
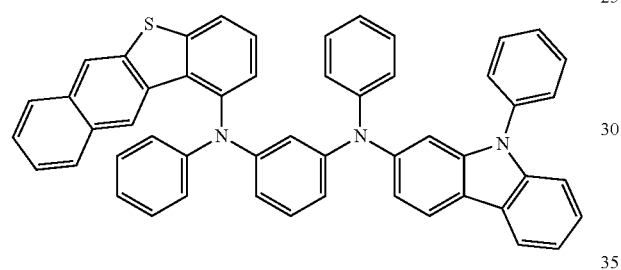
P-94
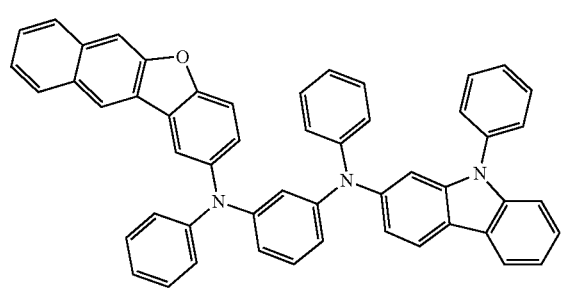
P-97
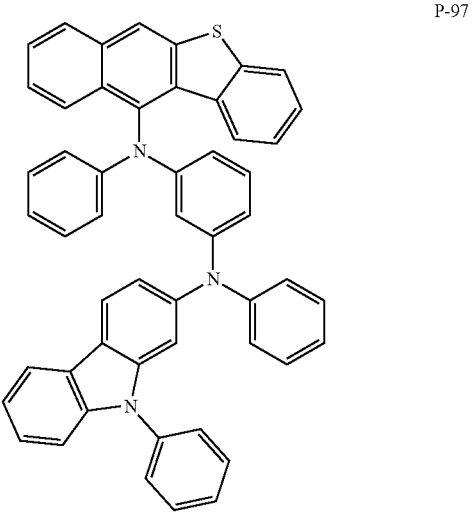
P-95
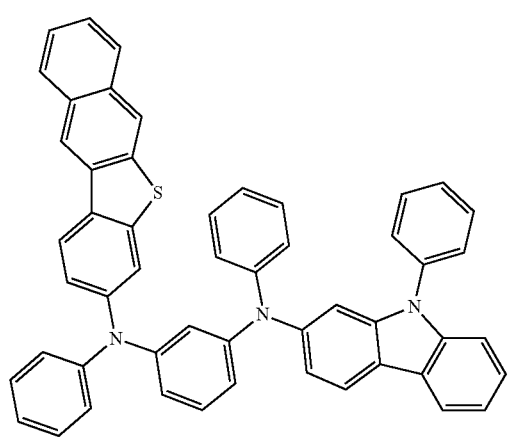
P-98
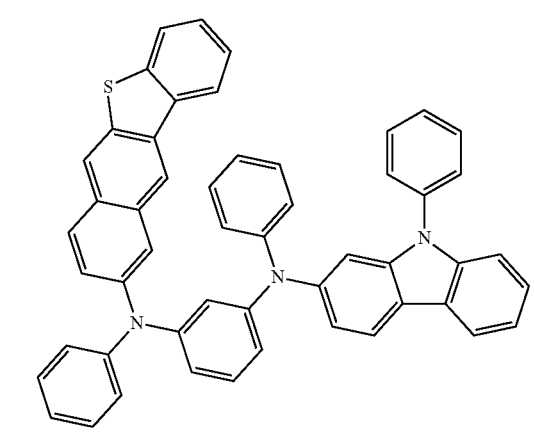

P-99
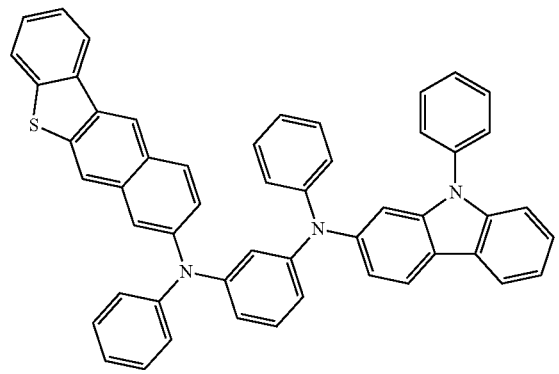
P-103
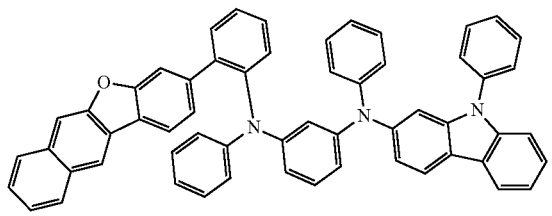
P-100
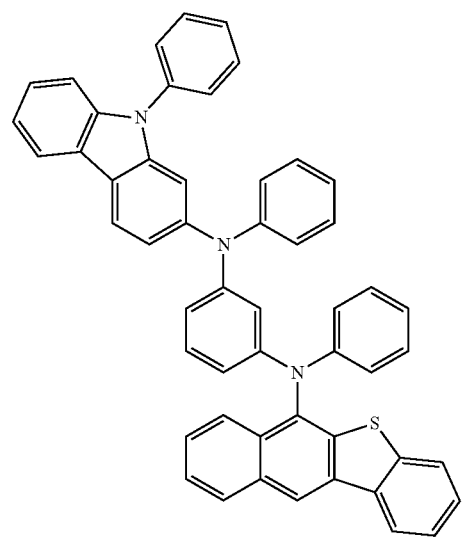
P-104
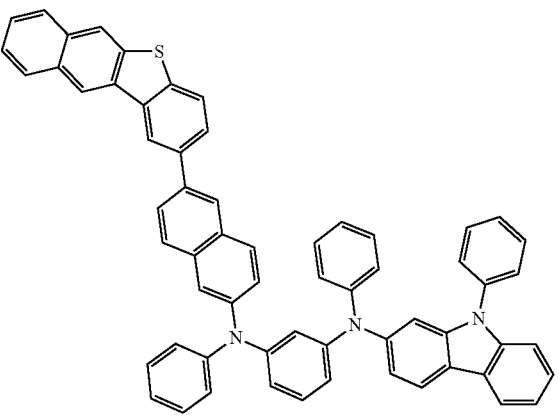
P-101
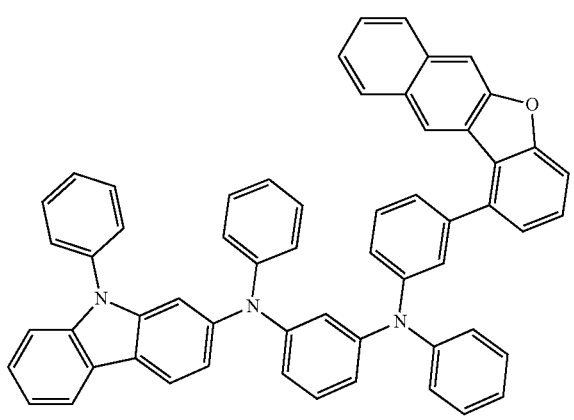
P-105
P-102
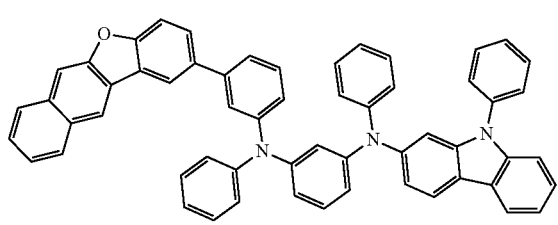
P-106
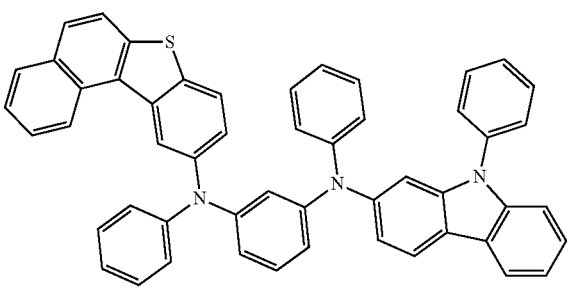

P-107
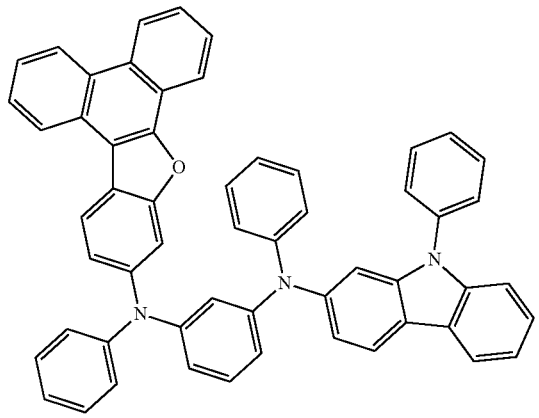
P-110
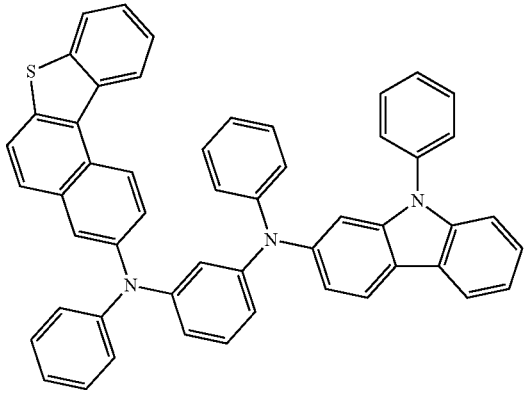
P-108
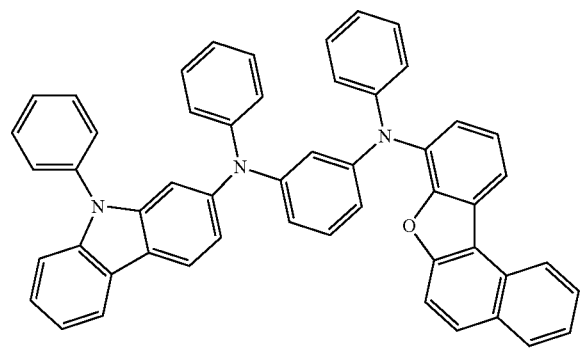
P-111
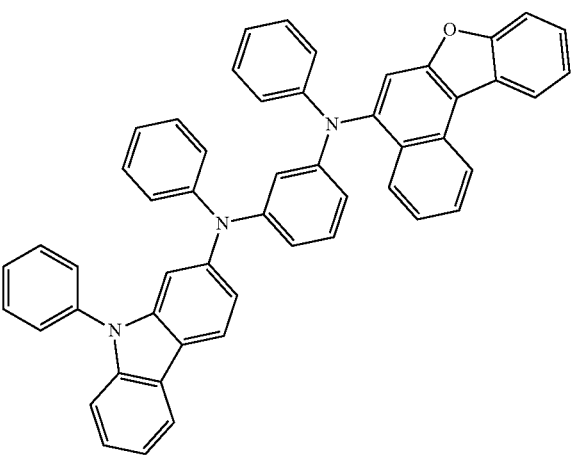
P-112
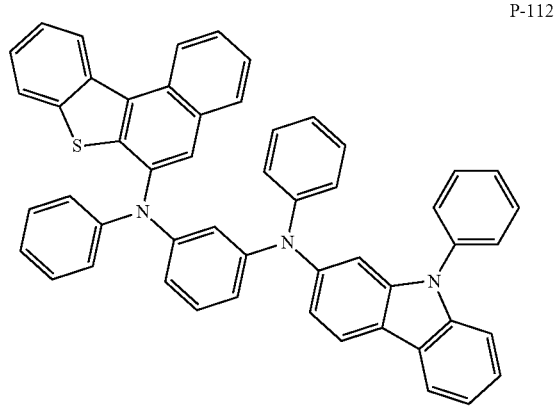
P-109
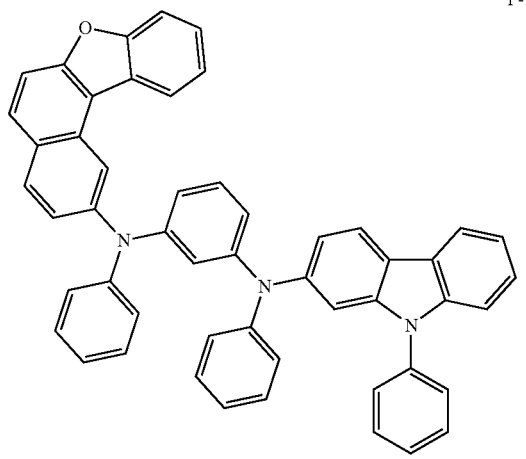
P-113
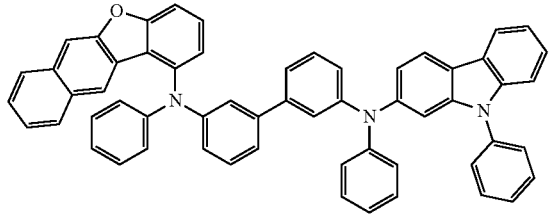

P-114
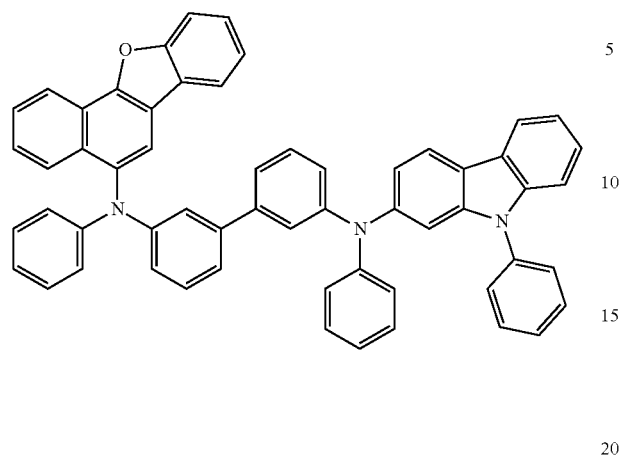
P-117
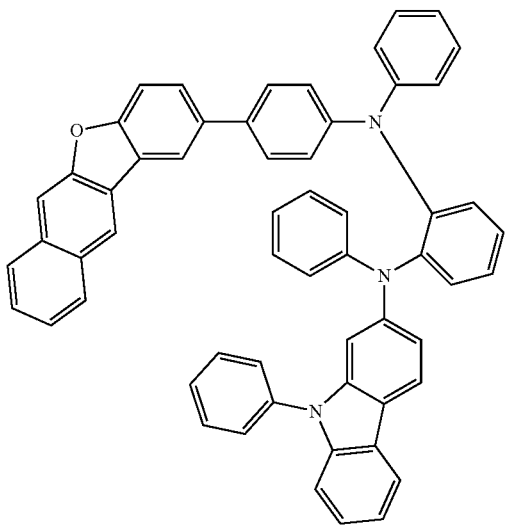
P-115
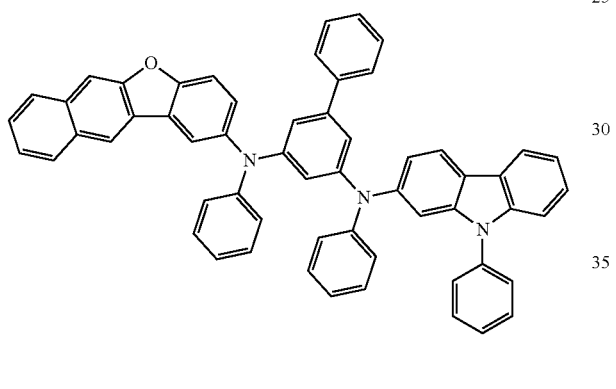
P-118
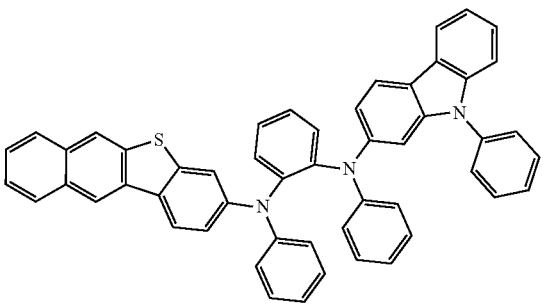
P-116
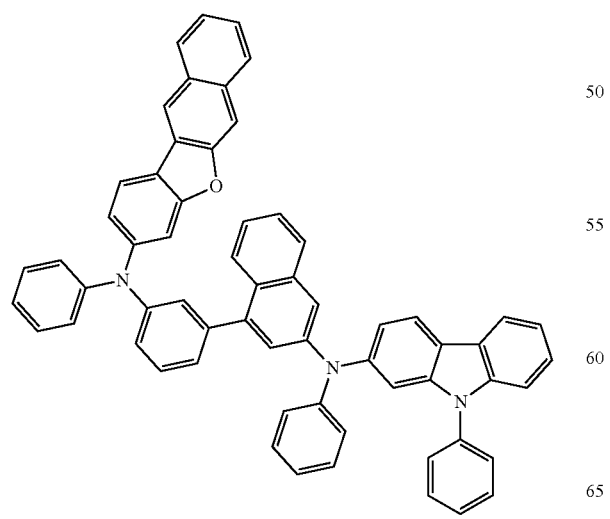
P-119
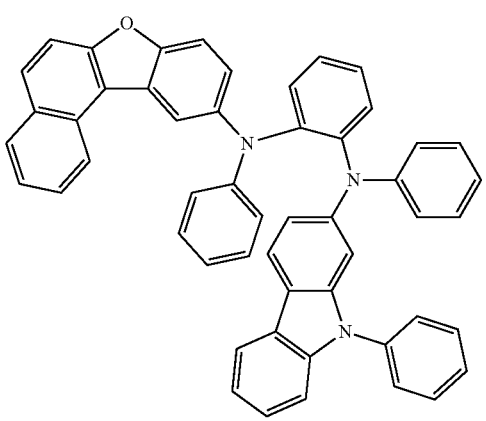

-continued
P-120
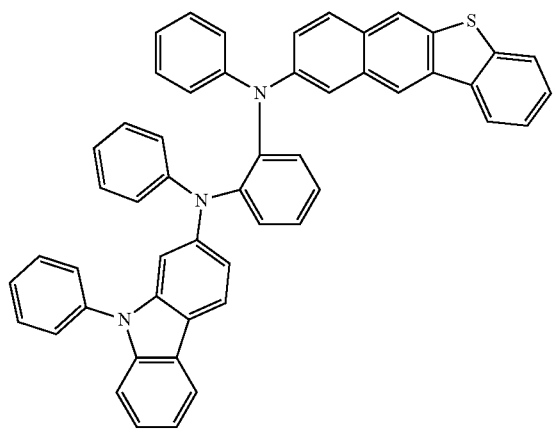
P-121
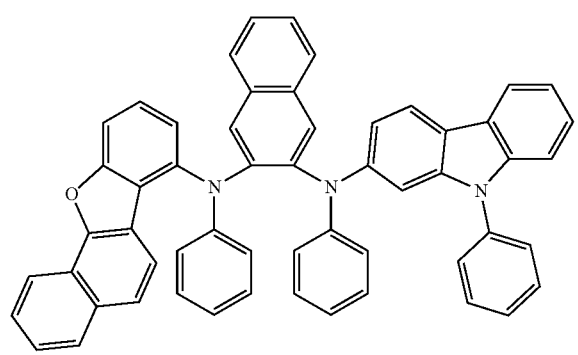
P-122
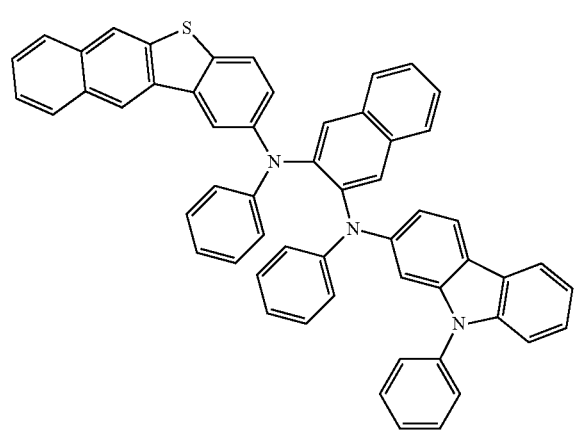
-continued
P-123
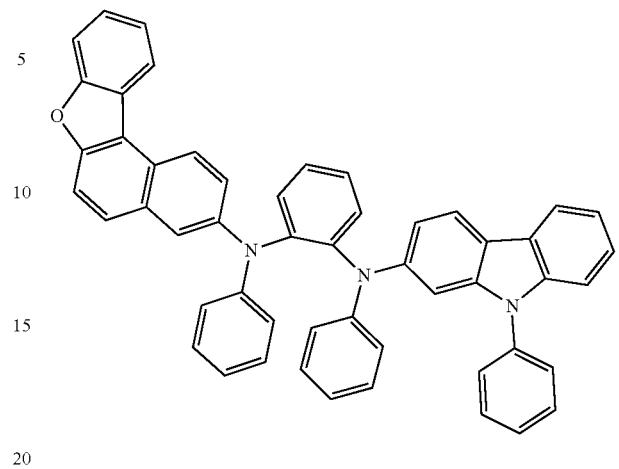
P-124
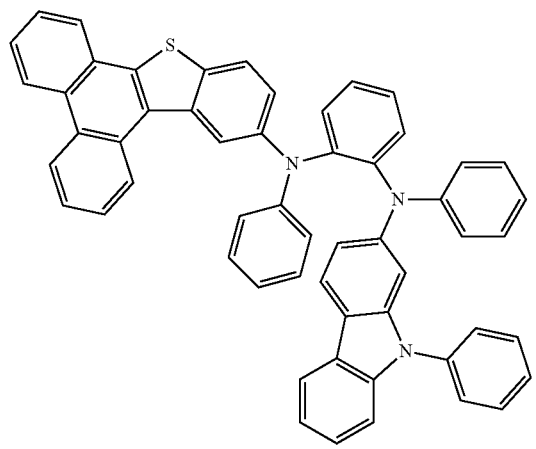
P-125
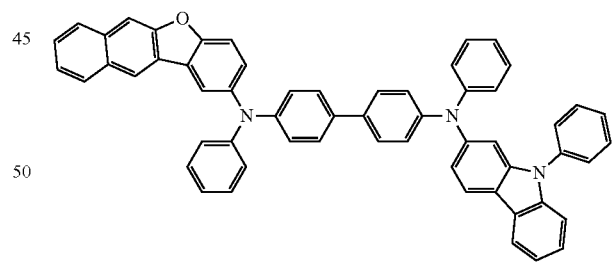
P-126
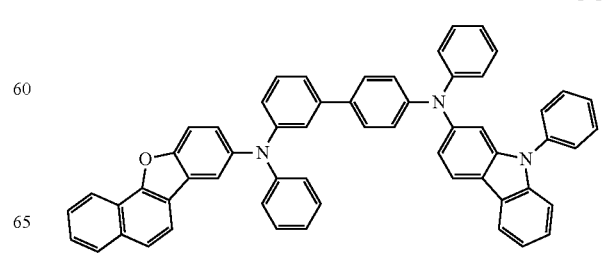

P-127

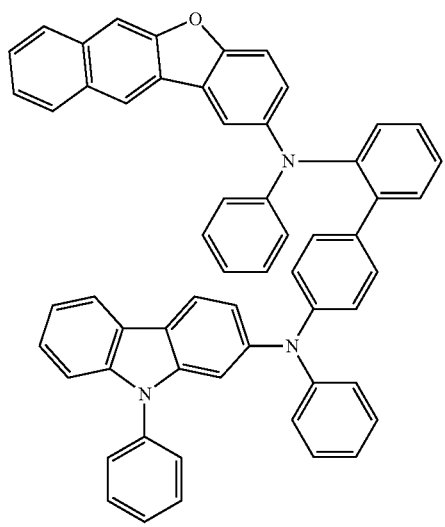

P-128

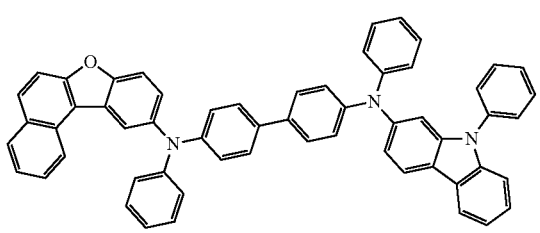

Also, at least one of Ar⁴ to Ar⁶ in Formula 2 is represented by Formula c-1 to Formula c-6

Formula c-1

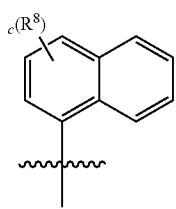

Formula c-2

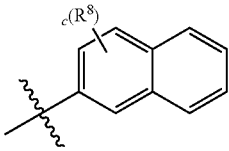

Formula c-3

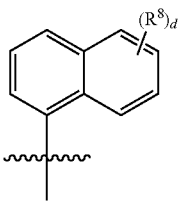

Formula c-4

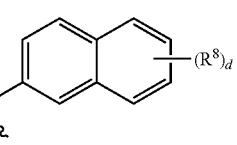

Formula c-5

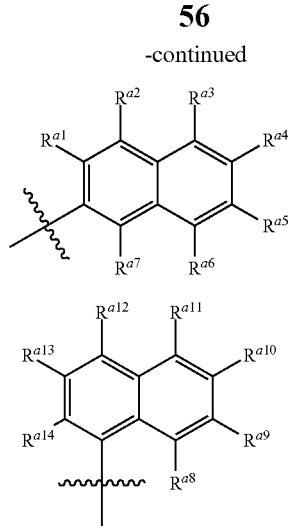

Formula c-6

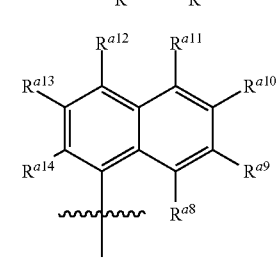

{In Formula c-1 to Formula c-6,

1) $R^8$ and $R^{a1}$ to $R^{a14}$ are each independently hydrogen; a $C_1$-$C_{20}$ alkyl group; a $C_6$-$C_{20}$ aryl group; a $C_6$-$C_{20}$ aryl group substituted by deuterium; a fluorenyl group; a $C_2$-$C_{20}$ heterocyclic group;

2) c is an integer of 0 to 3, d is an integer of 0 to 4.}

Also, the second host compound represented by Formula 2 is represented by any one of Formulas 2-1 to 2-4.

Formula 2-1

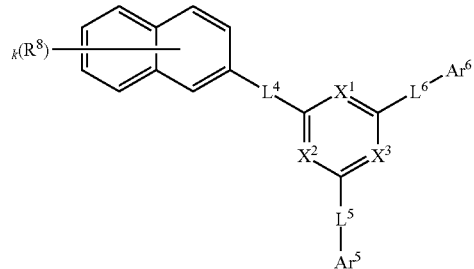

Formula 2-2

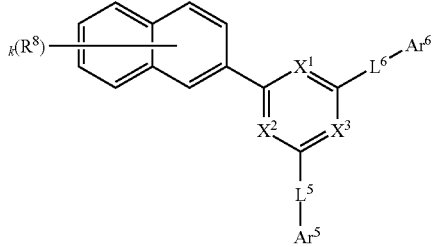

Formula 2-3

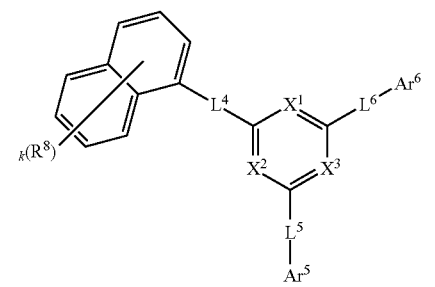

Formula 2-4

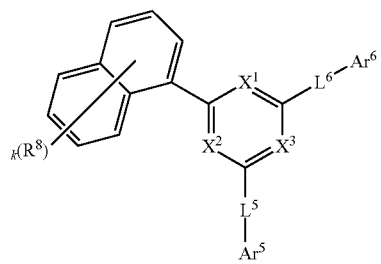

{In Formula 2-1 to Formula 2-4,

1) $Ar^5$, $Ar^6$, $X^1$, $X^2$, $X^3$, $L^4$, $L^5$ and $L^6$ are the same as defined in Formula 2, 2) $R^8$ is hydrogen; a $C_1$-$C_{20}$ alkyl group; a $C_6$-$C_{20}$ aryl group; a $C_6$-$C_{20}$ aryl group substituted by deuterium; a fluorenyl group; a $C_2$-$C_{60}$ heterocyclic group;

2) k is an integer of 0 to 7.}

The second host compound represented by Formula 2 is represented by any one of the following Formulas 2-5 to 2-8.

Formula 2-5

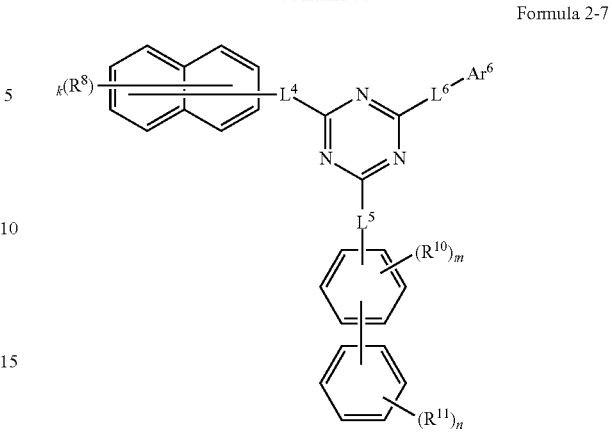

Formula 2-6

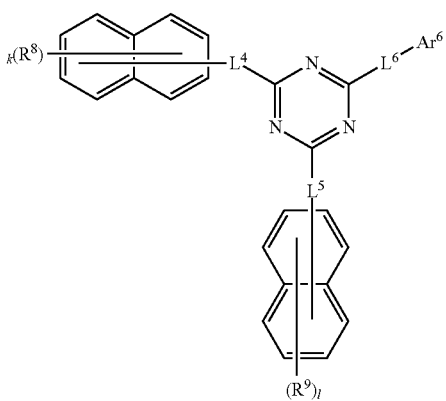

Formula 2-7

Formula 2-8

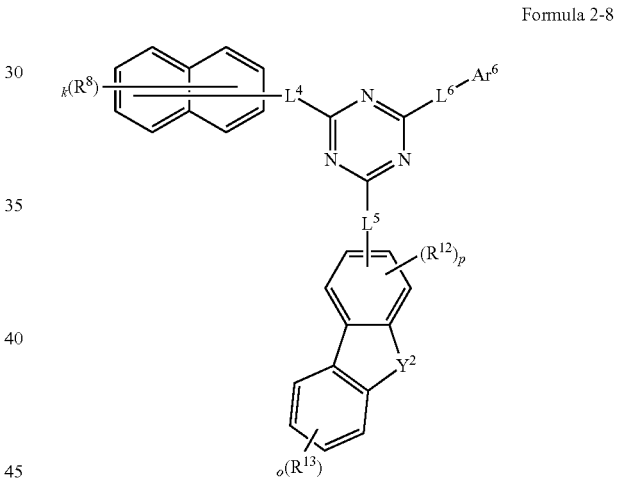

{In Formulas 2-5 to 2-8,

1) $Ar^5$, $Ar^6$, $L^4$, $L^5$ and $L^6$ are the same as defined in Formula 2,

2) $R^8$ is hydrogen; a $C_1$-$C_{20}$ alkyl group; a $C_6$-$C_{20}$ aryl group; a $C_6$-$C_{20}$ aryl group substituted by deuterium; a fluorenyl group; a $C_2$-$C_{60}$ heterocyclic group;

3) $R^9$, $R^{10}$, $R^{11}$, $R^{12}$ and $R^{13}$ are the same as definition of $R^1$ in Formula 1, 4) $Y^2$ is $CR^{14}R^{15}$, N—$Ar^7$, O or S, 5) wherein $R^{14}$ and $R^{15}$ are the same as definition of $R^1$ in Formula 1, 6) $Ar^7$ is the same as definition of $Ar^1$ in Formula 1, 7) k and l are each independently an integer of 0 to 7, m and o are each independently an integer of 0 to 4, n is an integer of 0 to 5, and p is an integer of 0 to 3.}

Specifically, the compound represented by Formula 2 may be any one of the following compounds.

N-1 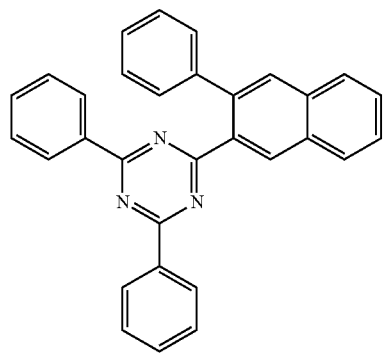
N-2 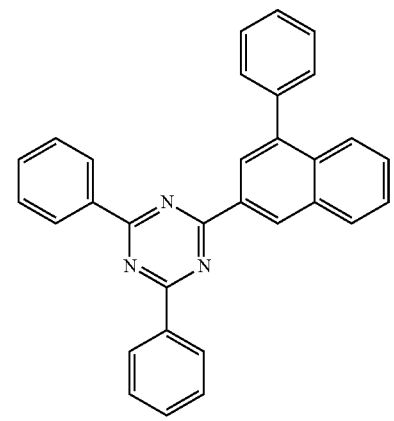
N-3 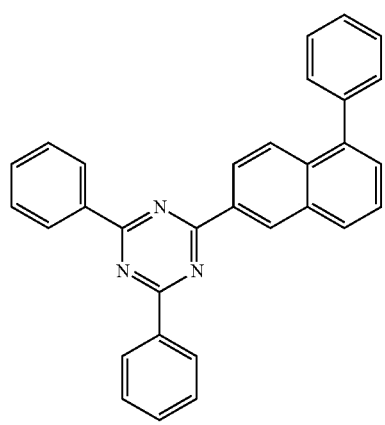
N-4 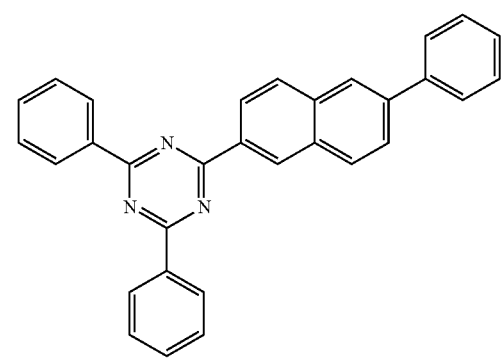
N-5 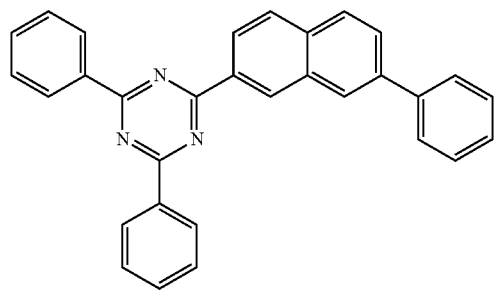
N-6 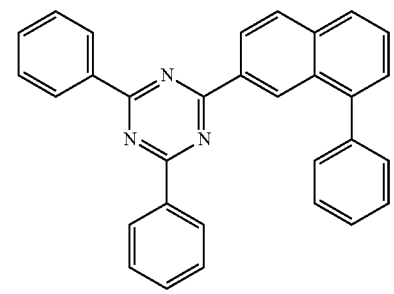
N-7 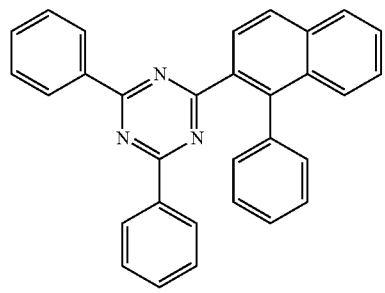
N-8 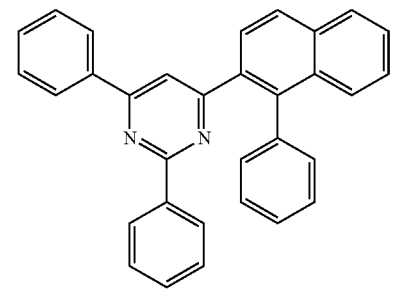

-continued
N-9
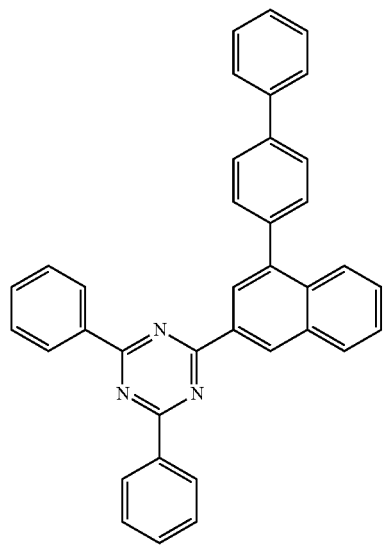
N-10
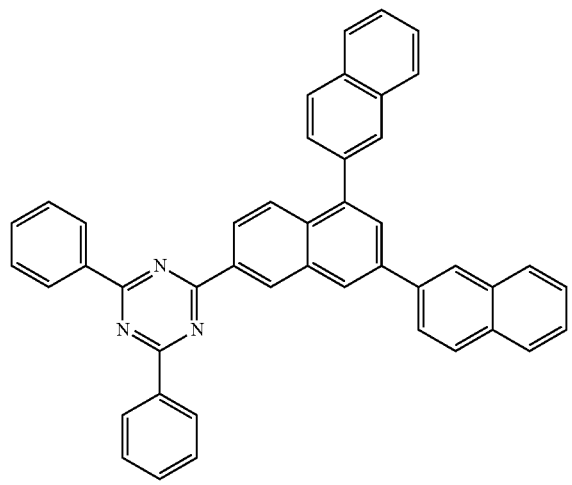
N-11
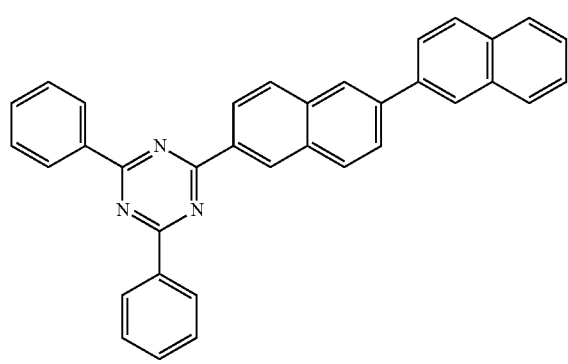
N-12
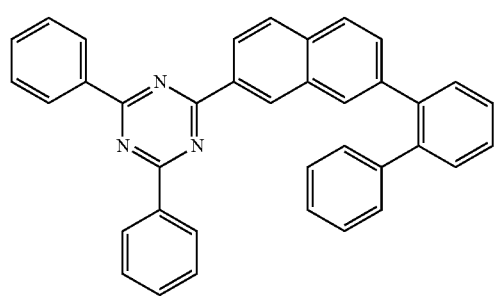
N-13
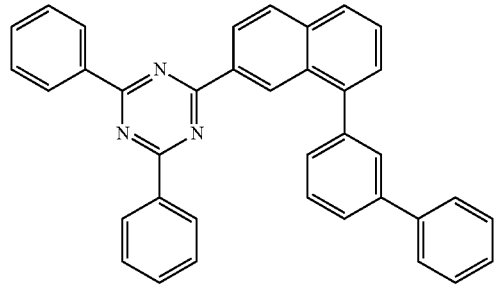
N-14
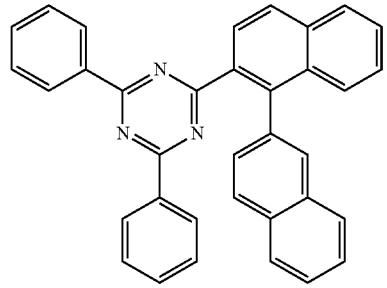
N-15
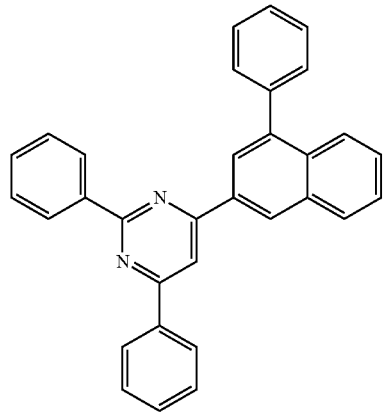
N-16
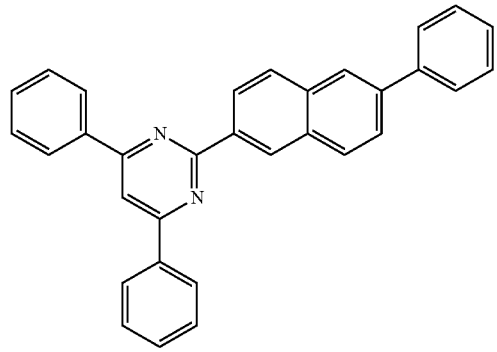

N-17
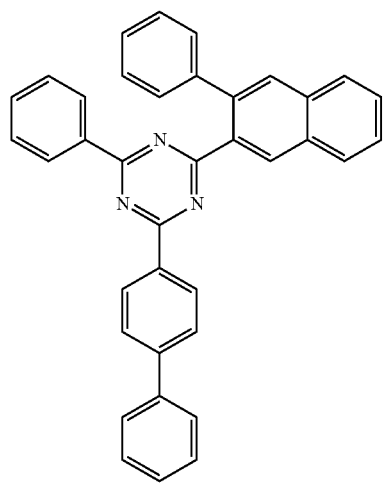
N-18
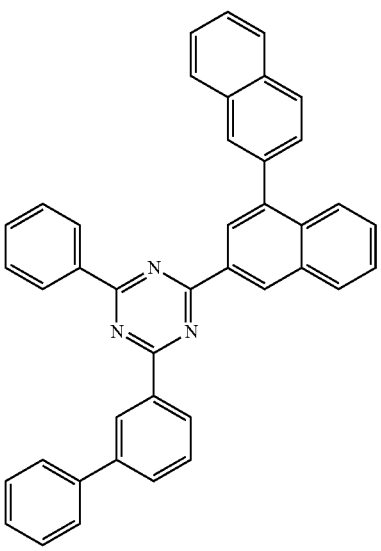
N-19
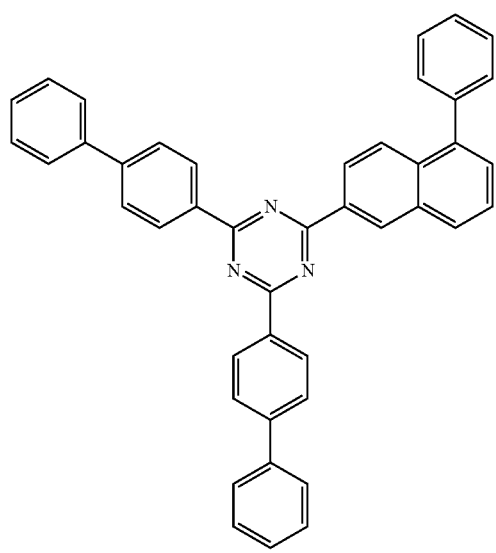
N-20
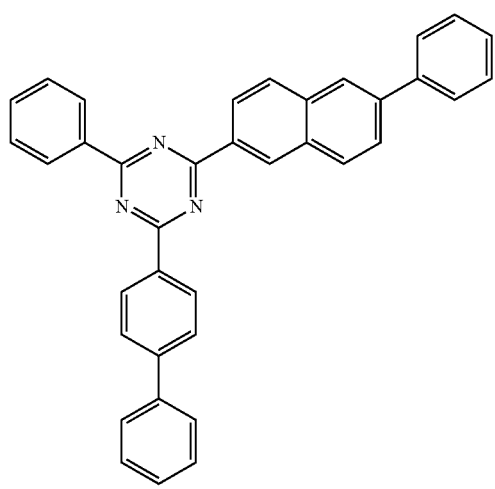
N-21
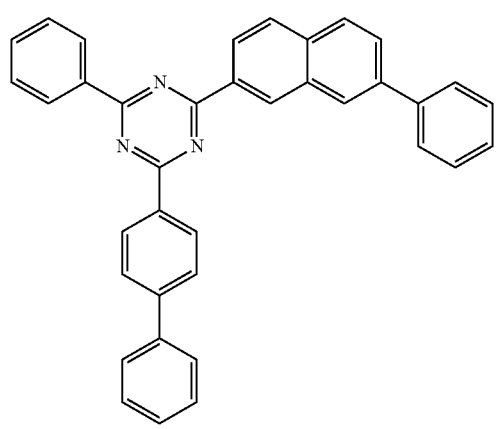
N-22
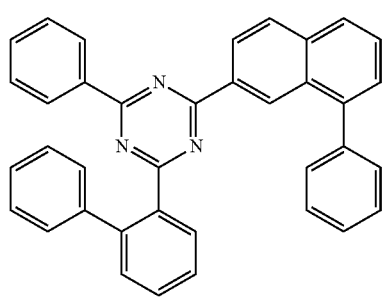

-continued
N-23
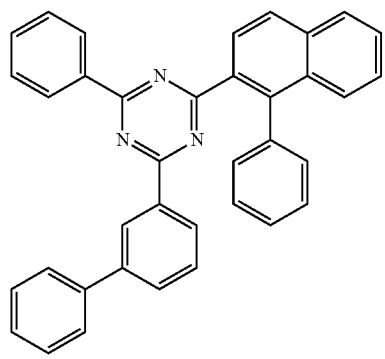
N-24
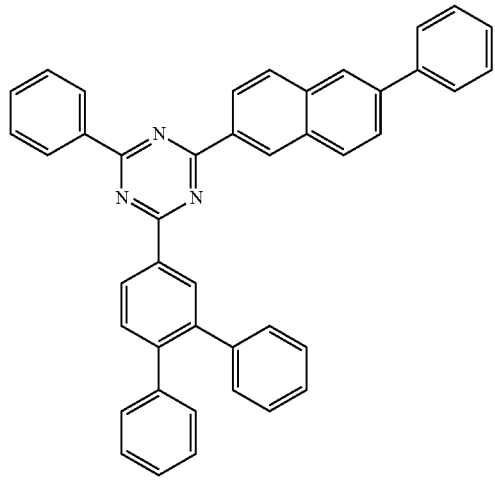
N-25
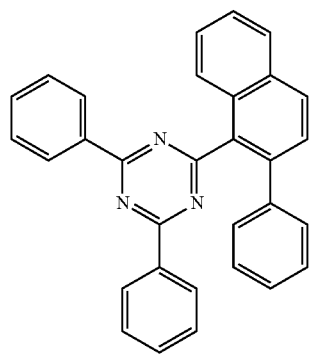
N-26
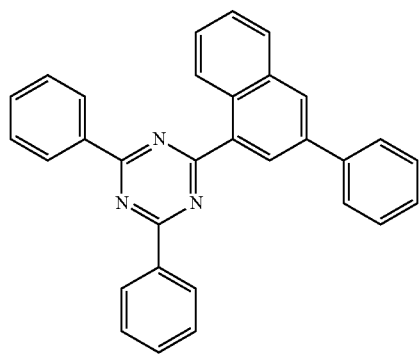
N-27
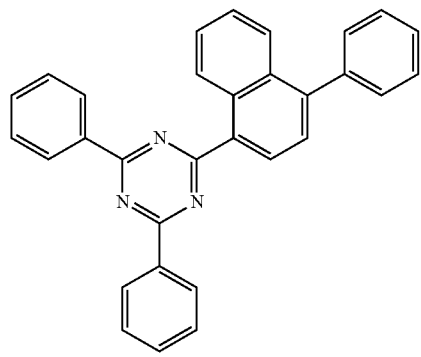
N-28
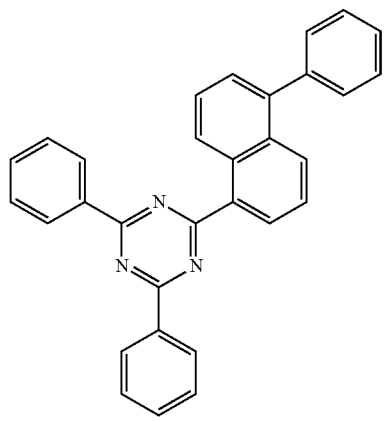

-continued
N-29
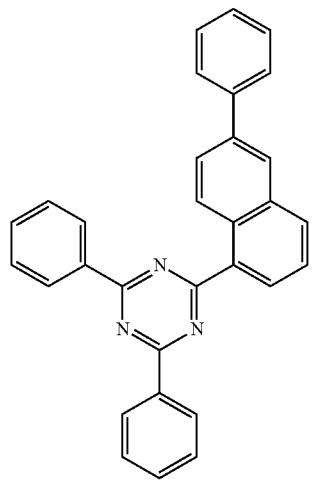
N-30
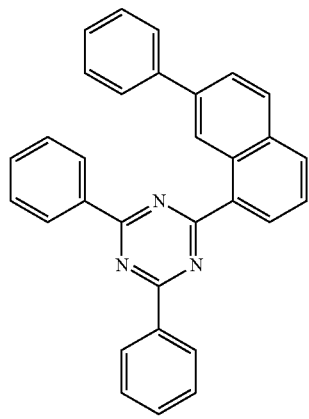
N-31
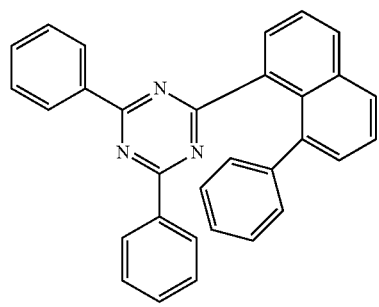
N-32
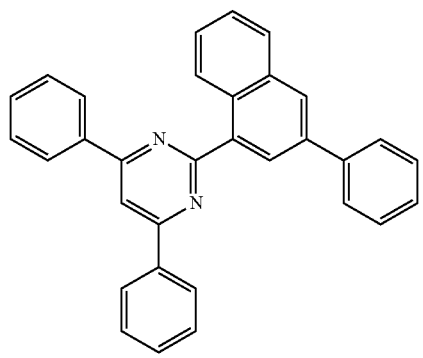
N-33
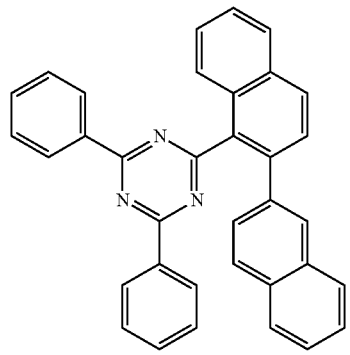
N-34
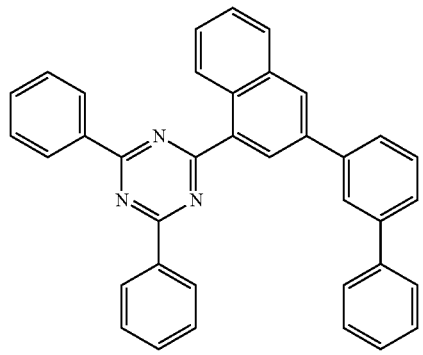

-continued
N-35
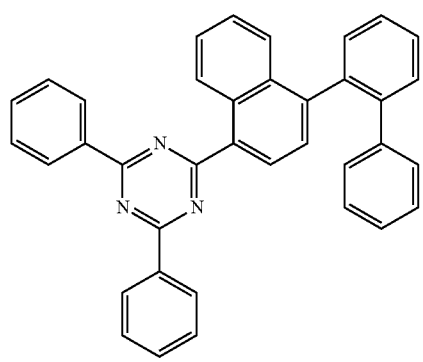
N-36
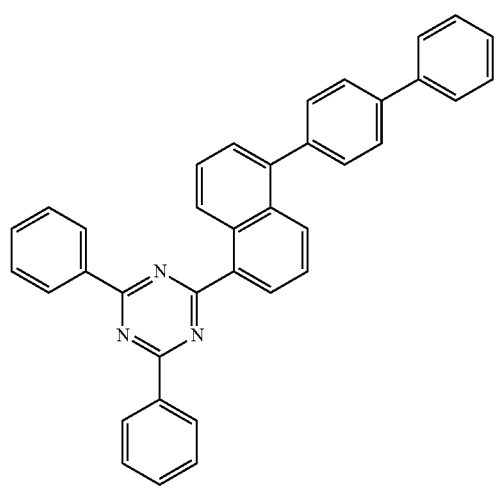
N-37
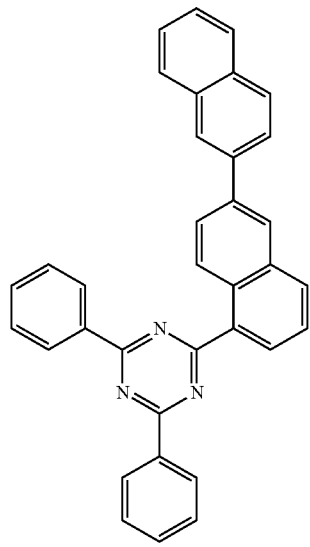
N-38
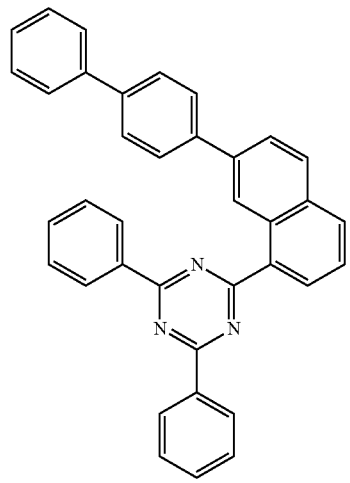
N-39
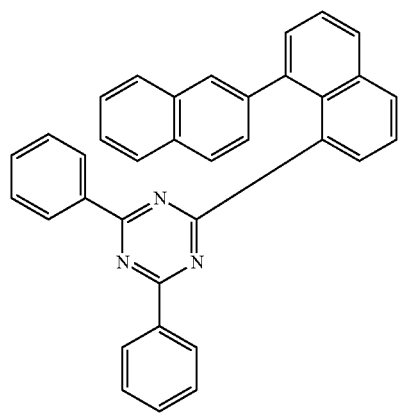
N-40
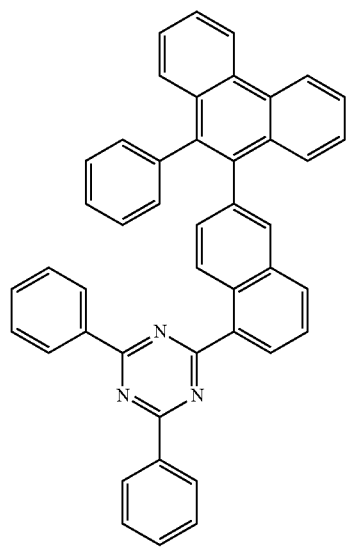

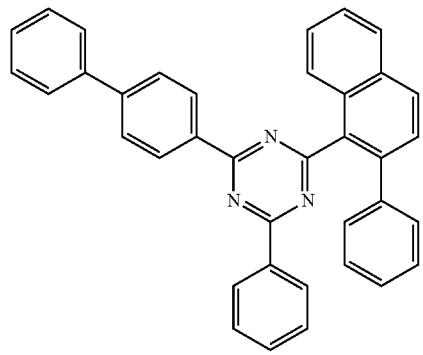
N-41
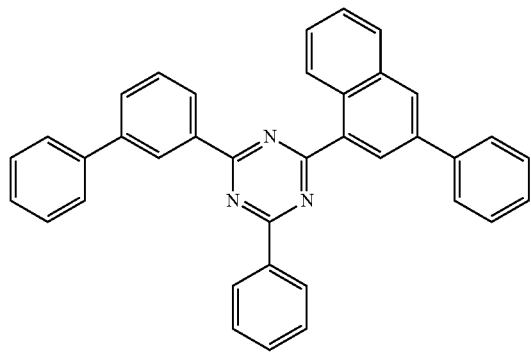
N-42
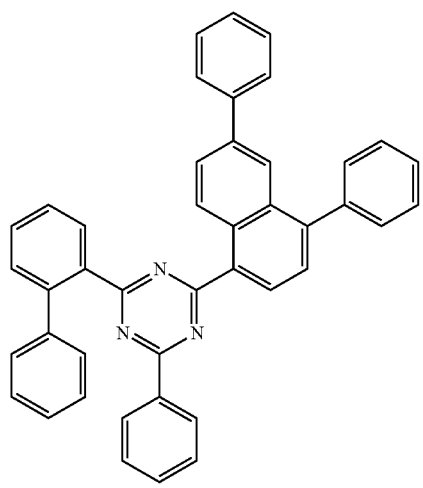
N-43
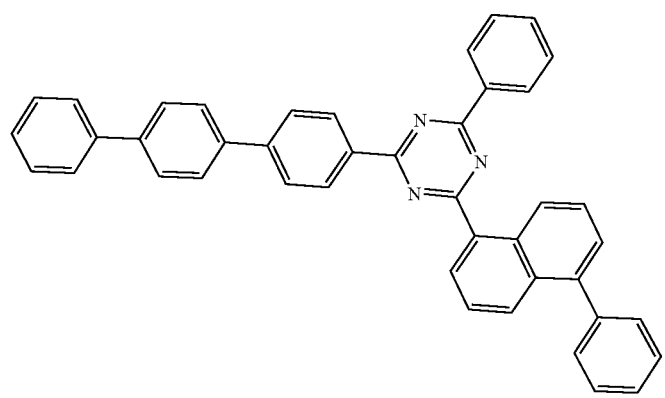
N-44

-continued
N-45
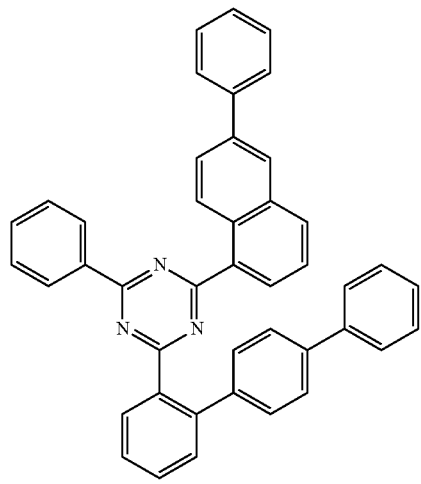
N-46
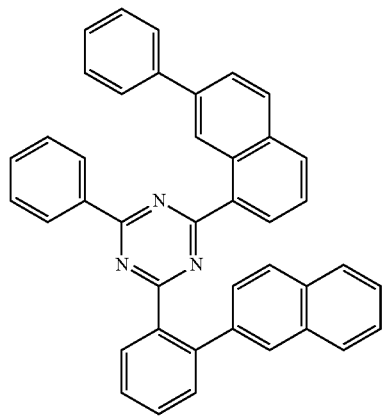
N-47
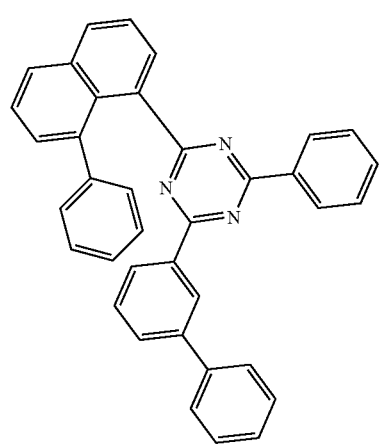
N-48
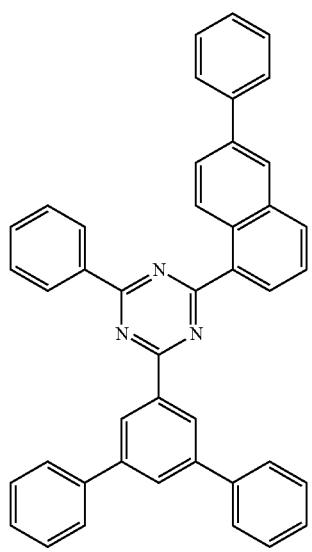
N-49
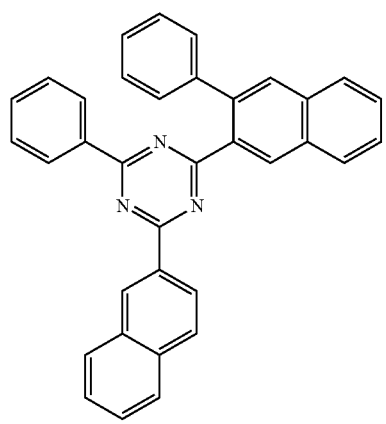
N-50
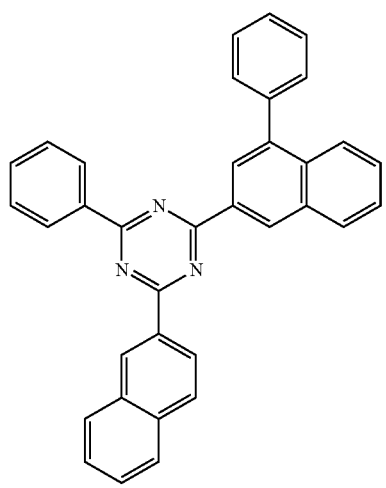

-continued
N-51
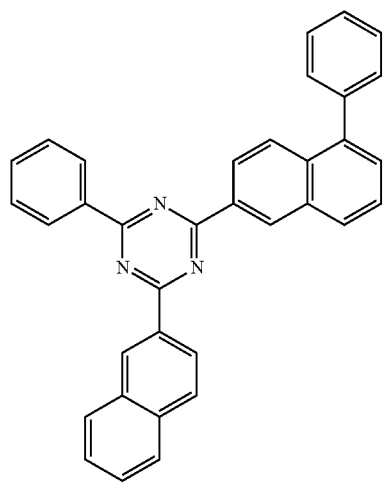
N-52
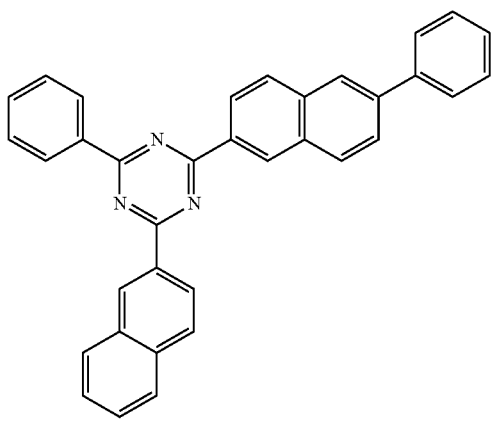
N-53
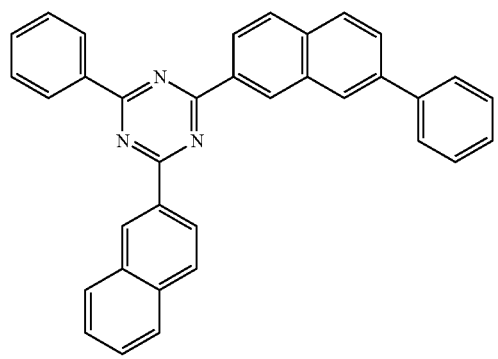
N-54
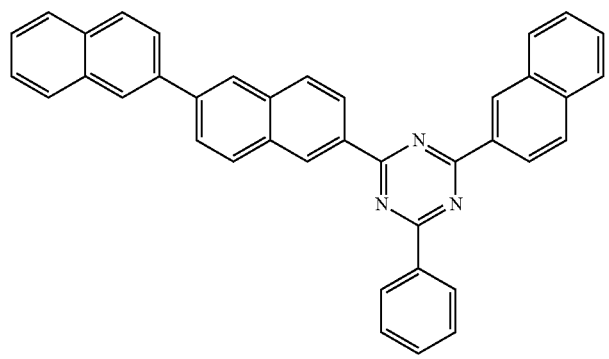
N-55
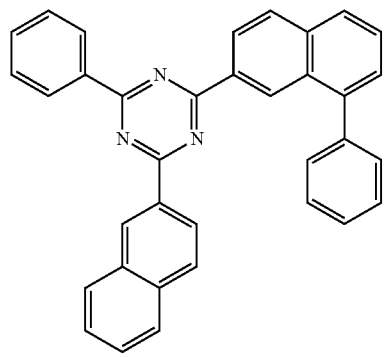
N-56

-continued
N-57
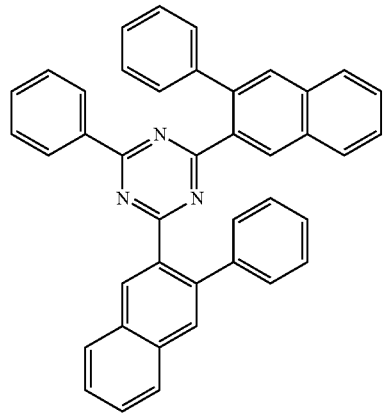
N-58
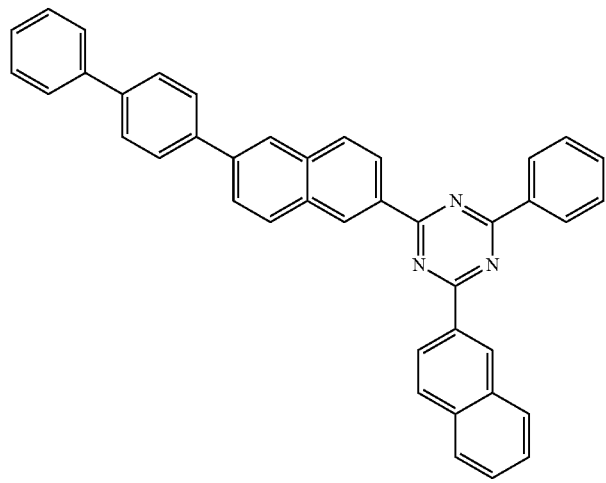
N-59
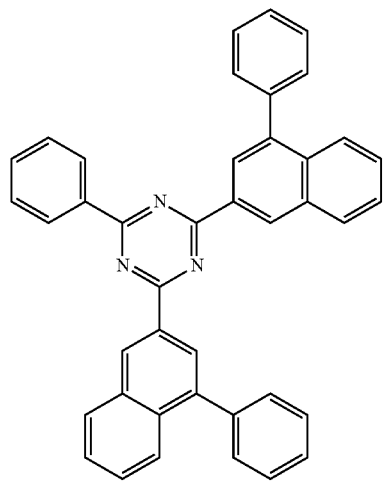
N-60
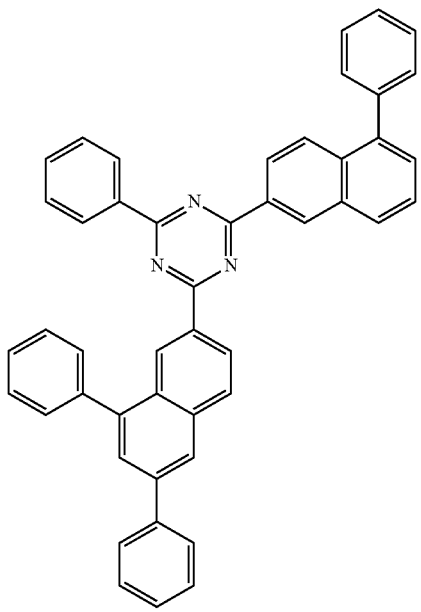

-continued
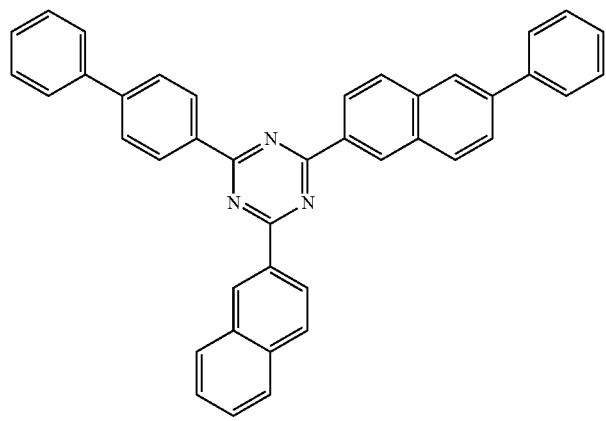
N-61
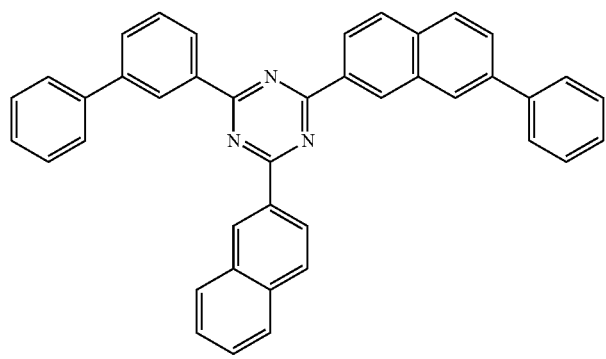
N-62
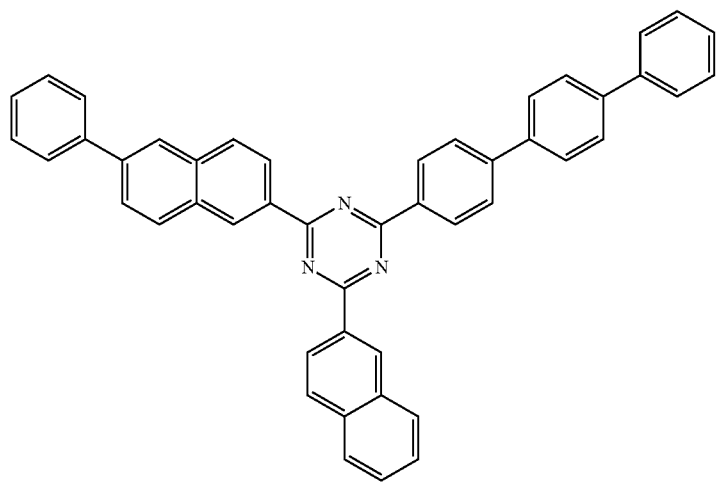
N-63

-continued
N-64
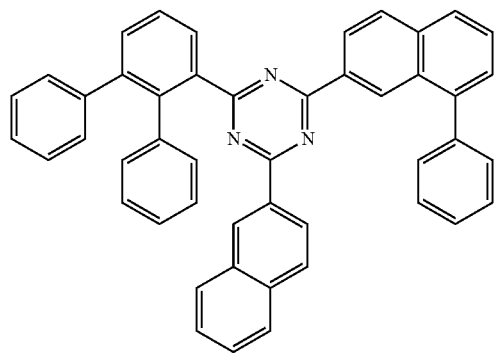
N-65
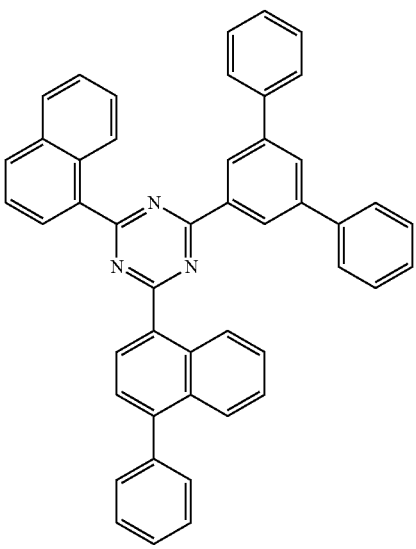
N-66
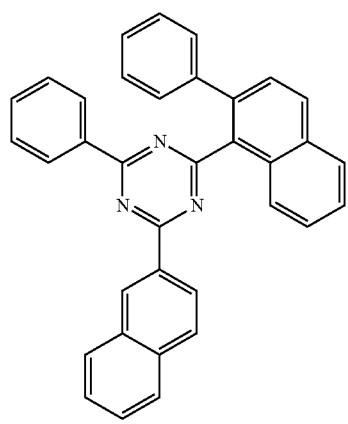
N-67
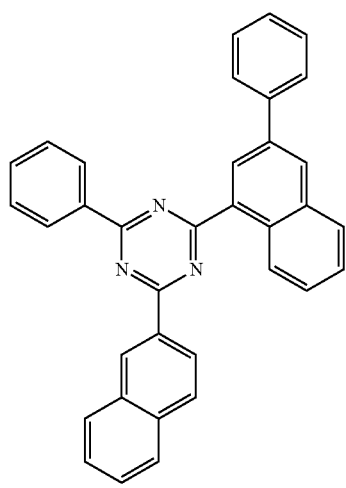
N-68
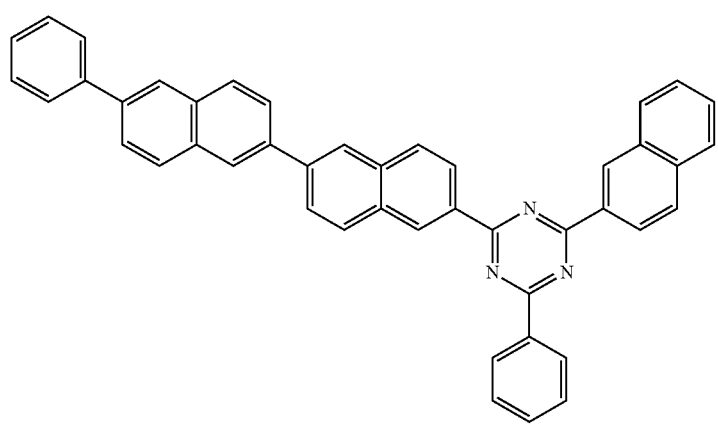

N-69
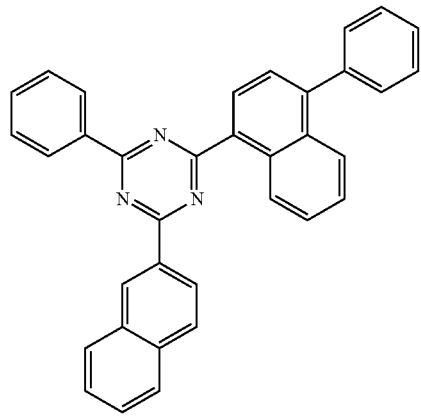
N-70
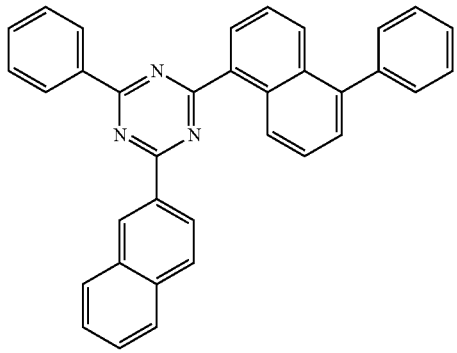
N-71
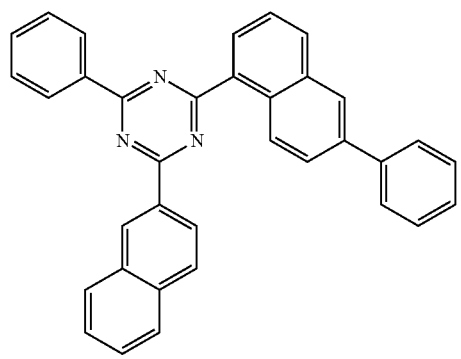
N-72
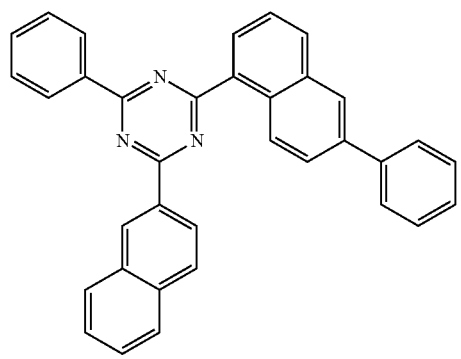
N-73
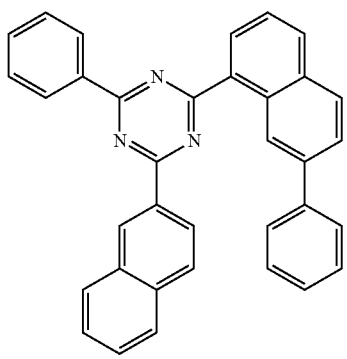
N-74
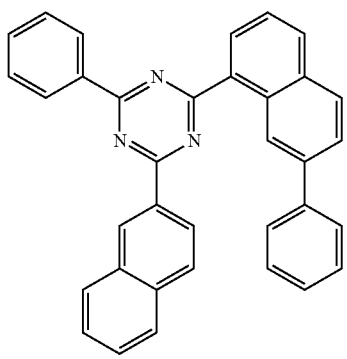

-continued
N-75
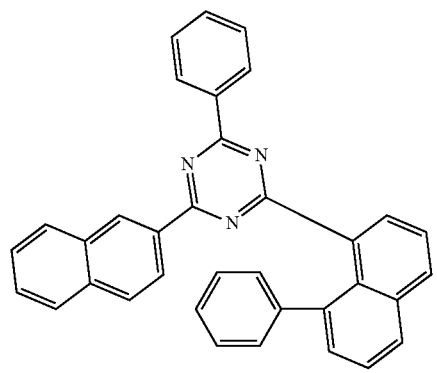
N-76
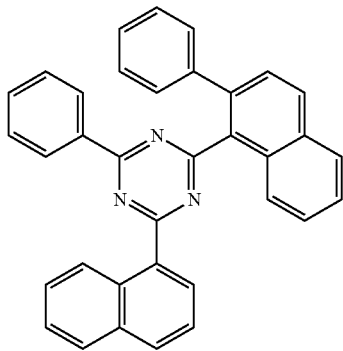
N-77
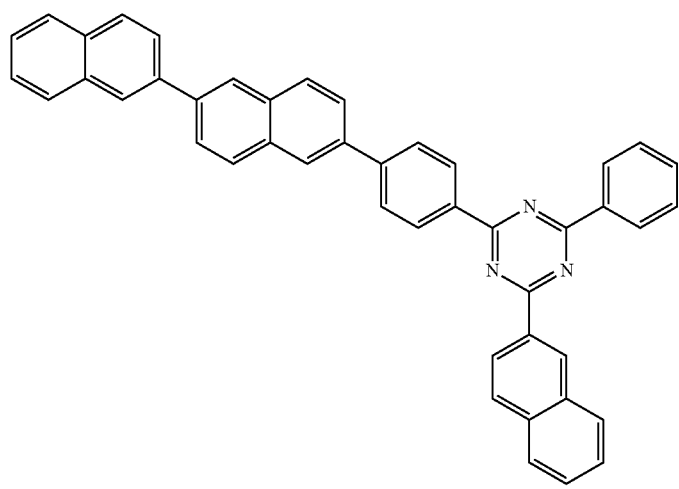
N-78
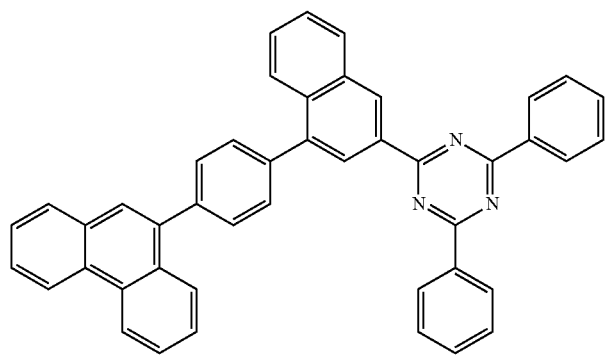
N-79
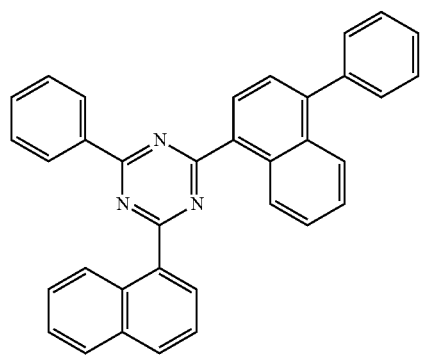
N-80
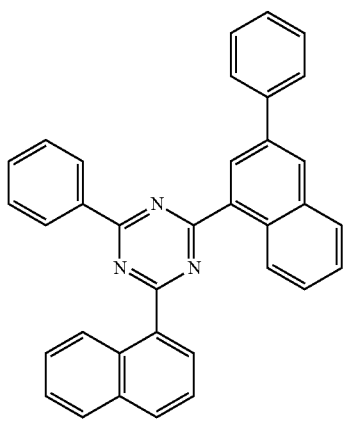

-continued
N-81
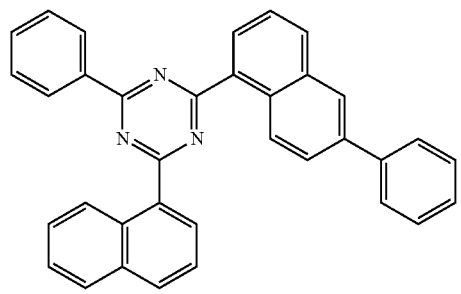
N-82
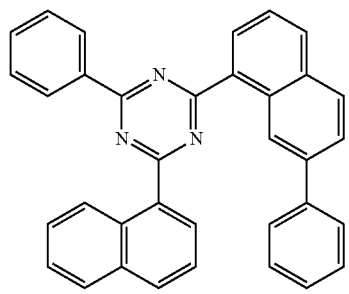
N-83
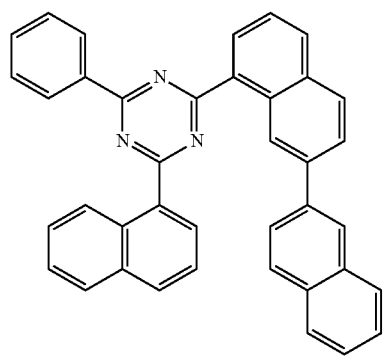
N-84
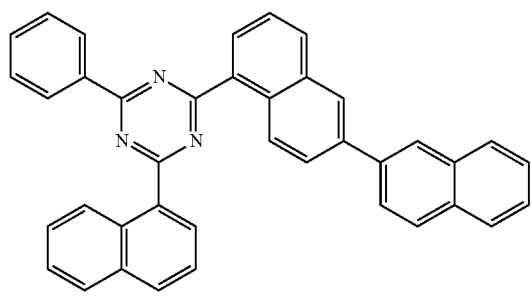
N-85
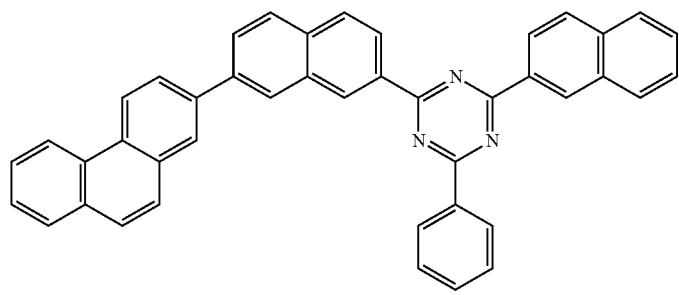
N-86
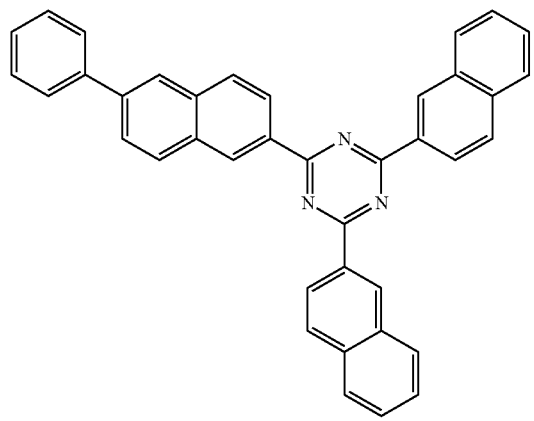

-continued
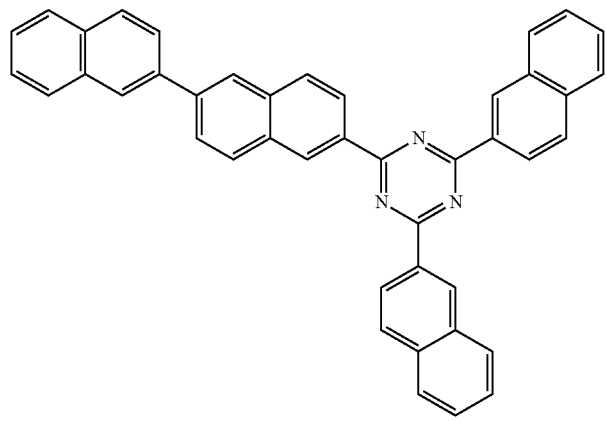
N-87
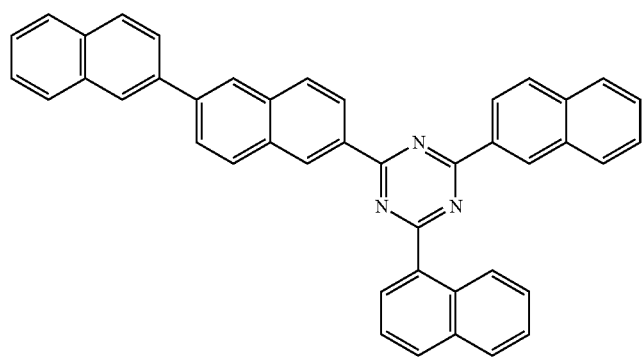
N-88
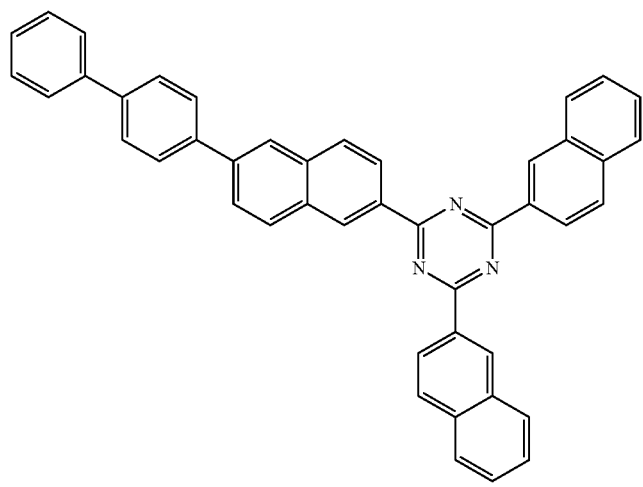
N-89
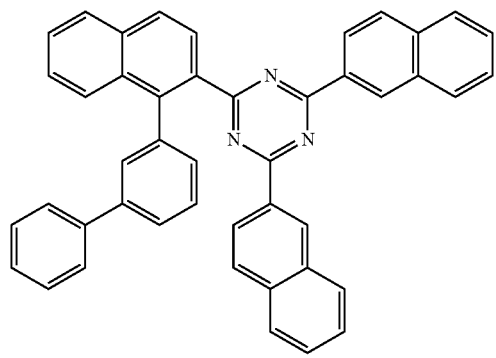
N-90

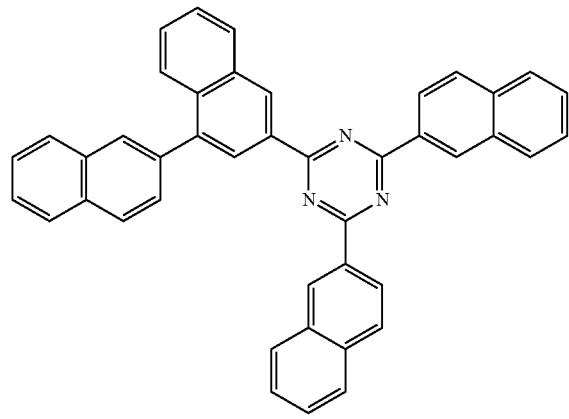
N-91
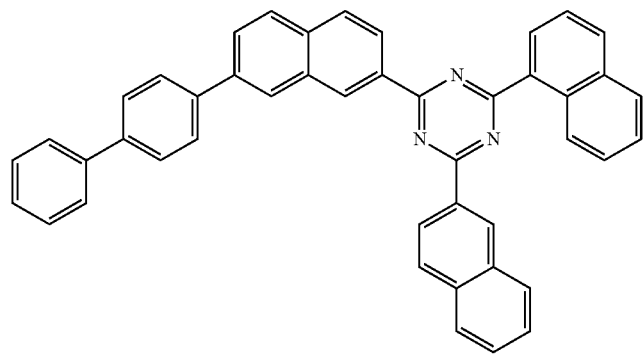
N-92
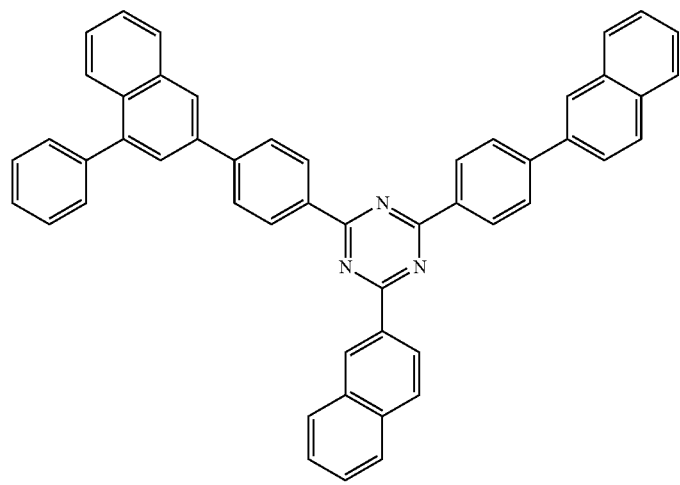
N-93
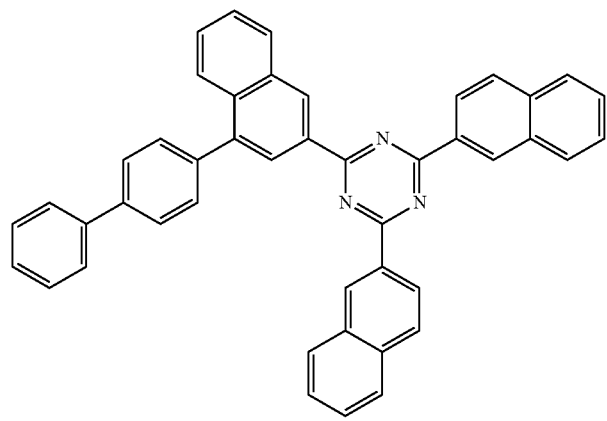
N-94

-continued
N-95
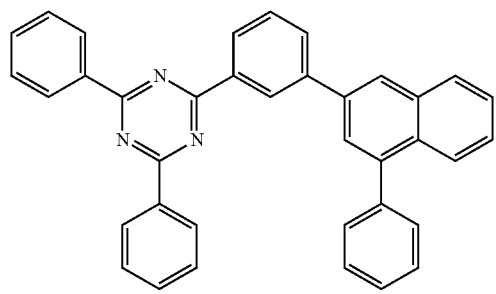
N-96
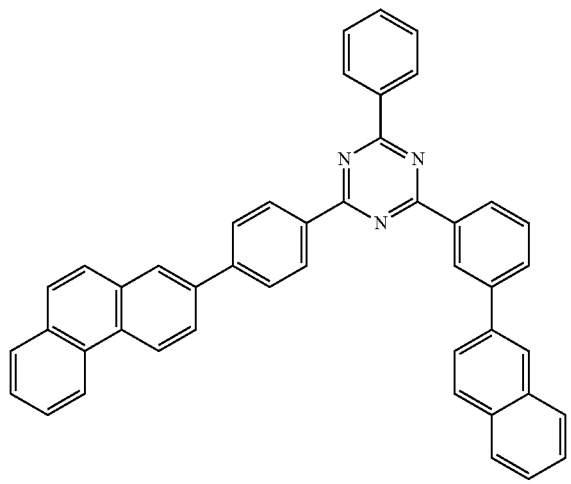
N-97
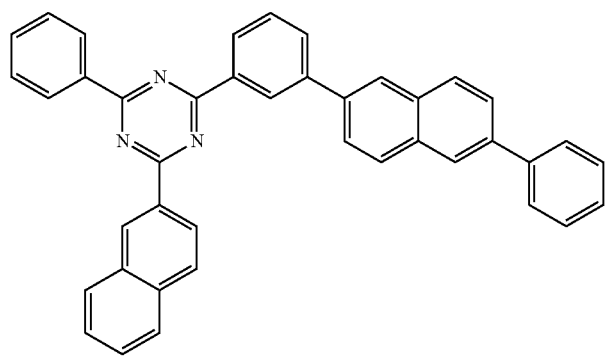
N-98
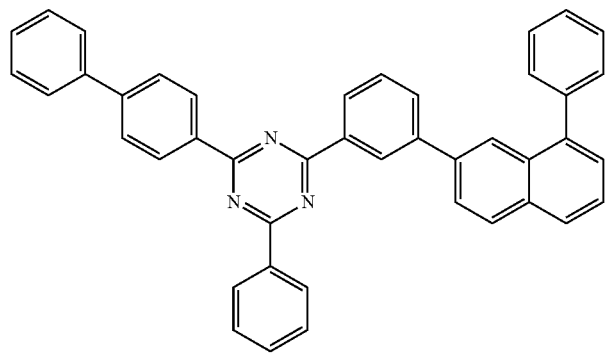
N-99
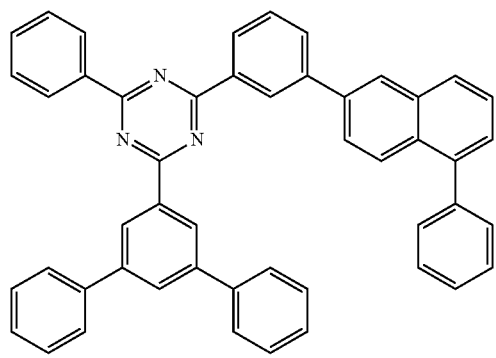

N-100
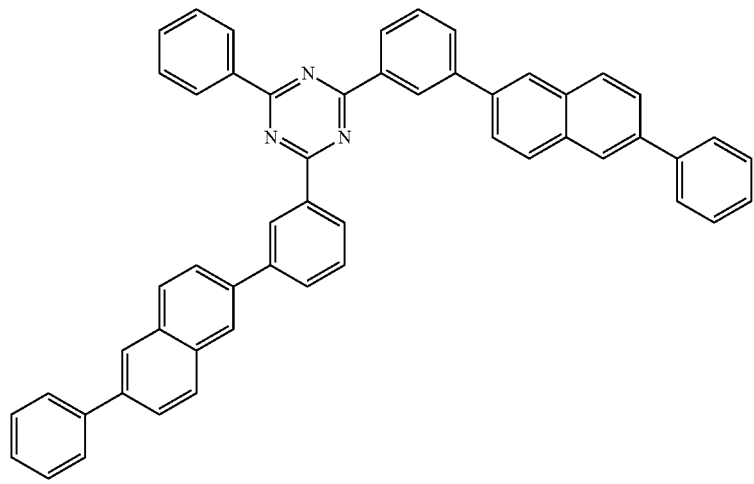
N-101
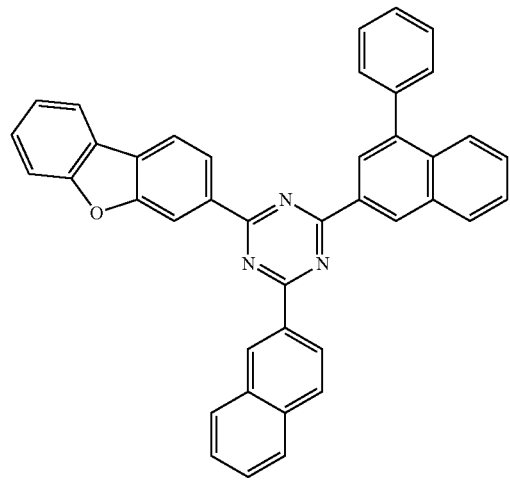
N-102
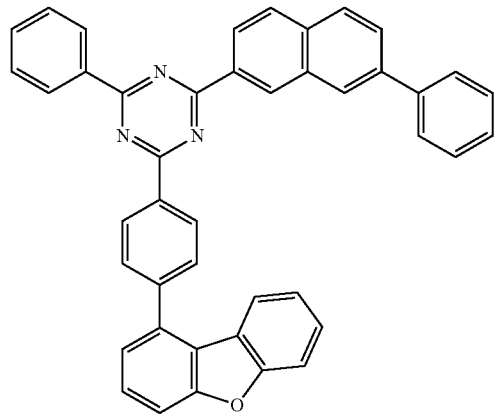
N-103
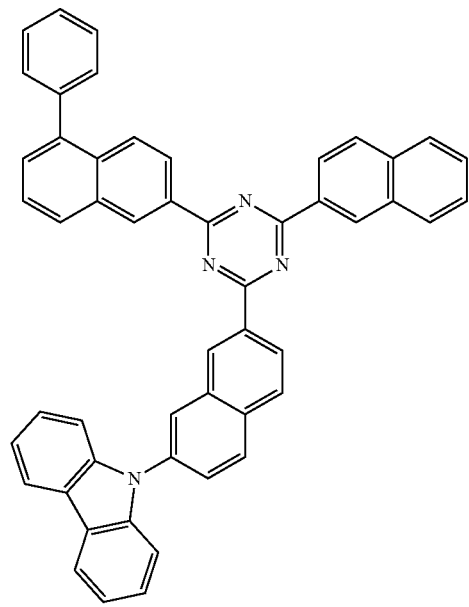
N-104
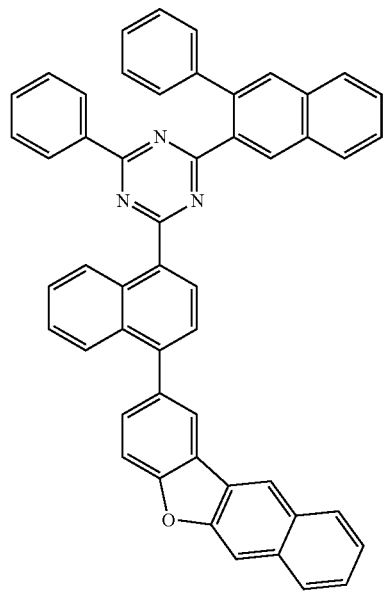

N-105
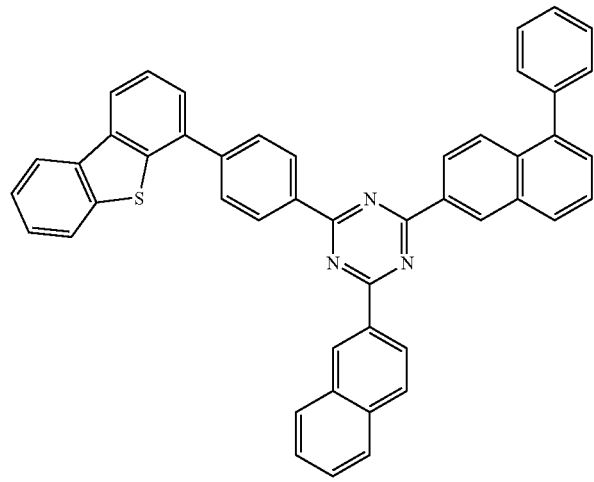
N-106
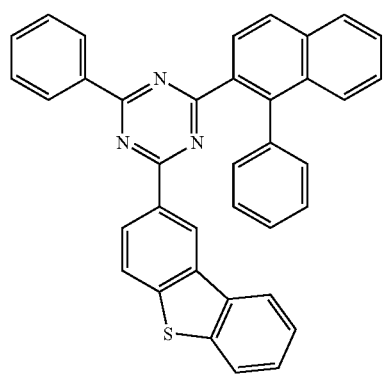
N-107
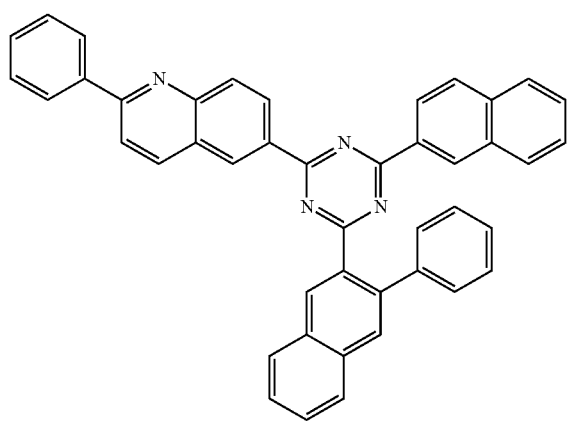
N-108
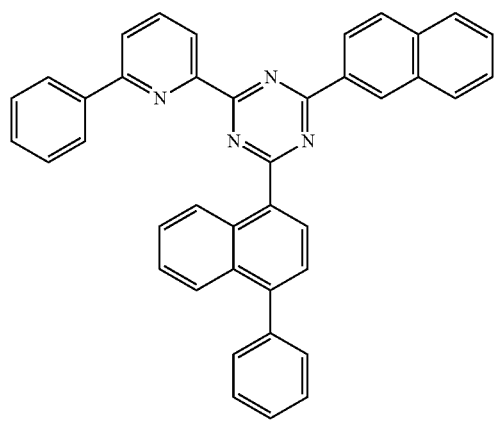

N-109
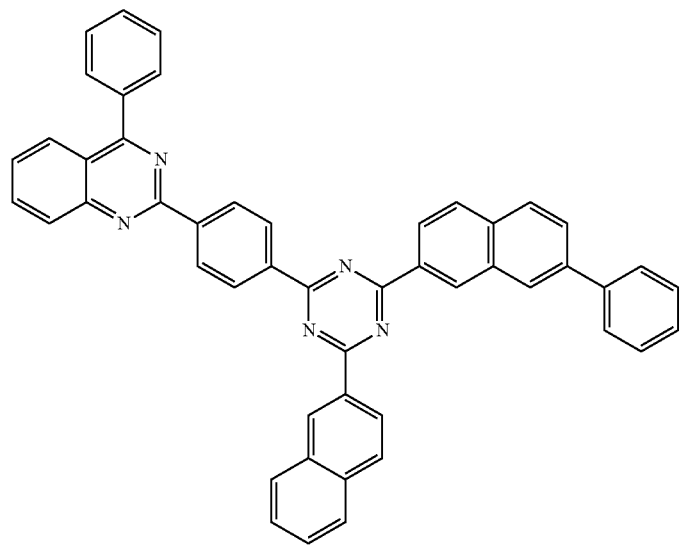
N-110
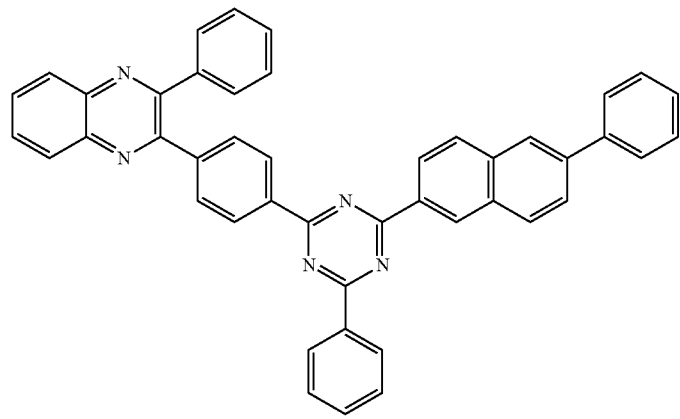
N-111
N-112
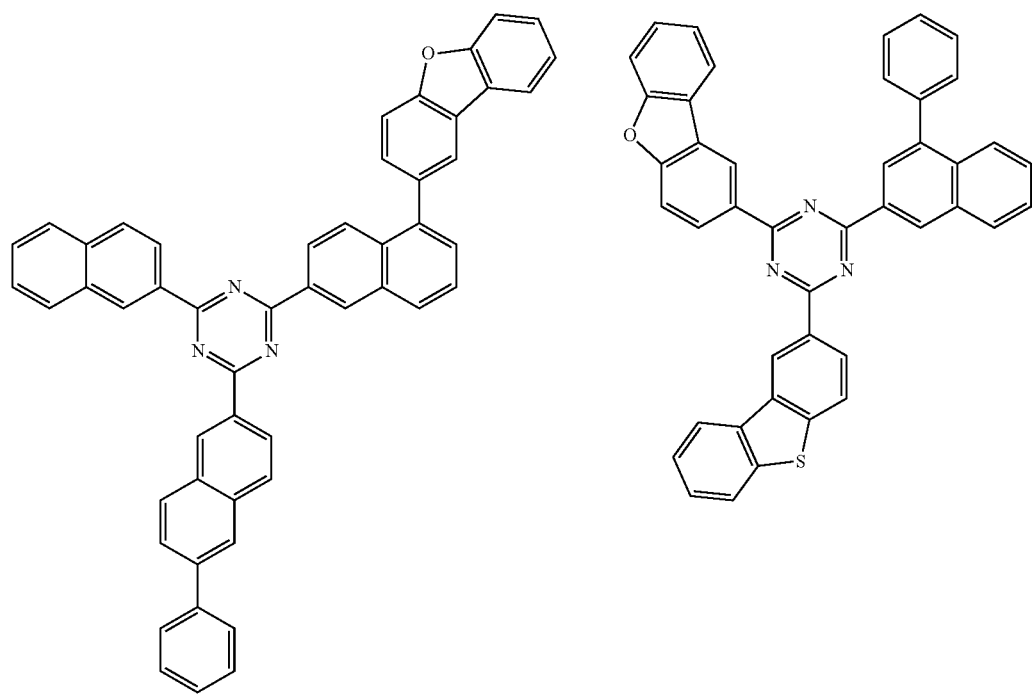

101
N-113
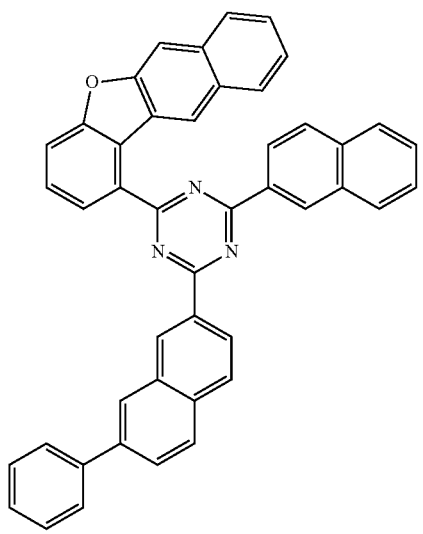
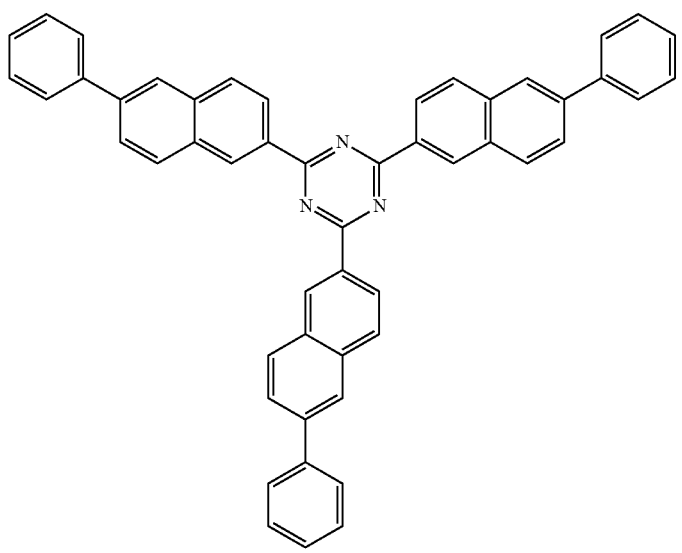
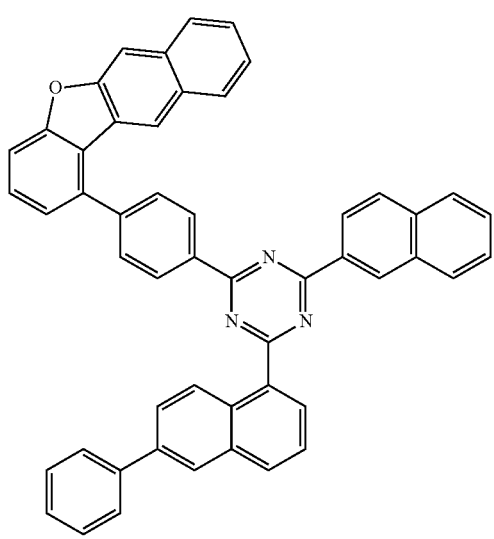
102
-continued
N-114
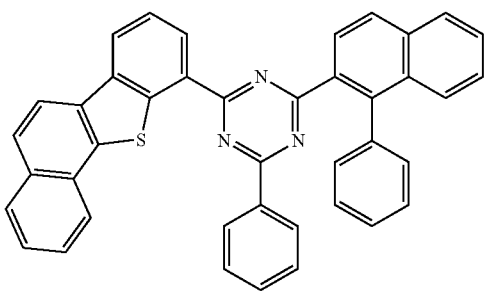
N-115
N-116

N-117
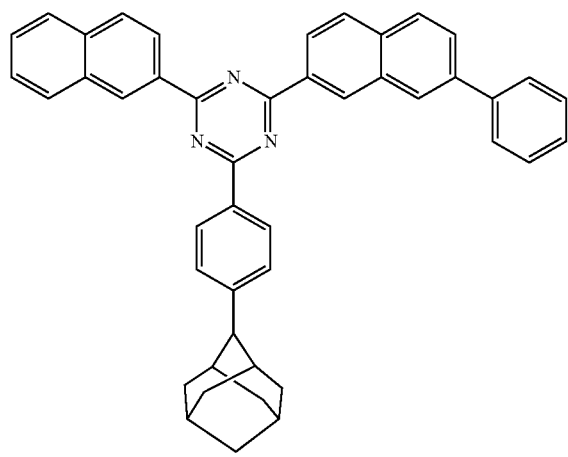
N-118
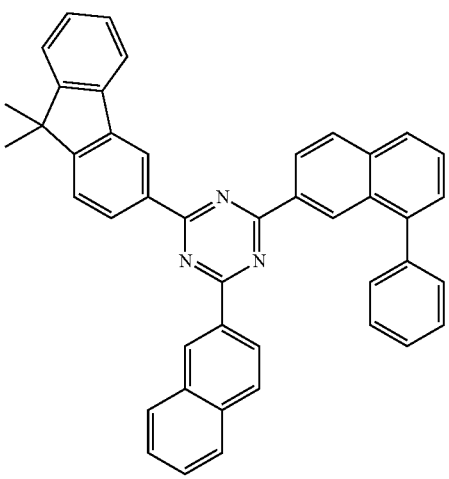
N-119
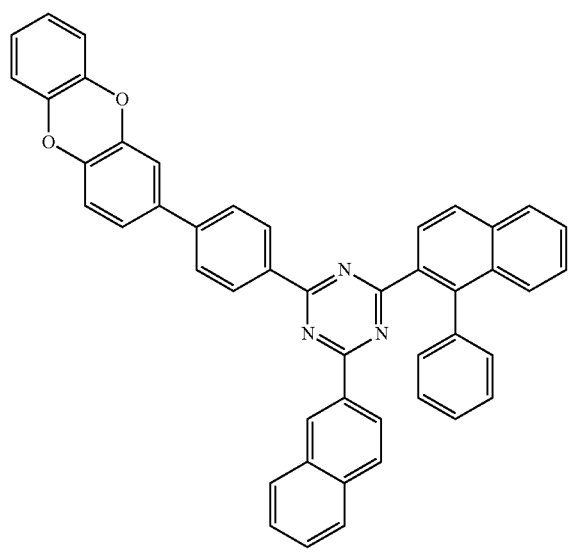
N-120
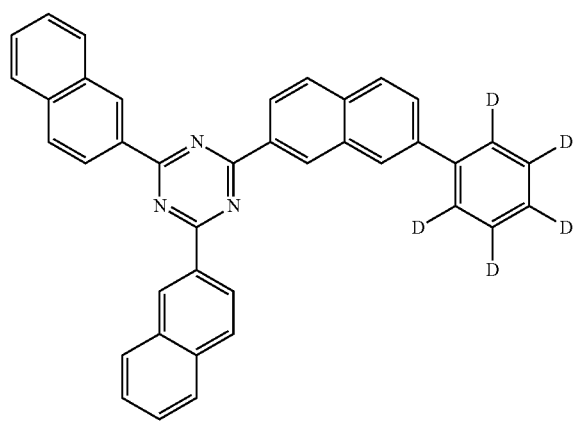

-continued
N-121
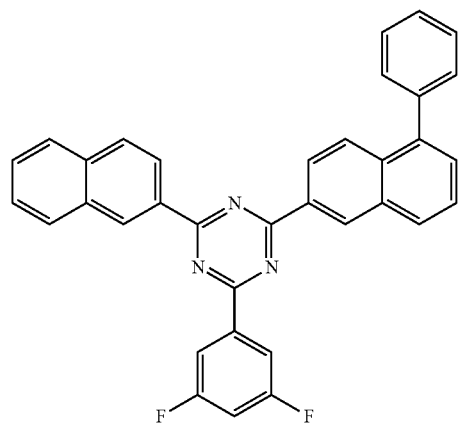
N-122
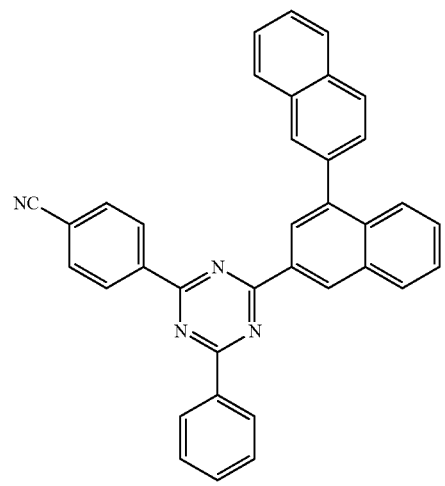
N-123
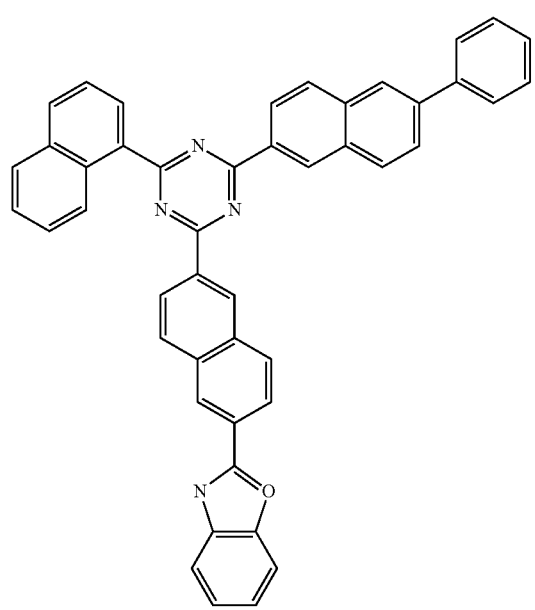
N-124
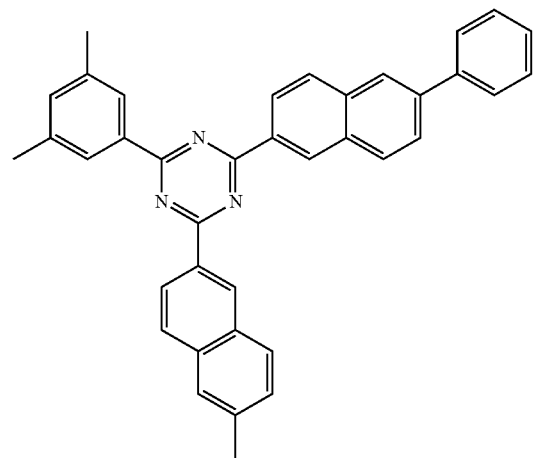
N-125
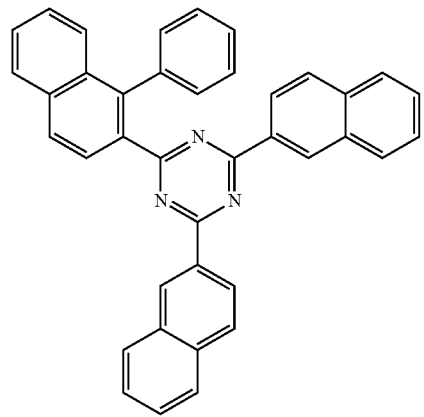
N-126
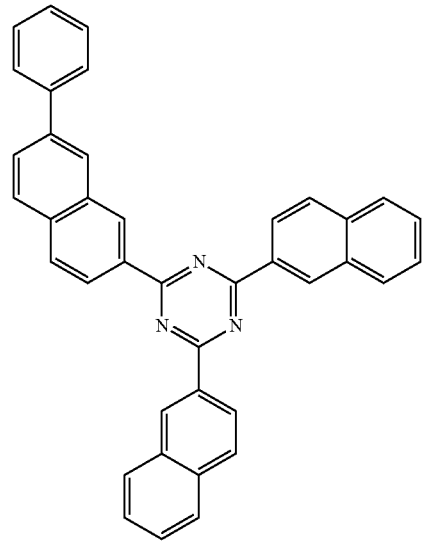

-continued
N-127
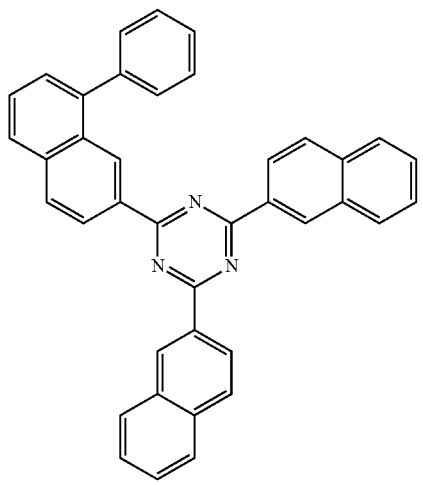
N-128
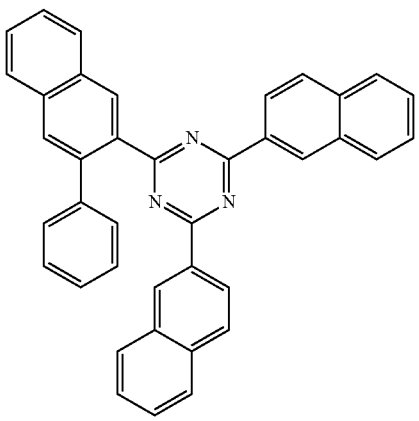
N-129
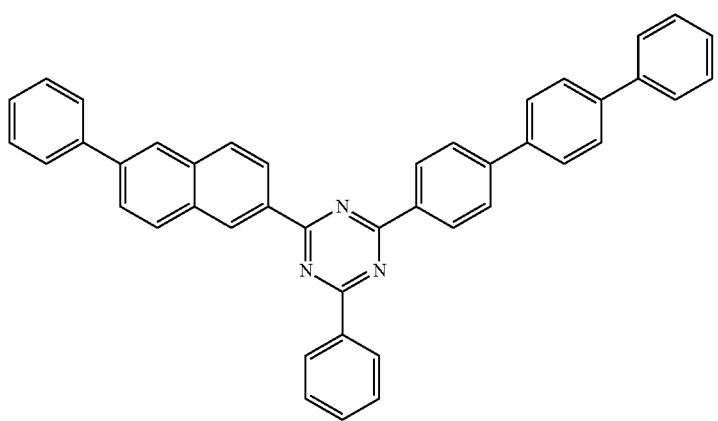
N-130
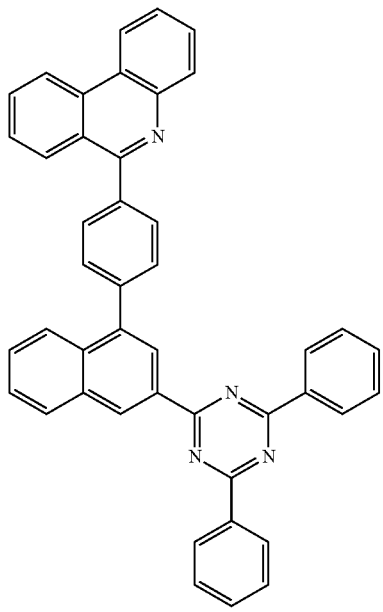

N-131
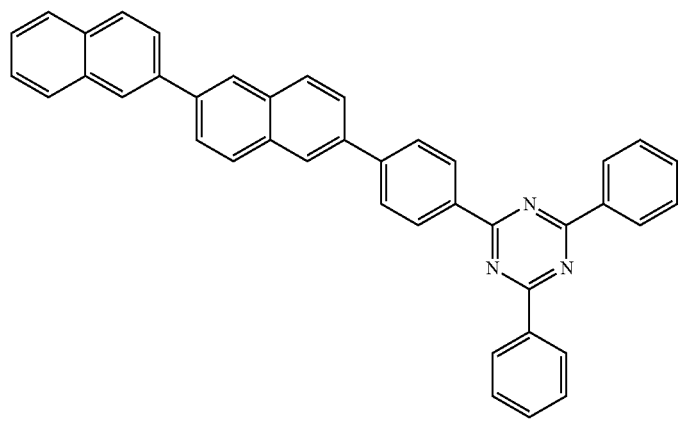
N-132
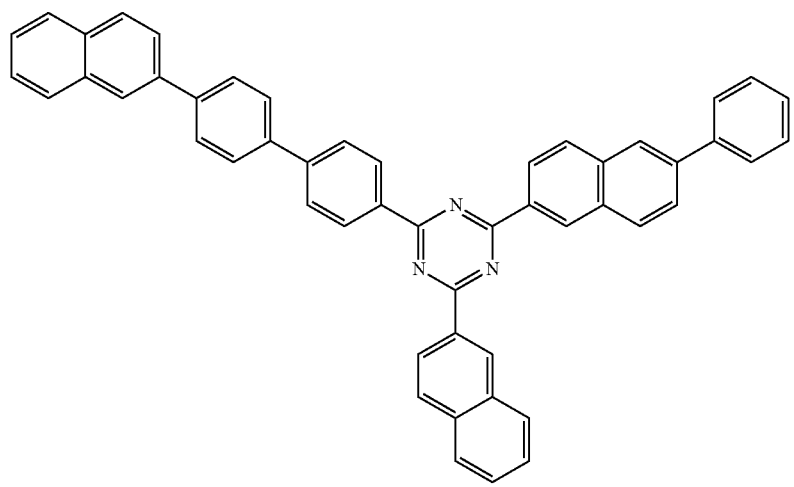
N-133
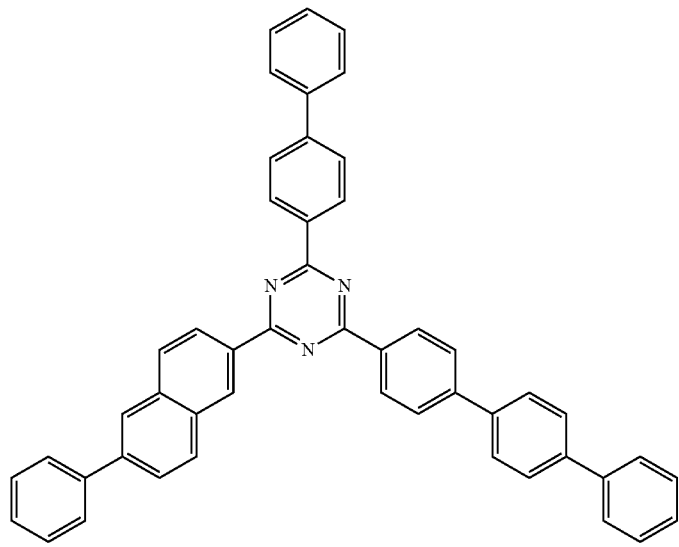

N-134
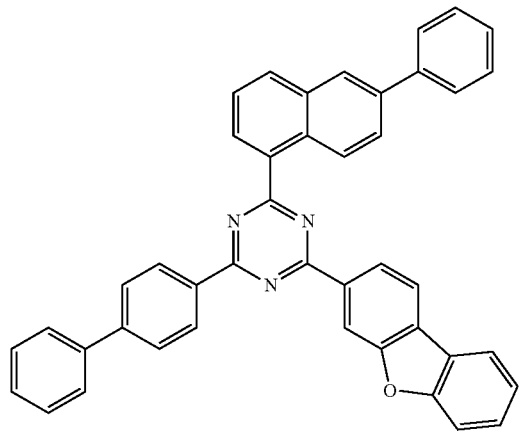
N-135
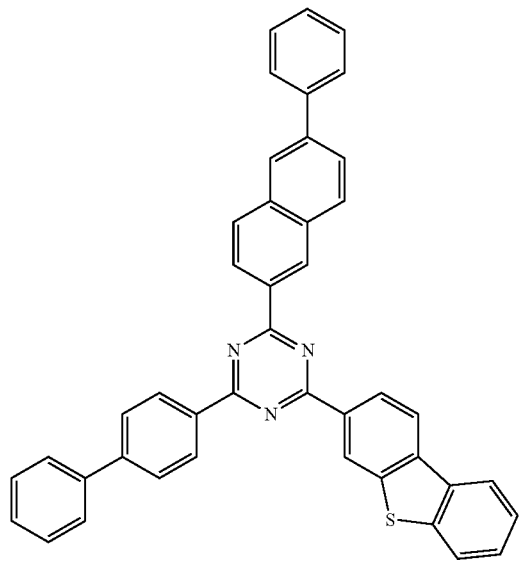
N-136
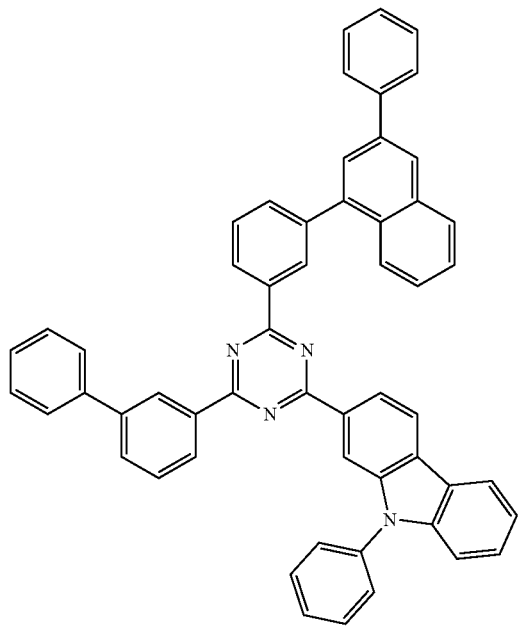
N-137
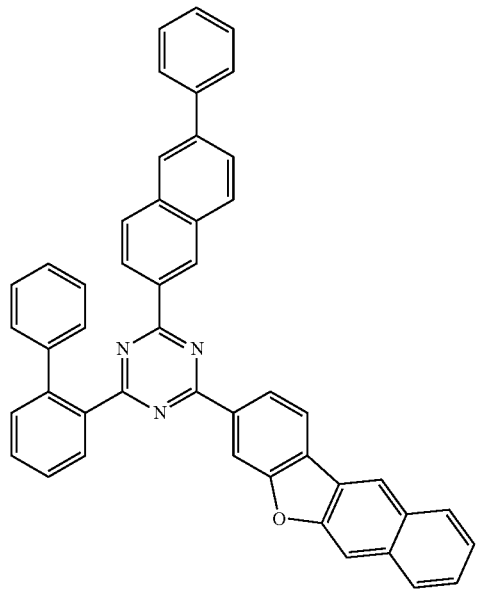
N-138
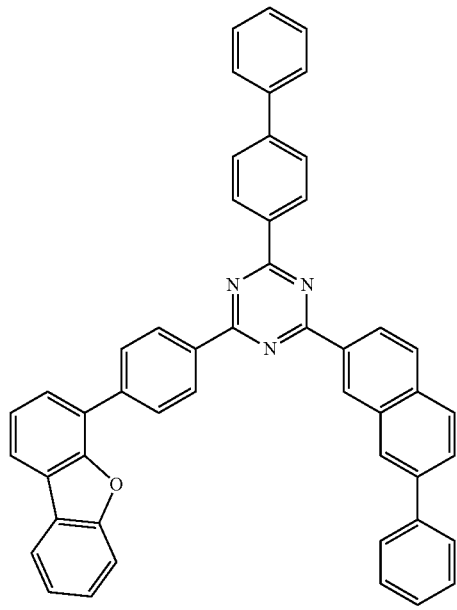

N-139
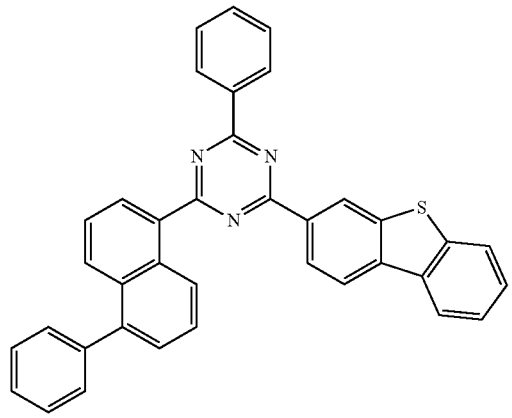
N-140
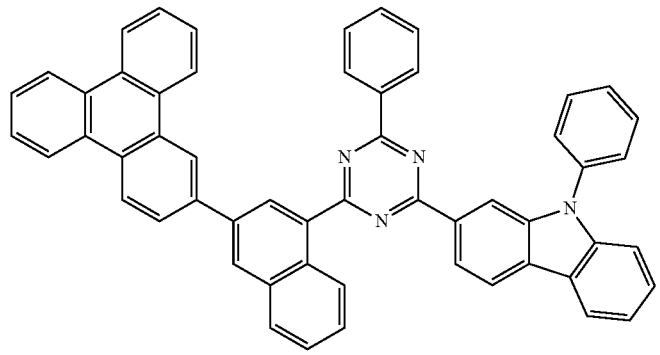
N-141
N-142
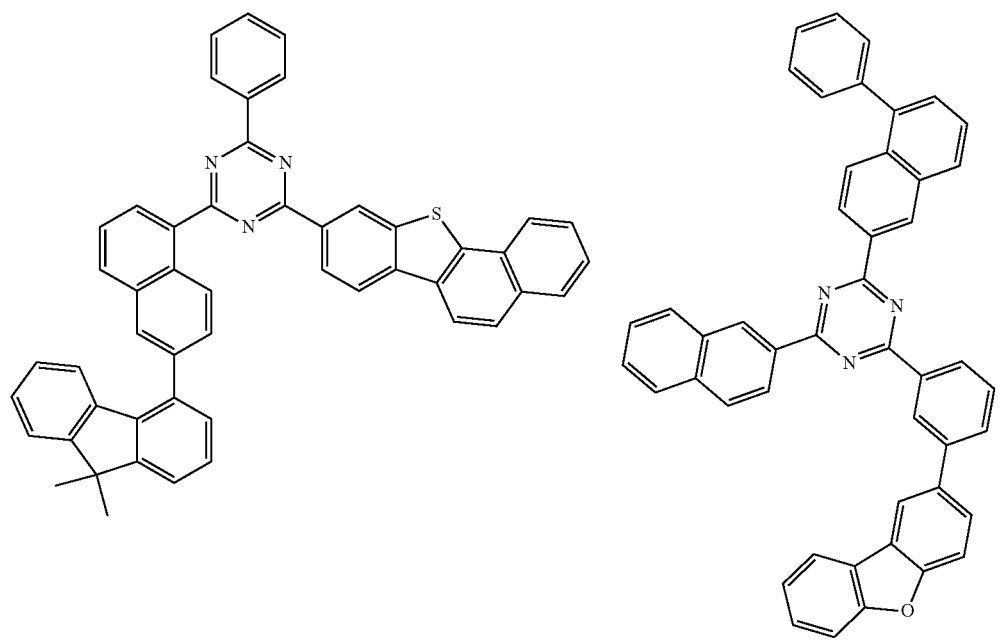

-continued
N-143
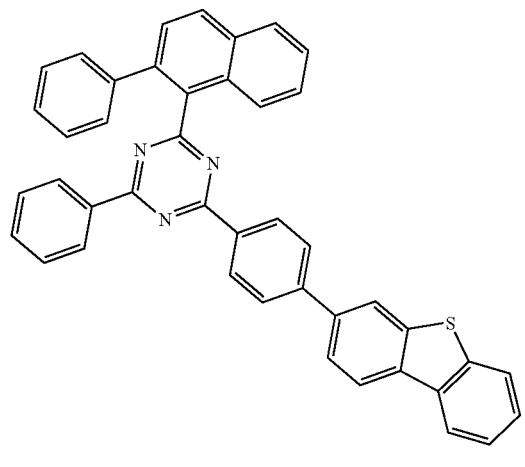
N-144
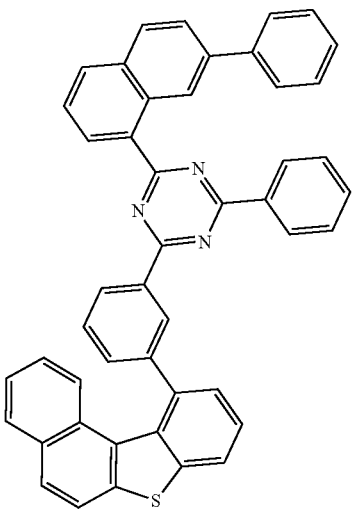
N-145
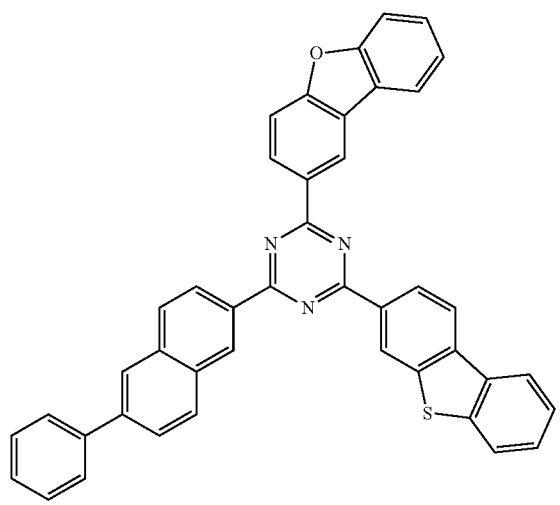
N-146
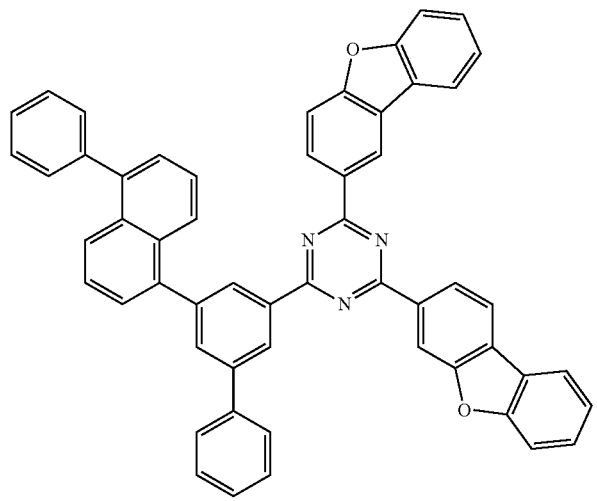
N-147
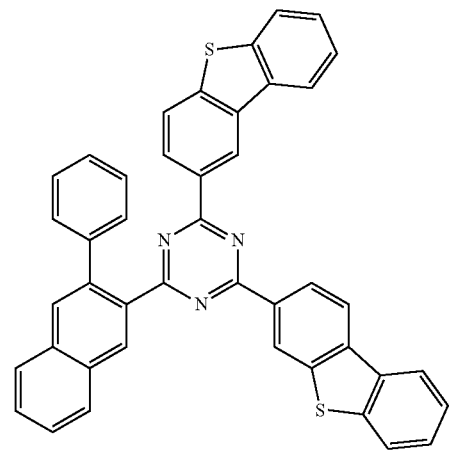

-continued
N-148
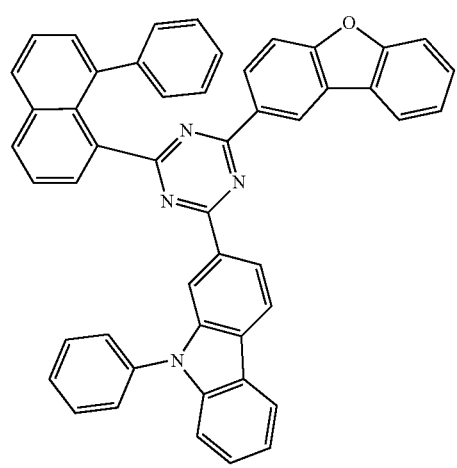
N-149
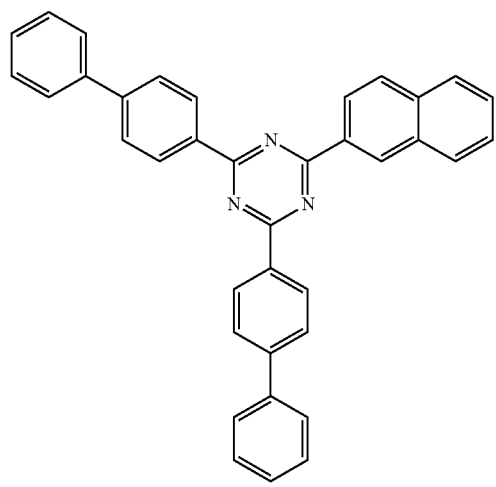
N-150
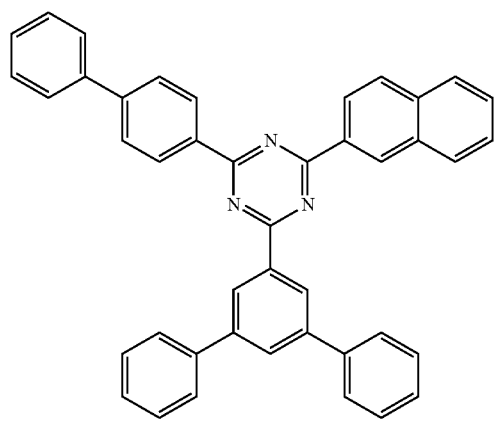
N-151
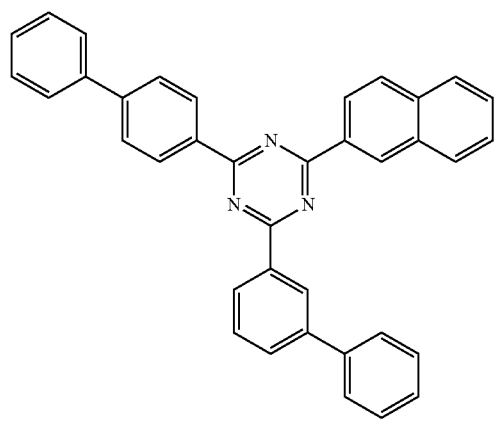
N-152
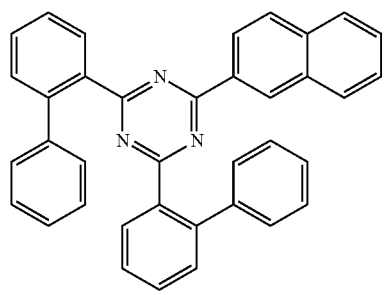
N-153
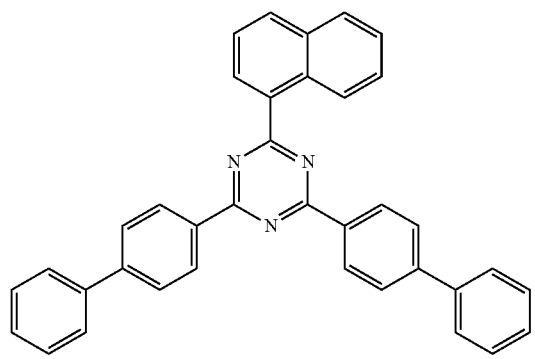

-continued
N-154
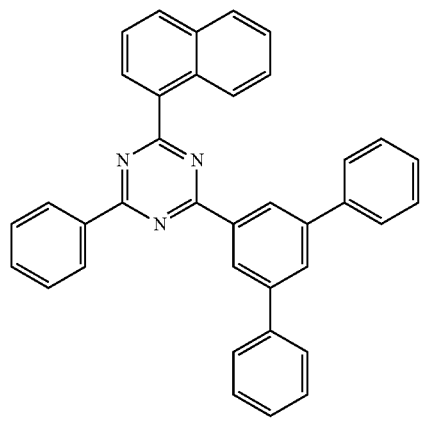
N-155
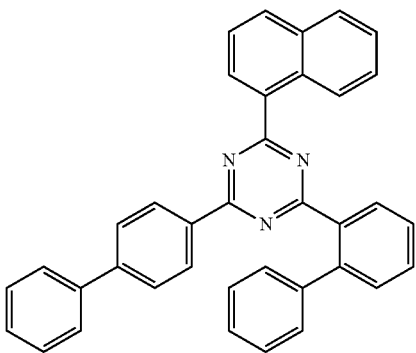
N-156
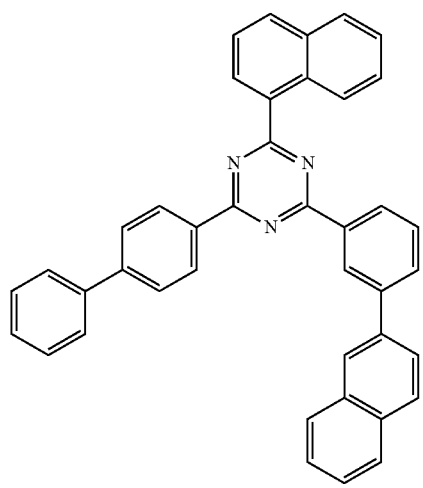
N-157
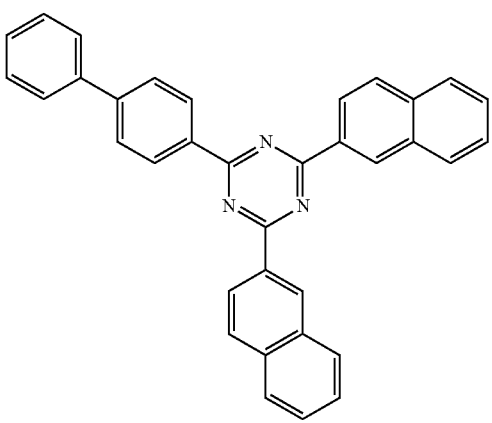
N-158
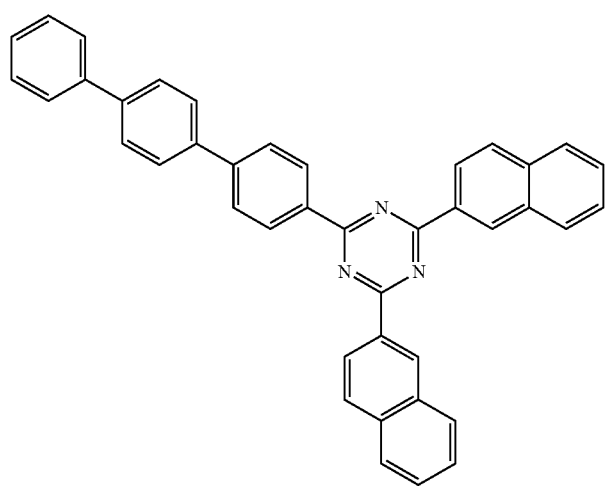

-continued
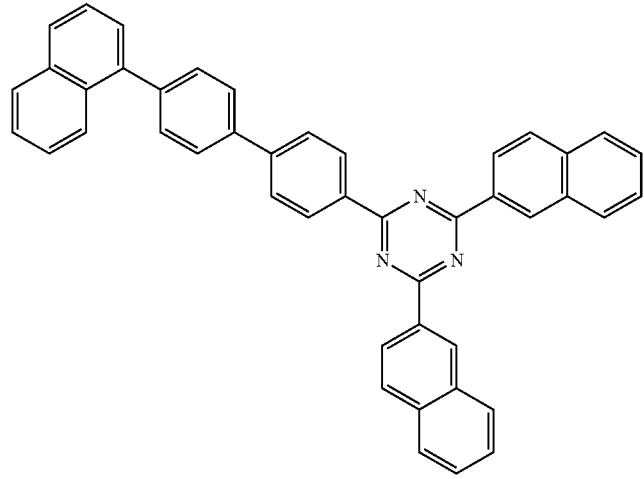
N-159
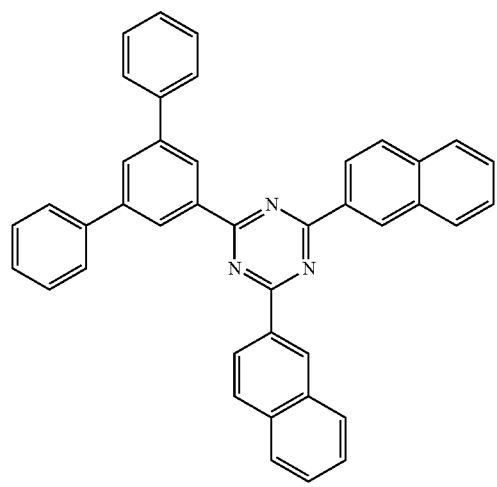
N-160
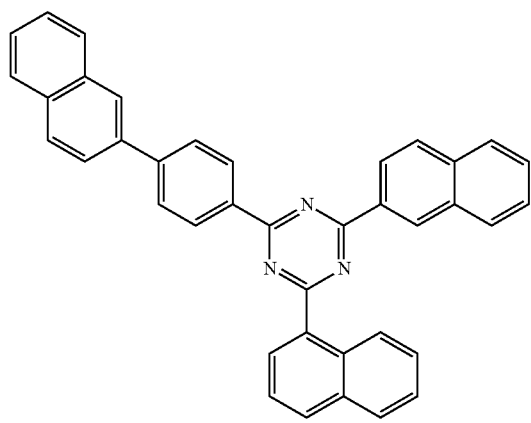
N-161
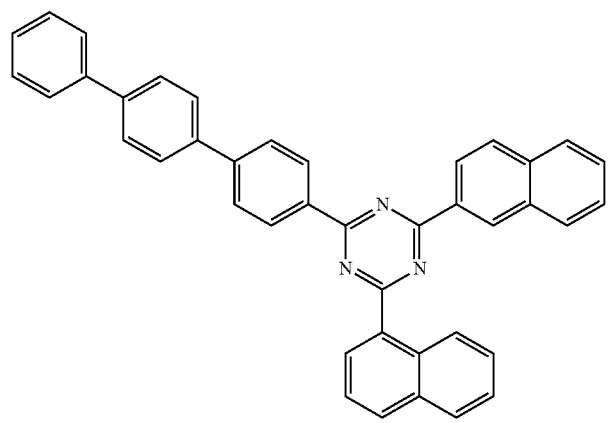
N-162

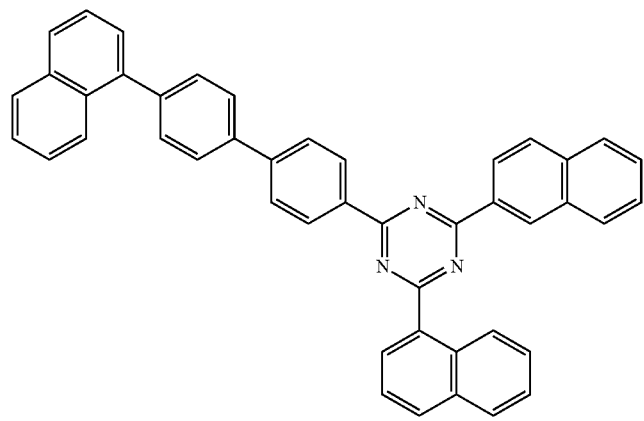
N-163
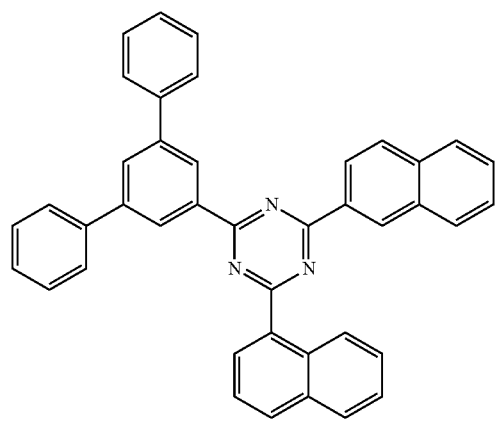
N-164
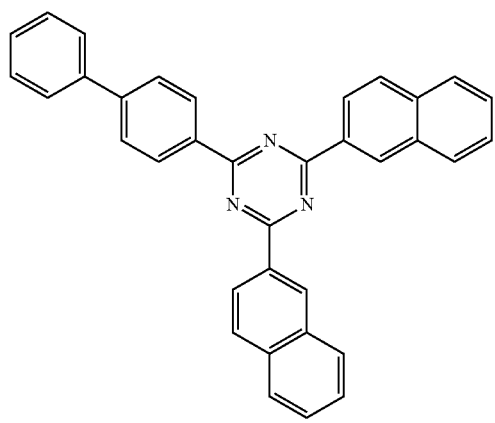
N-165
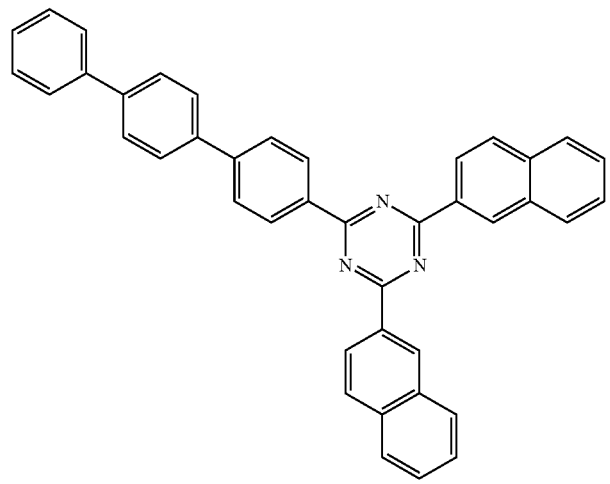
N-166

-continued
N-167
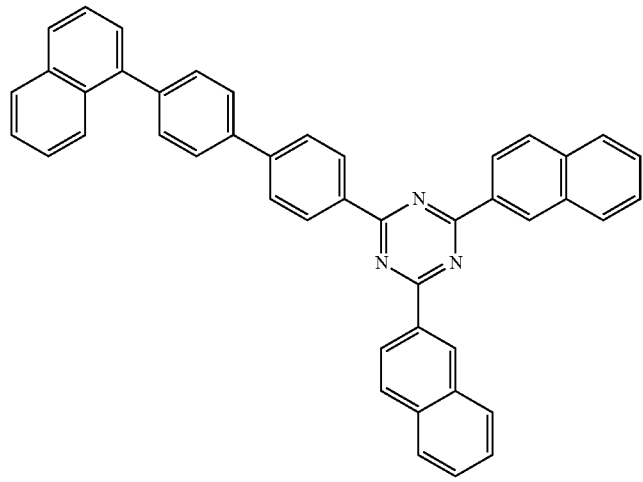
N-168
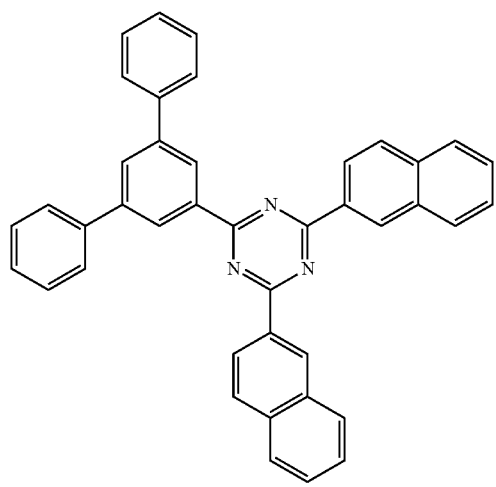
N-169
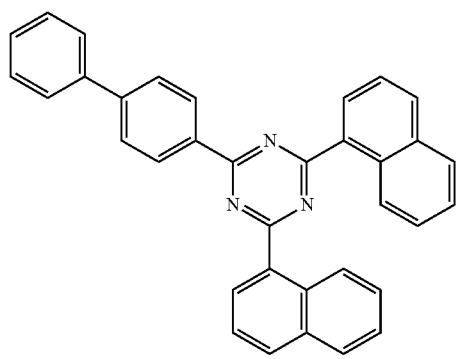
N-170
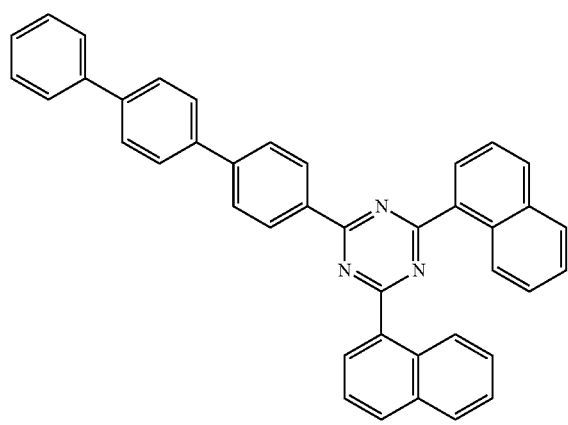
N-171
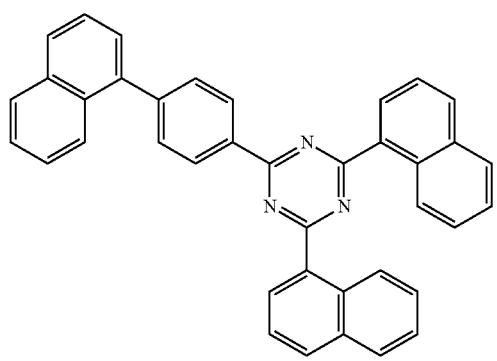

-continued
N-172
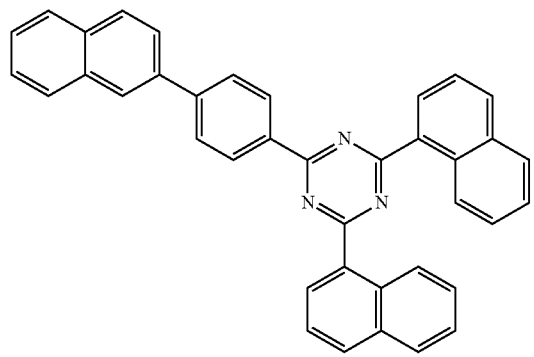
N-173
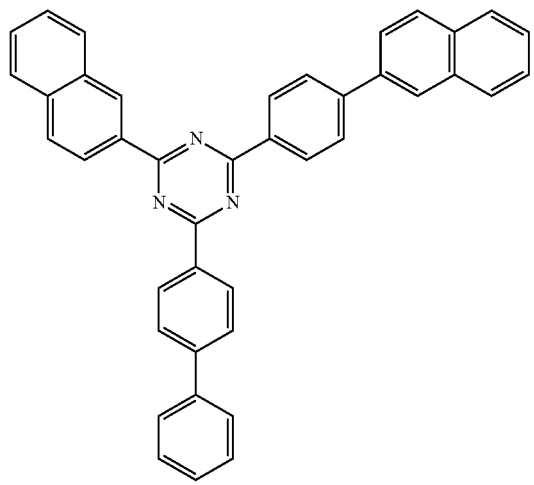
N-174
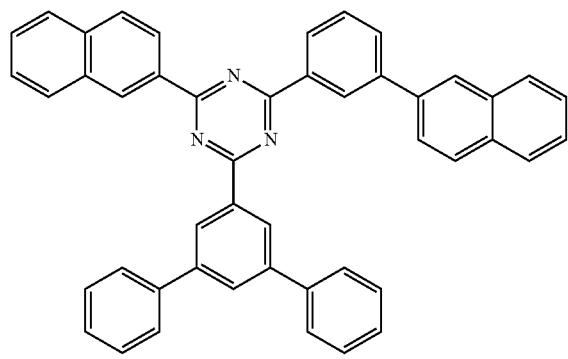
N-175
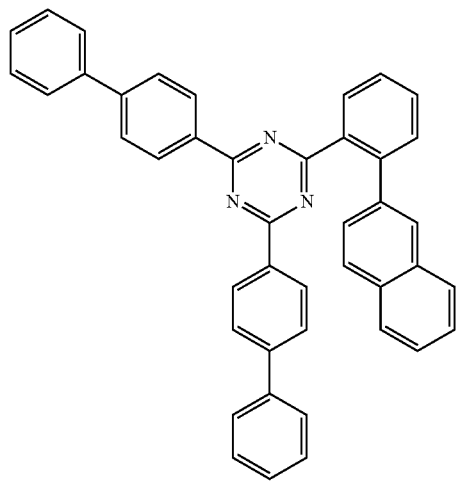
N-176
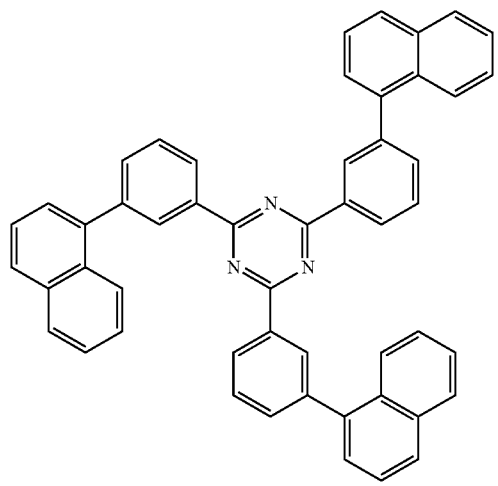
N-177
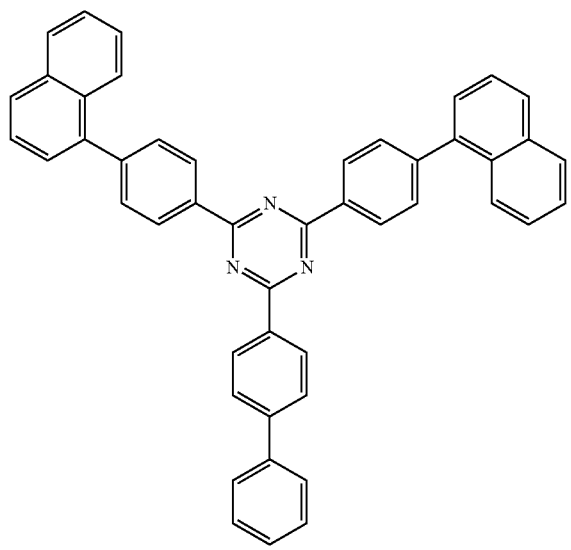

-continued
N-178
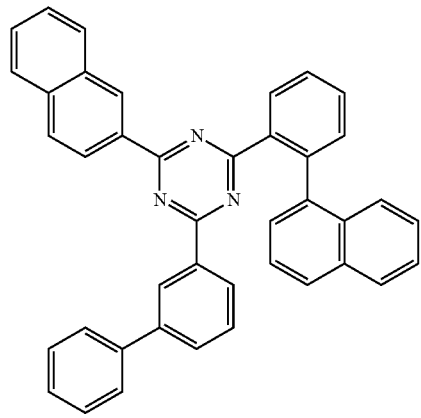
N-179
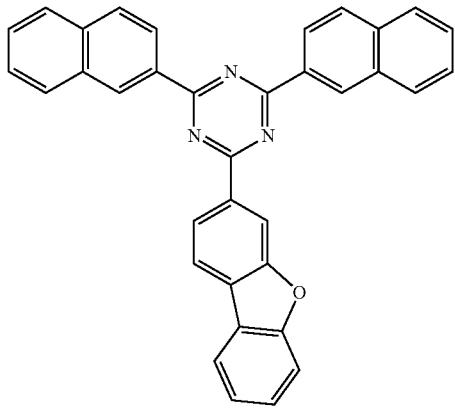
N-180
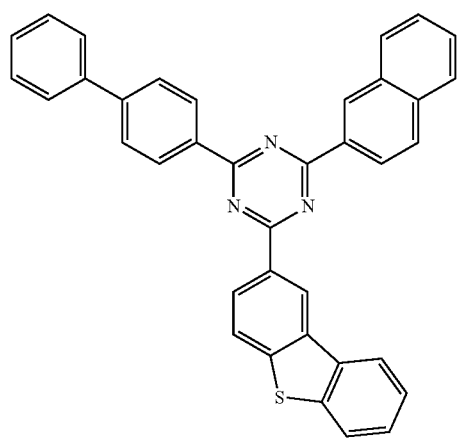
N-181
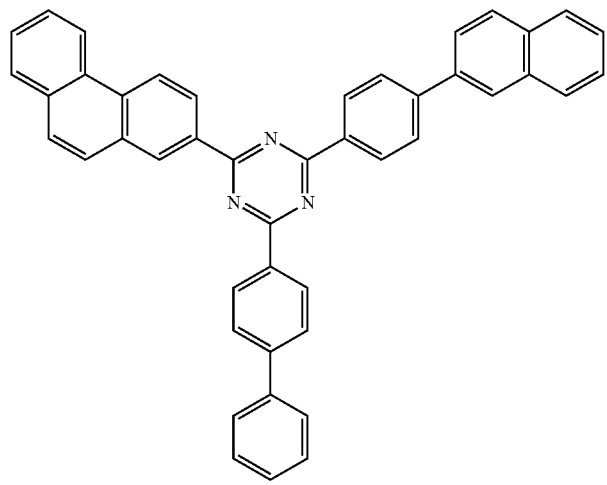

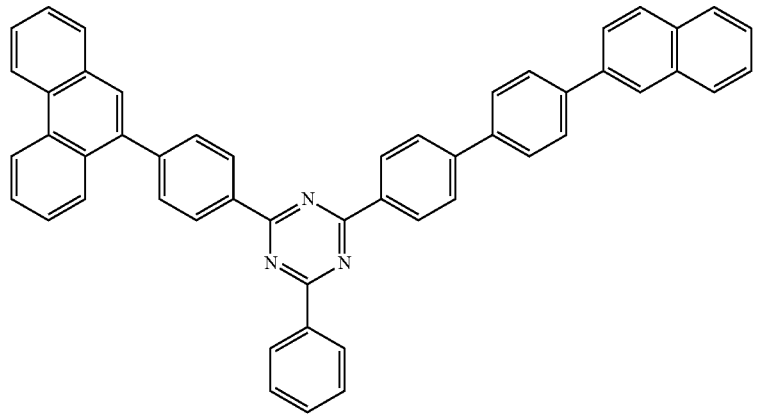

N-182

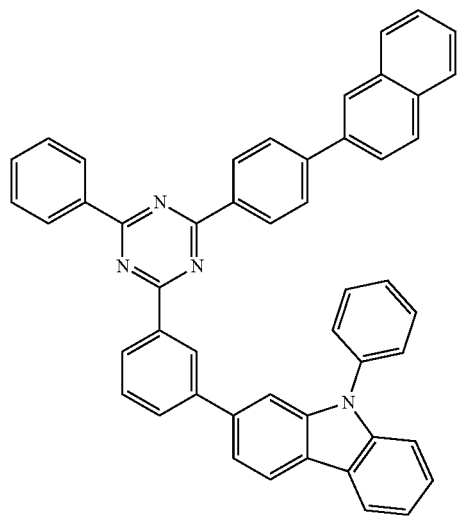

N-183

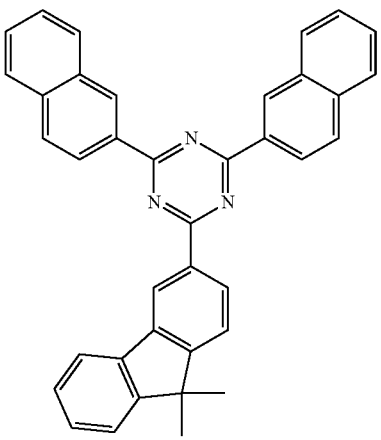

N-184

The present invention may further include a light efficiency enhancing layer formed on at least one surface of the first electrode and the second electrode opposite to the organic material layer.

Also, the organic material layer may include 2 or more stacks including a hole transport layer, an emitting layer, and an electron transport layer sequentially formed on the anode, and the organic material layer may further include a charge generation layer formed between the 2 or more stacks.

In another aspect, the present invention provides an electronic device comprising a display device including the organic electronic element; and a control unit for driving the display device; here, the organic electronic element is at least one of an OLED, an organic solar cell, an organic photo conductor, an organic transistor and an element for monochromic or white illumination.

Hereinafter, Synthesis Examples of the compound represented by Formula according to the present invention and preparation examples of the organic electronic element according to the present invention will be described in detail by way of example, but are not limited to the following examples of the invention.

Synthesis Example 1

The compound represented by Formula 1 according to the present invention (final product 1) (disclosed in Korean Patent Registration Nos. 10-2018682, 10-2018683 (registration notice dated Sep. 4, 2019) of the applicant) is synthesized by reacting Sub 1 and Sub 2 as shown in Scheme 1, but is not limited thereto.

<Reaction Scheme 1>

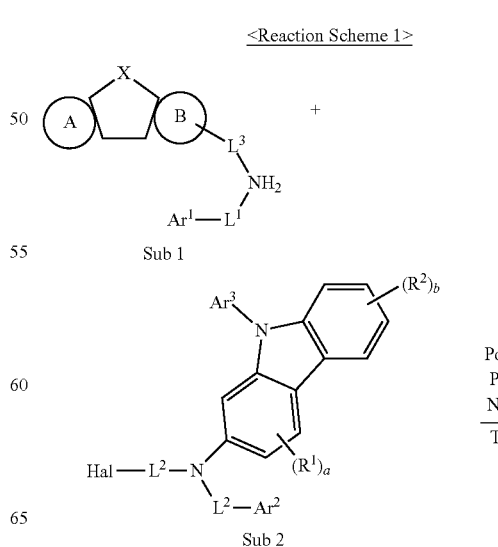

-continued

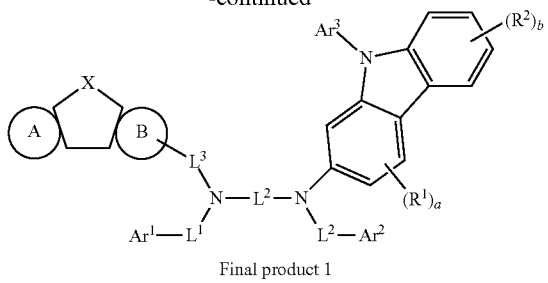

Final product 1

(Hal is I, Br or Cl)

I. Synthesis of Sub 1

Sub 1 of Reaction Scheme 2 may be synthesized by Reaction Scheme 2, but is not limited thereto.

<Reaction Scheme 2>

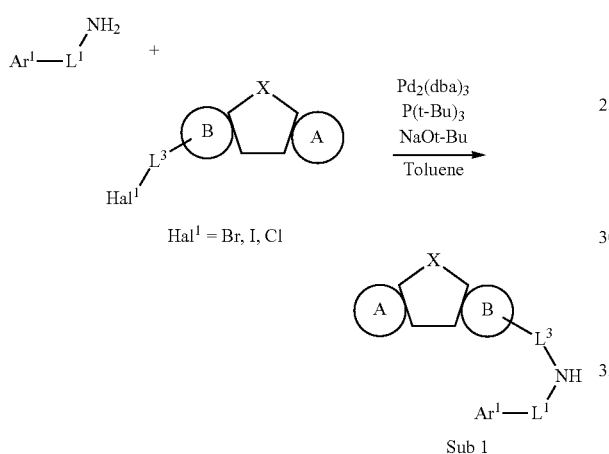

(Hal¹ is I, Br and Cl)

1. Synthesis Example of Sub 1-P-2

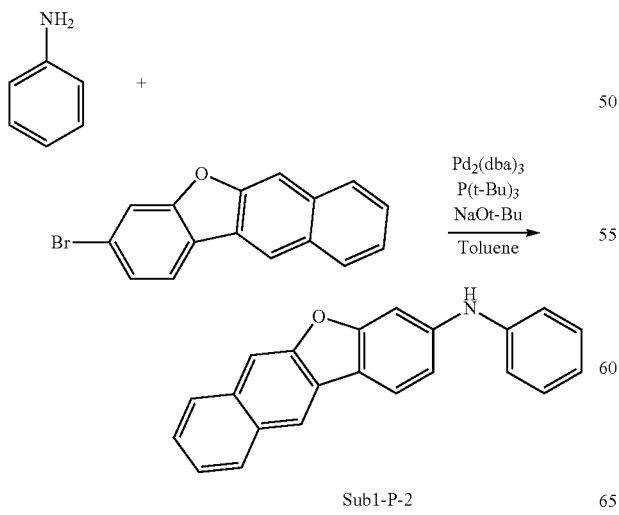

Aniline (50 g, 536.9 mmol), 3-bromonaphtho[2,3-b]benzofuran (158.9 g, 536.9 mmol), Pd$_2$(dba)$_3$ (14.75 g, 16.1 mmol), P(t-Bu)$_3$ (6.52 g, 32.2 mmol), NaOt-Bu (103.2 g, 1073.8 mmol), toluene (2,684 mL) were added in a round bottom flask, followed by reaction at 100° C. When the reaction was completed, the resulting compound was extracted with CH$_2$Cl$_2$ and water, and the organic layer was dried over MgSO$_4$, concentrated, and the resulting compound was recrystallized with a silica gel column to obtain 129.5 g of a product. (Yield: 78%)

2. Synthesis Example of Sub 1-P-45

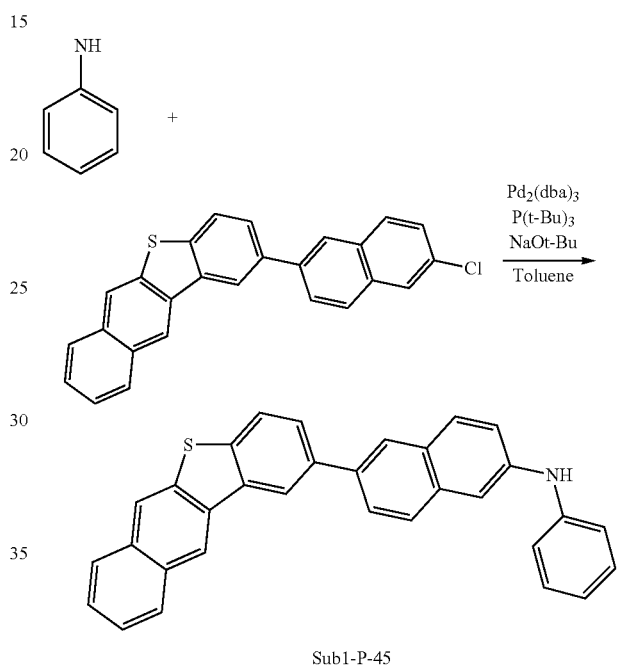

Aniline (10 g, 107.4 mmol), 2-(6-chloronaphthalen-2-yl) benzo[b]naphtho[2,3-d]thiophene (42.4 g, 107.4 mmol), Pd$_2$(dba)$_3$ (3 g, 3.2 mmol), P(t-Bu)$_3$ (1.4 g, 6.4 mmol), NaOt-Bu (20.6 g, 214.8 mmol), toluene (550 mL) were added in a round bottom flask, followed by reaction at 100° C. When the reaction was completed, the resulting compound was extracted with CH$_2$Cl$_2$ and water, and the organic layer was dried over MgSO$_4$, concentrated, and the resulting compound was recrystallized with a silica gel column to obtain 34.4 g of a product. (Yield: 71%)

The compound belonging to Sub 1 may be a compound as follows, but is not limited thereto, and Table 1 shows FD-MS (Field Desorption-Mass Spectrometry) values of some compounds belonging to Sub 1.

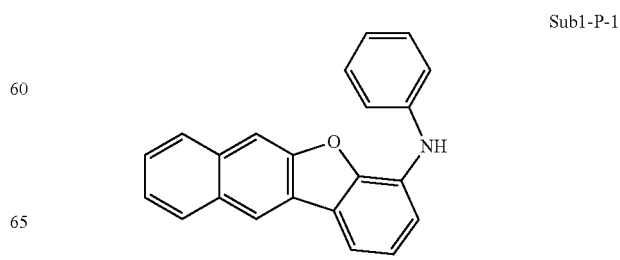

Sub1-P-2
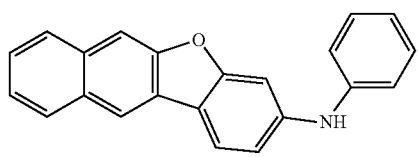
Sub1-P-3
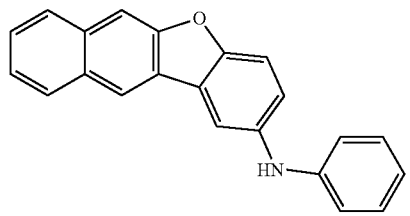
Sub1-P-4
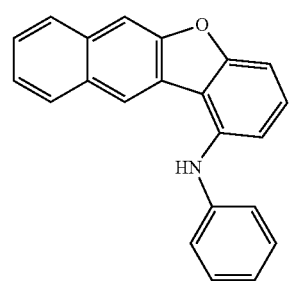
Sub1-P-5
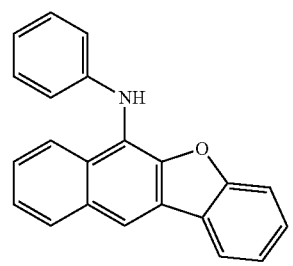
Sub1-P-6
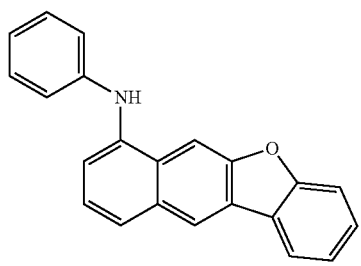
Sub1-P-7
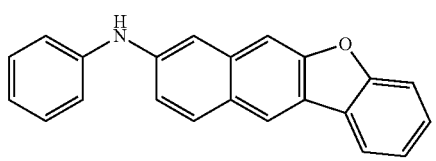
Sub1-P-8
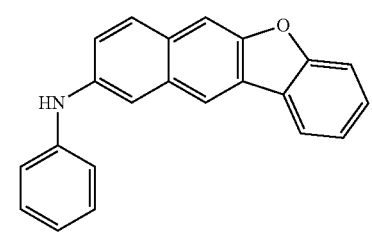
Sub1-P-9
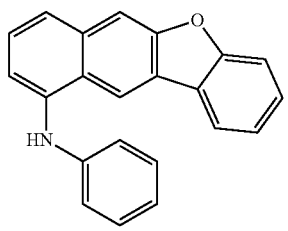
Sub1-P-10
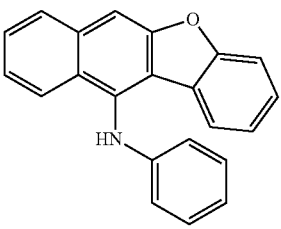
Sub1-P-11
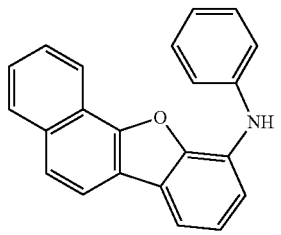
Sub1-P-12
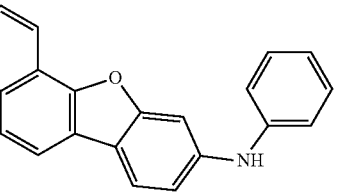
Sub1-P-13
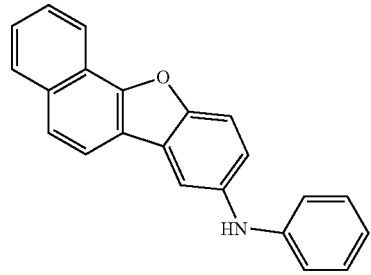
Sub1-P-14
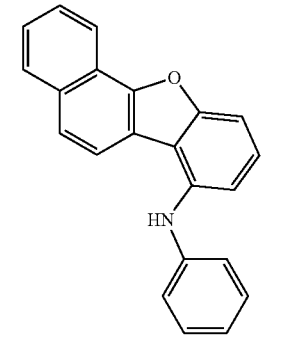

Sub1-P-15
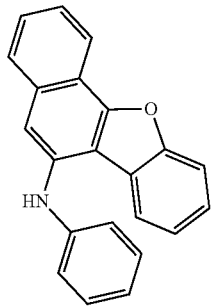
Sub1-P-16
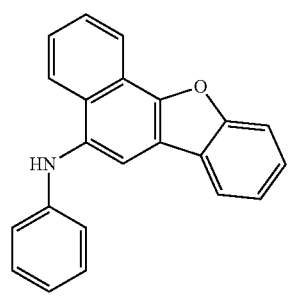
Sub1-P-17
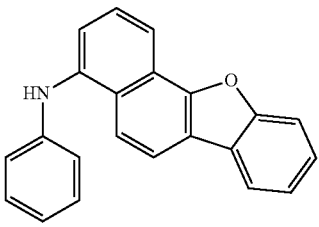
Sub1-P-18
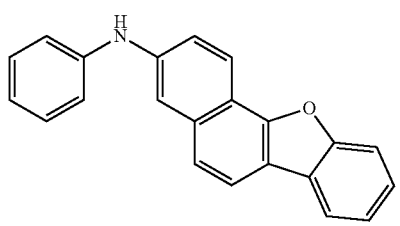
Sub1-P-19
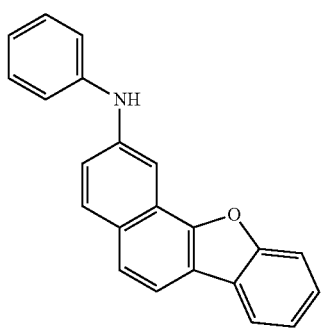
Sub1-P-20
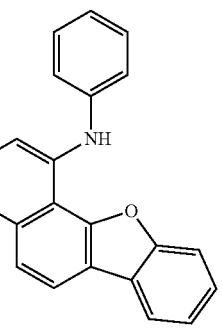
Sub1-P-21
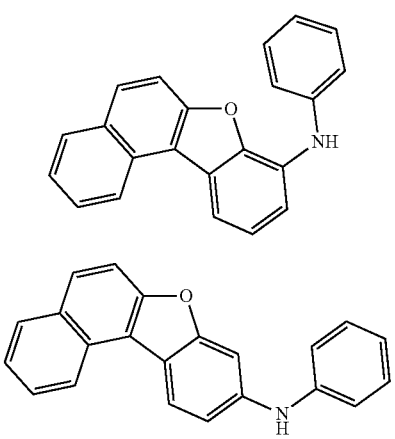
Sub1-P-22
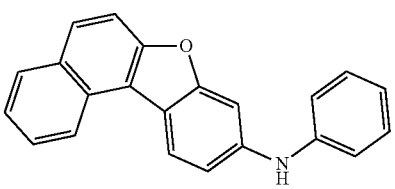
Sub1-P-23
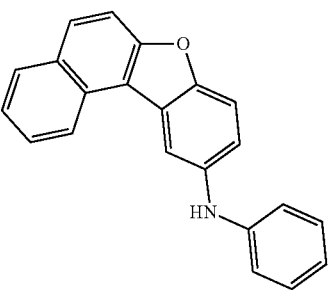
Sub1-P-24
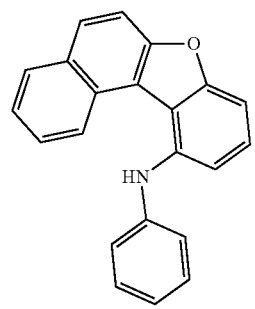
Sub1-P-25
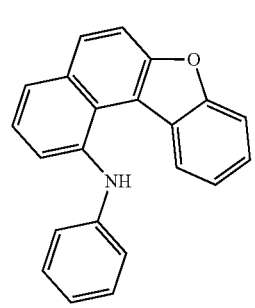

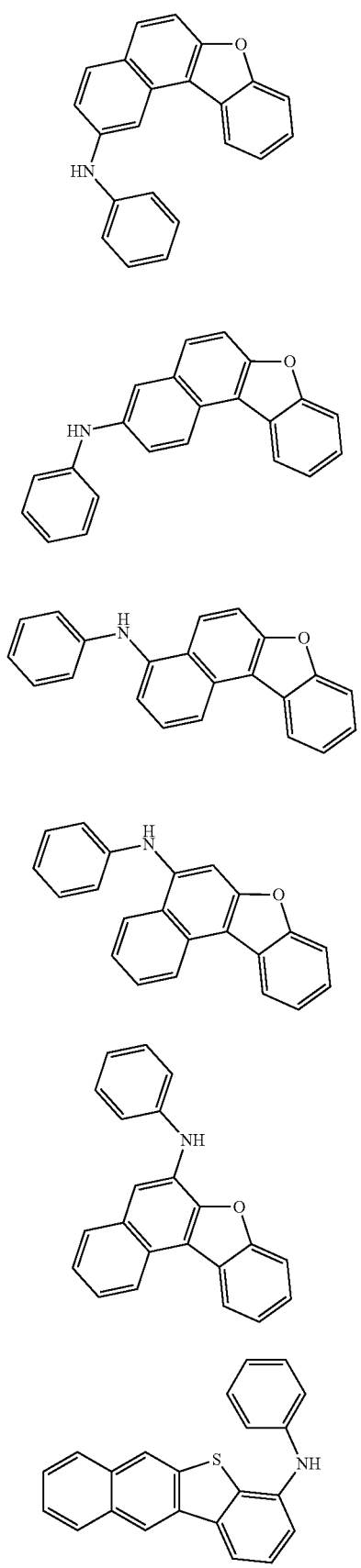
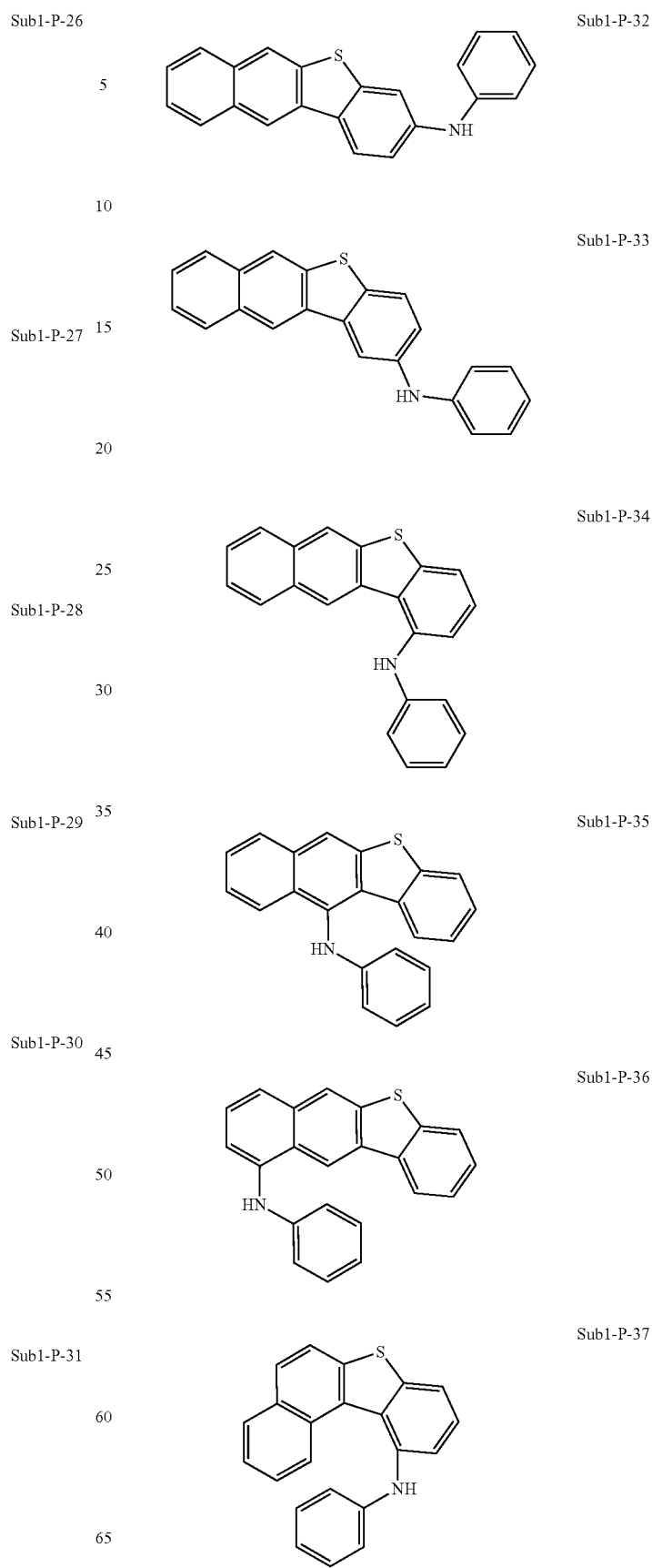

-continued

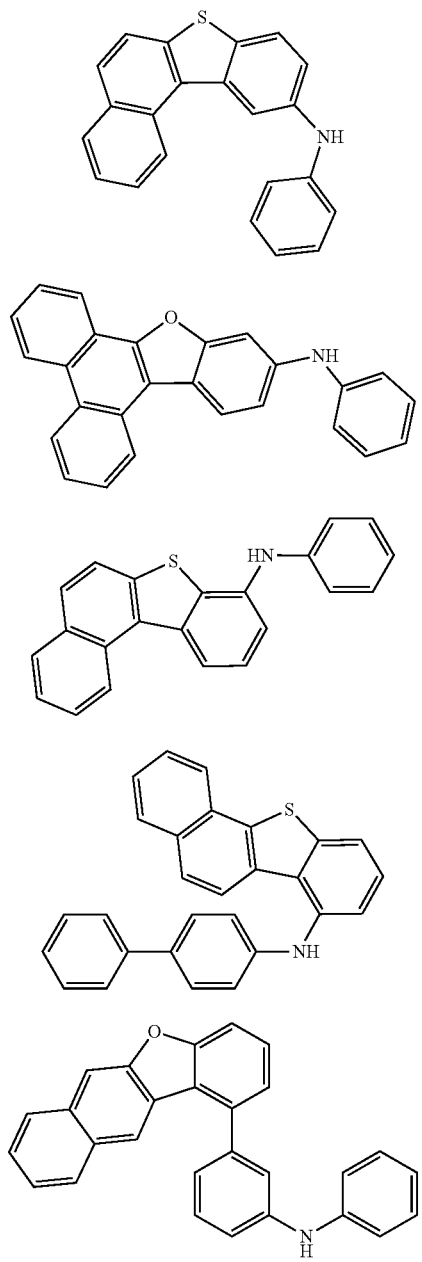

Sub1-P-38

Sub1-P-39

Sub1-P-40

Sub1-P-41

Sub1-P-42

-continued

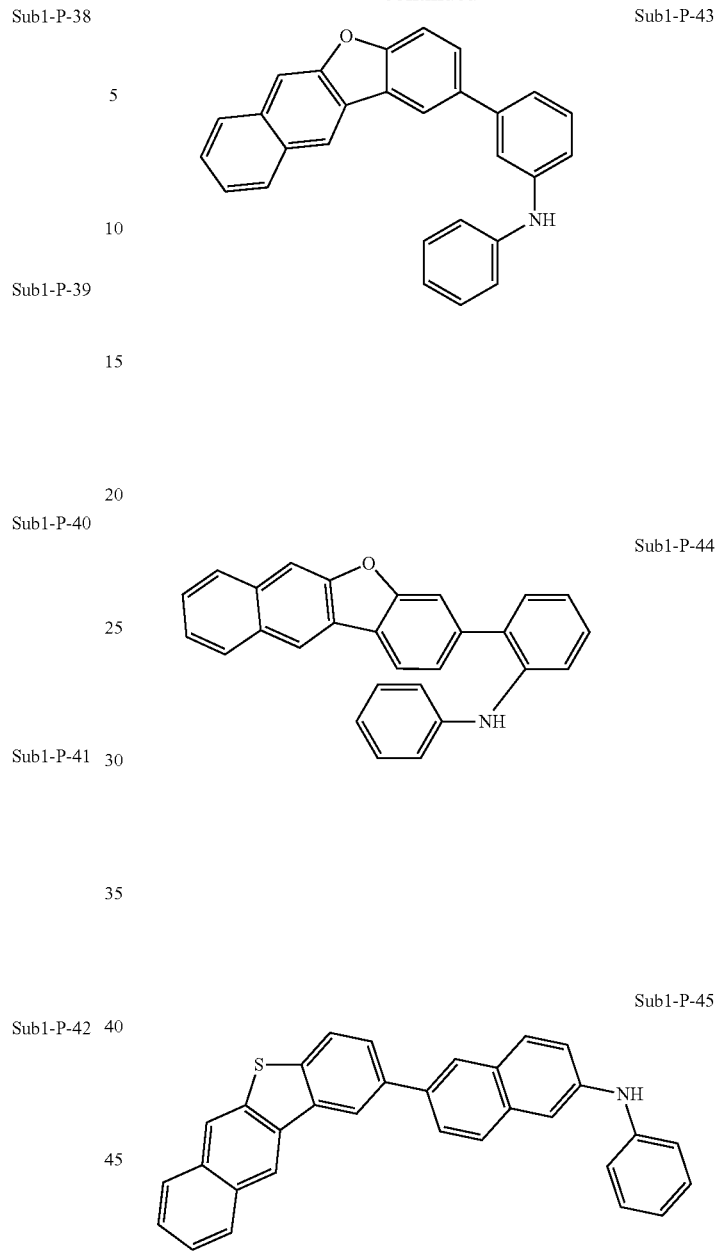

Sub1-P-43

Sub1-P-44

Sub1-P-45

TABLE 1

| compound | FD-MS | compound | FD-MS |
|---|---|---|---|
| Sub1-P-1 | m/z = 309.12($C_{22}H_{15}NO$ = 309.37) | Sub1-P-2 | m/z = 309.12($C_{22}H_{15}NO$ = 309.37) |
| Sub1-P-3 | m/z = 309.12($C_{22}H_{15}NO$ = 309.37) | Sub1-P-4 | m/z = 309.12($C_{22}H_{15}NO$ = 309.37) |
| Sub1-P-5 | m/z = 309.12($C_{22}H_{15}NO$ = 309.37) | Sub1-P-6 | m/z = 309.12($C_{22}H_{15}NO$ = 309.37) |
| Sub1-P-7 | m/z = 309.12($C_{22}H_{15}NO$ = 309.37) | Sub1-P-8 | m/z = 309.12($C_{22}H_{15}NO$ = 309.37) |
| Sub1-P-9 | m/z = 309.12($C_{22}H_{15}NO$ = 309.37) | Sub1-P-10 | m/z = 309.12($C_{22}H_{15}NO$ = 309.37) |
| Sub1-P-11 | m/z = 309.12($C_{22}H_{15}NO$ = 309.37) | Sub1-P-12 | m/z = 309.12($C_{22}H_{15}NO$ = 309.37) |
| Sub1-P-13 | m/z = 309.12($C_{22}H_{15}NO$ = 309.37) | Sub1-P-14 | m/z = 309.12($C_{22}H_{15}NO$ = 309.37) |
| Sub1-P-15 | m/z = 309.12($C_{22}H_{15}NO$ = 309.37) | Sub1-P-16 | m/z = 309.12($C_{22}H_{15}NO$ = 309.37) |
| Sub1-P-17 | m/z = 309.12($C_{22}H_{15}NO$ = 309.37) | Sub1-P-18 | m/z = 309.12($C_{22}H_{15}NO$ = 309.37) |
| Sub1-P-19 | m/z = 309.12($C_{22}H_{15}NO$ = 309.37) | Sub1-P-20 | m/z = 309.12($C_{22}H_{15}NO$ = 309.37) |
| Sub1-P-21 | m/z = 309.12($C_{22}H_{15}NO$ = 309.37) | Sub1-P-22 | m/z = 309.12($C_{22}H_{15}NO$ = 309.37) |
| Sub1-P-23 | m/z = 309.12($C_{22}H_{15}NO$ = 309.37) | Sub1-P-24 | m/z = 309.12($C_{22}H_{15}NO$ = 309.37) |
| Sub1-P-25 | m/z = 309.12($C_{22}H_{15}NO$ = 309.37) | Sub1-P-26 | m/z = 309.12($C_{22}H_{15}NO$ = 309.37) |
| Sub1-P-27 | m/z = 309.12($C_{22}H_{15}NO$ = 309.37) | Sub1-P-28 | m/z = 309.12($C_{22}H_{15}NO$ = 309.37) |
| Sub1-P-29 | m/z = 309.12($C_{22}H_{15}NO$ = 309.37) | Sub1-P-30 | m/z = 309.12($C_{22}H_{15}NO$ = 309.37) |

TABLE 1-continued

| compound | FD-MS | compound | FD-MS |
|---|---|---|---|
| Sub1-P-31 | m/z = 325.09($C_{22}H_{15}NS$ = 325.43) | Sub1-P-32 | m/z = 325.09($C_{22}H_{15}NS$ = 325.43) |
| Sub1-P-33 | m/z = 325.09($C_{22}H_{15}NS$ = 325.43) | Sub1-P-34 | m/z = 325.09($C_{22}H_{15}NS$ = 325.43) |
| Sub1-P-35 | m/z = 325.09($C_{22}H_{15}NS$ = 325.43) | Sub1-P-36 | m/z = 325.09($C_{22}H_{15}NS$ = 325.43) |
| Sub1-P-37 | m/z = 325.09($C_{22}H_{15}NS$ = 325.43) | Sub1-P-38 | m/z = 325.09($C_{22}H_{15}NS$ = 325.43) |
| Sub1-P-39 | m/z = 359.13($C_{26}H_{17}NO$ = 359.43) | Sub1-P-40 | m/z = 325.09($C_{22}H_{15}NS$ = 325.43) |
| Sub1-P-41 | m/z = 401.12($C_{28}H_{19}NS$ = 401.53) | Sub1-P-42 | m/z = 385.15($C_{28}H_{19}NO$ = 385.47) |
| Sub1-P-43 | m/z = 385.15($C_{28}H_{19}NO$ = 385.47) | Sub1-P-44 | m/z = 385.15($C_{28}H_{19}NO$ = 385.47) |
| Sub1-P-45 | m/z = 451.14($C_{32}H_{21}NS$ = 451.59) | | |

II. Synthesis of Sub 2

Sub 2 of Reaction Scheme 1 may be synthesized by the reaction path of Scheme 3, but is not limited thereto.

<Reaction Scheme 3>

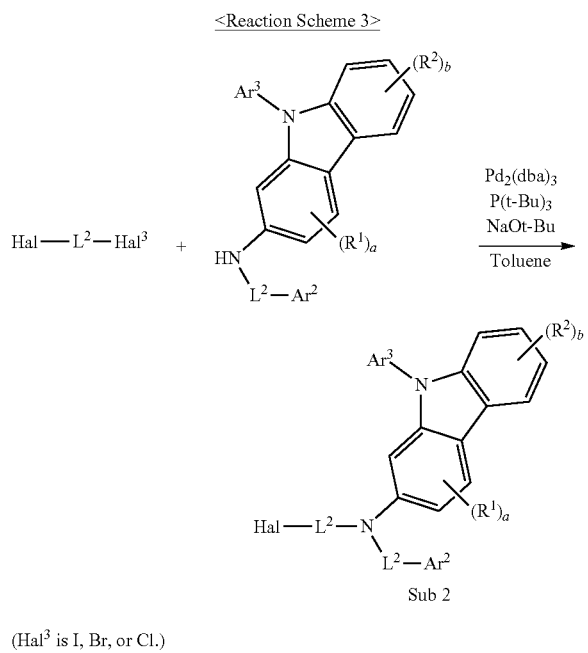

(Hal³ is I, Br, or Cl.)

1. Synthesis Example of Sub2-P-1

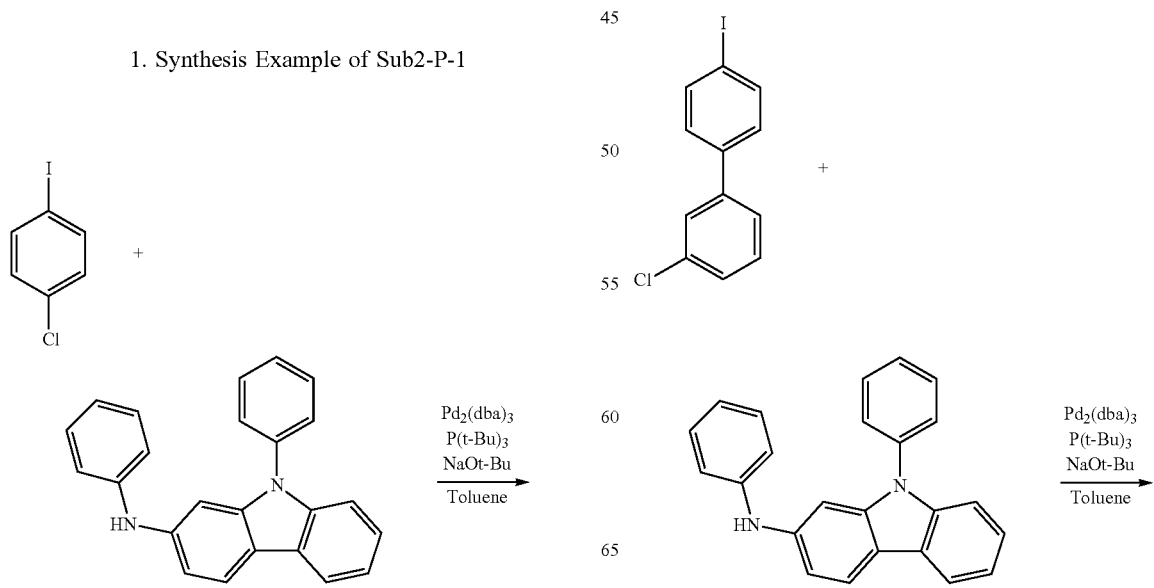

1-chloro-4-iodobenzene (25 g, 104.8 mmol), N,9-diphenyl-9H-carbazol-2-amine (35 g, 104.8 mmol), $Pd_2(dba)_3$ (7.4 g, 8.1 mmol), P(t-Bu)₃ (3.3 g, 16.2 mmol), NaOt-Bu (51.6 g, 536.9 mmol), toluene (1,000 mL) were added in a round bottom flask, followed by reaction at 100° C. When the reaction was completed, the resulting compound was extracted with $CH_2Cl_2$ and water, and the organic layer was dried over $MgSO_4$, concentrated, and the resulting compound was recrystallized with a silica gel column to obtain 38.7 g of a product. (Yield: 84%)

2. Synthesis Example of Sub2-P-17

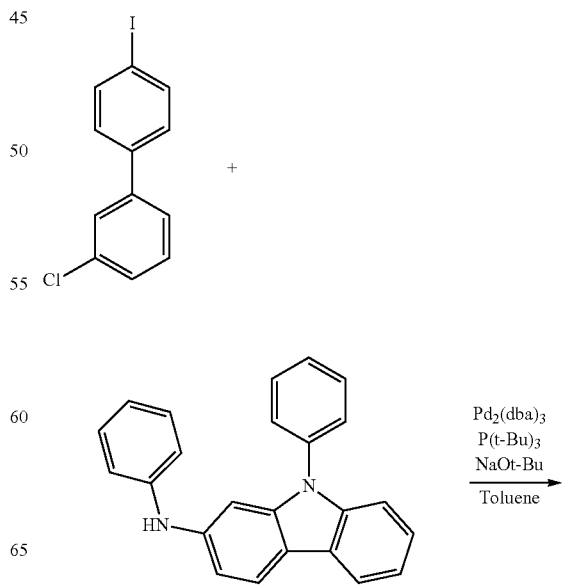

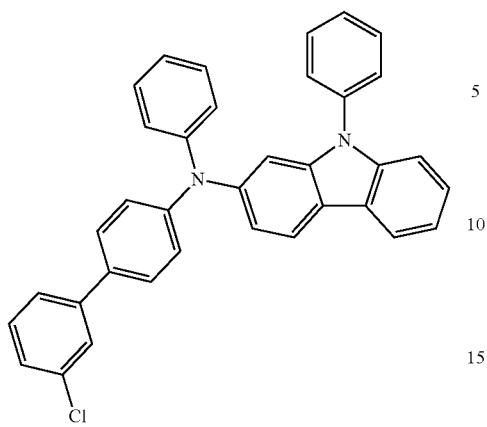

Sub2-P-17

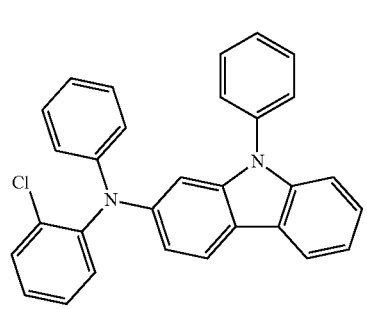

Sub2-P-3

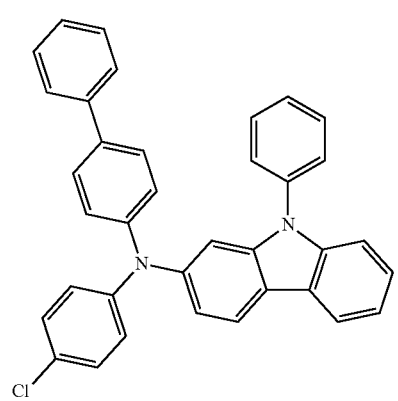

Sub2-P-4

3-chloro-4'-iodo-1,1'-biphenyl (32.9 g, 104.8 mmol), N,9-diphenyl-9H-carbazol-2-amine (35 g, 104.8 mmol), Pd$_2$(dba)$_3$ (7.4 g, 8.1 mmol), P(t-Bu)$_3$ (3.3 g, 16.2 mmol), NaOt-Bu (51.6 g, 536.9 mmol), toluene (1,000 mL) were added in a round bottom flask, followed by reaction at 100° C. When the reaction was completed, the resulting compound was extracted with CH$_2$Cl$_2$ and water, and the organic layer was dried over MgSO$_4$, concentrated, and the resulting compound was recrystallized with a silica gel column to obtain 44.2 g of a product. (Yield: 81%)

Compounds belonging to Sub 2 may be compounds as follows, but are not limited thereto, and Table 2 shows FD-MS (Field Desorption-Mass Spectrometry) values of some compounds belonging to Sub 2.

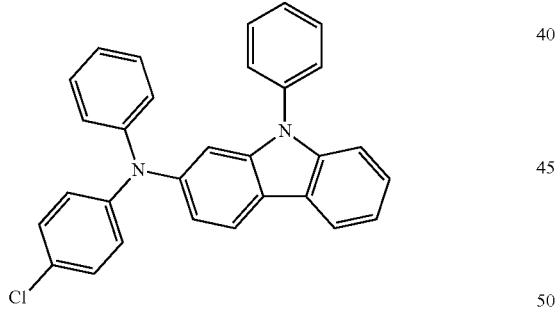

Sub2-P-1

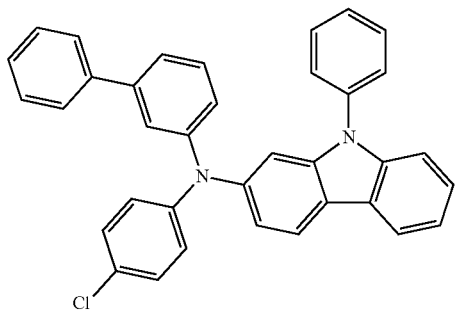

Sub2-P-5

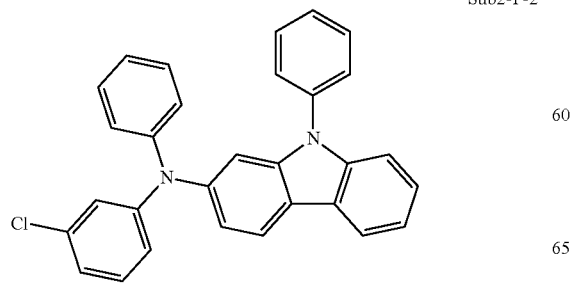

Sub2-P-2

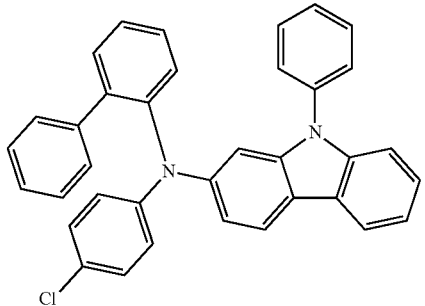

Sub2-P-6

Sub2-P-7
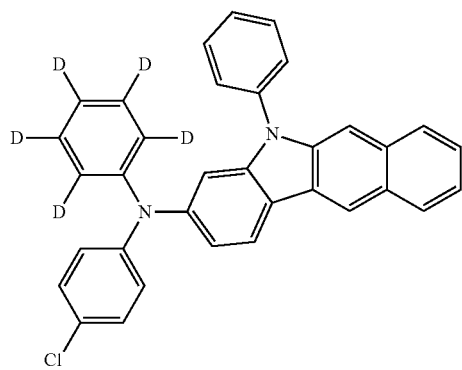
Sub2-P-8
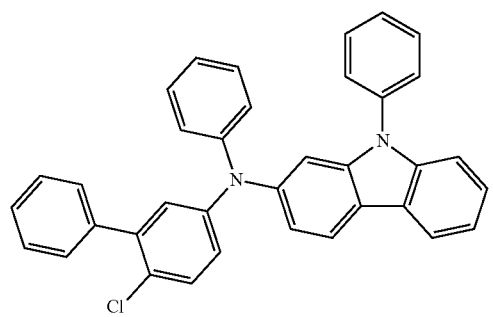
Sub2-P-9
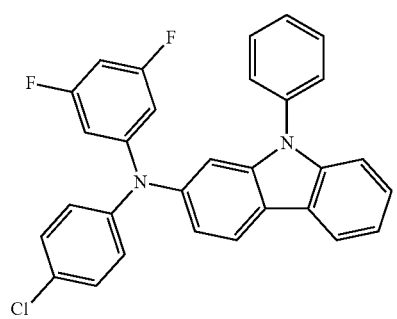
Sub2-P-10
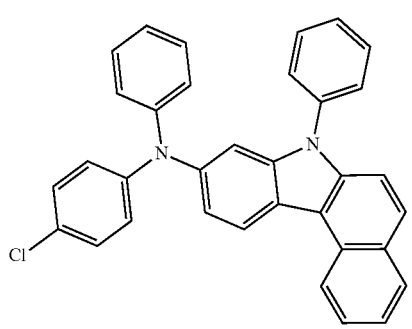
Sub2-P-11
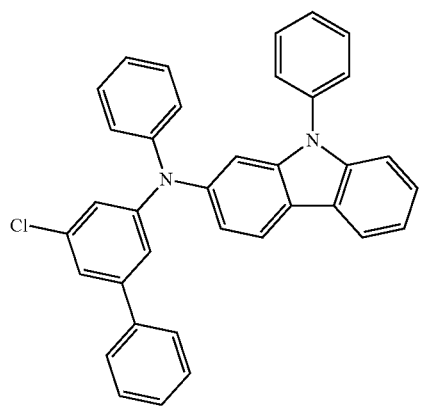
Sub2-P-12
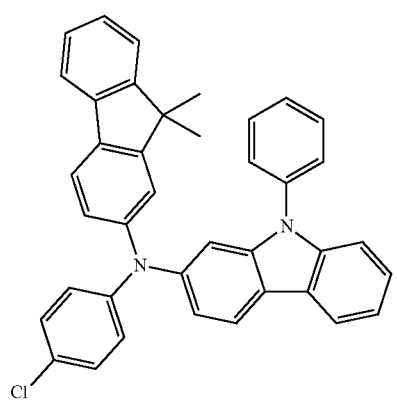
Sub2-P-13
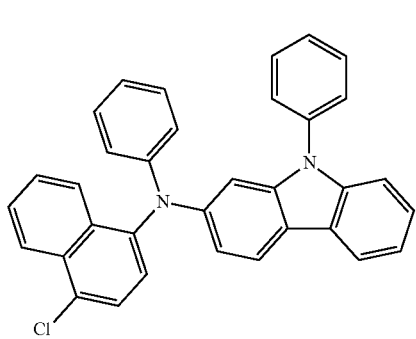
Sub2-P-14
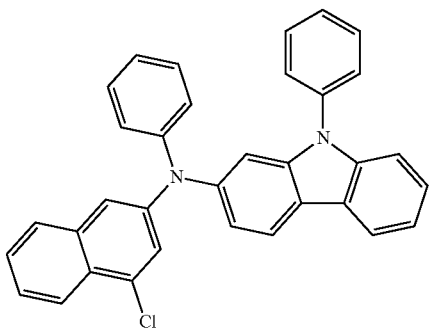

Sub2-P-15
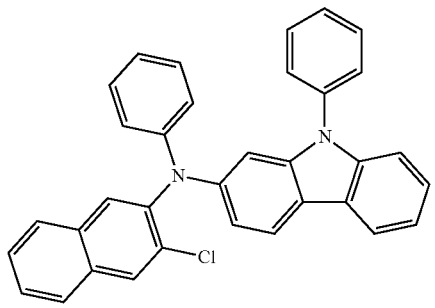
Sub2-P-16
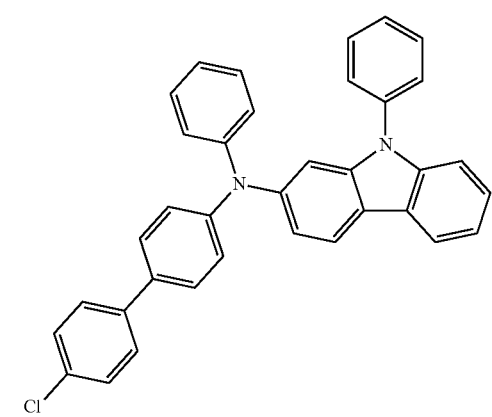
Sub2-P-17
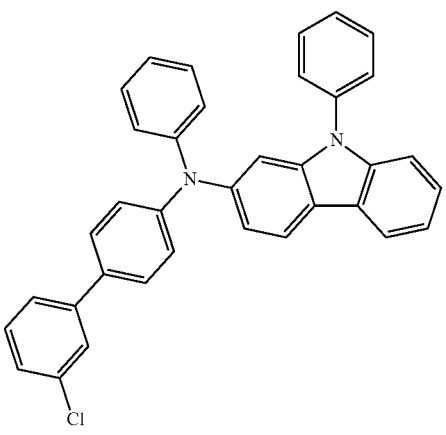
Sub2-P-18
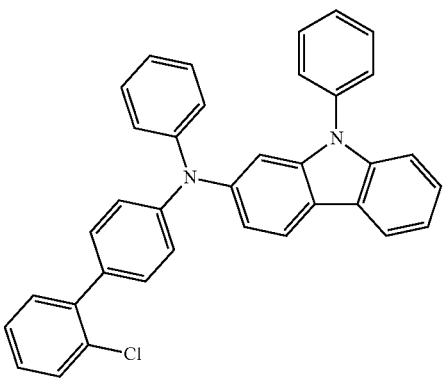
SubP2-P-19
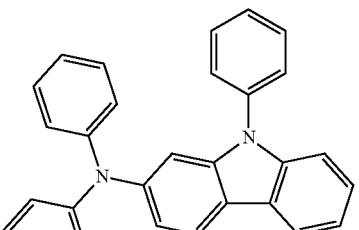
Sub2-P-20
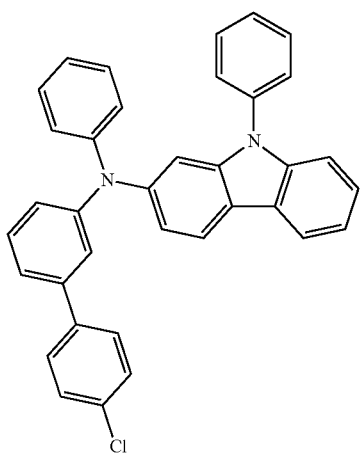
Sub2-P-21
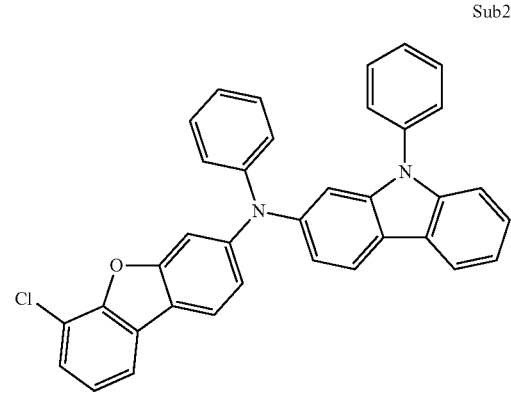
Sub2-P-22
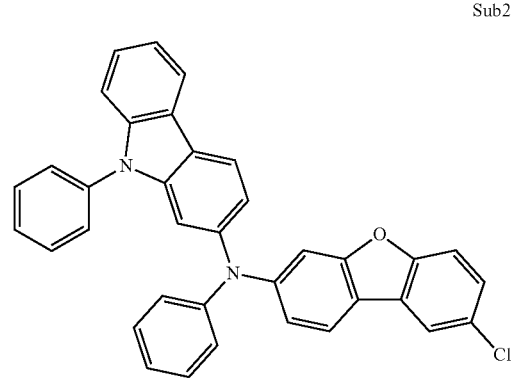

1. Synthesis Example of P-1

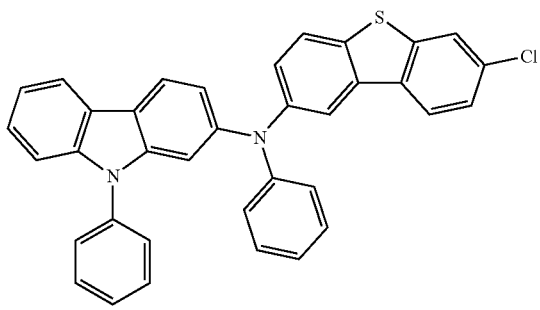

Sub2-P-23

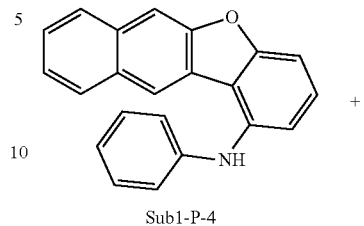

Sub1-P-4

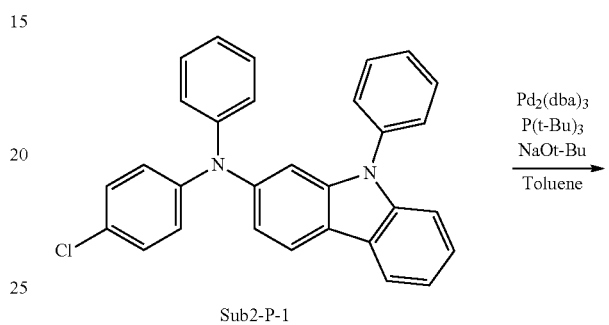

Sub2-P-1

Sub2-P-24

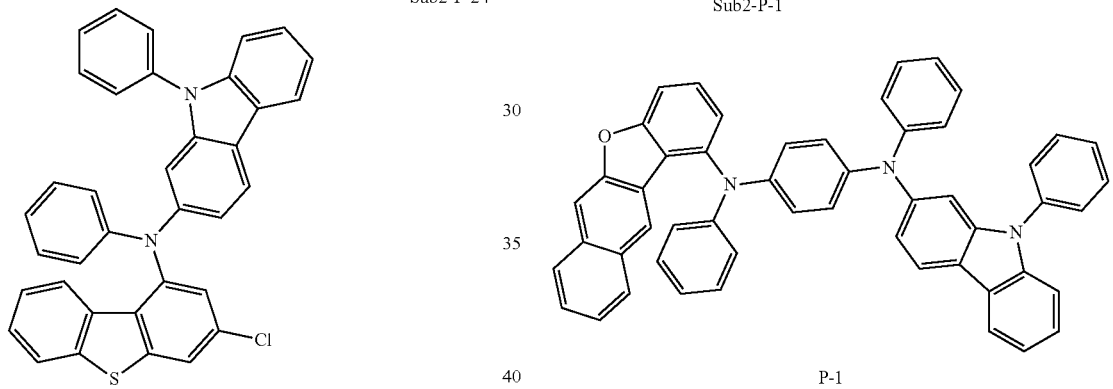

P-1

TABLE 2

| compound | FD-MS | compound | FD-MS |
|---|---|---|---|
| Sub2-P-1 | m/z = 444.14($C_{30}H_{21}ClN_2$ = 444.96) | Sub2-P-2 | m/z = 444.14($C_{30}H_{21}ClN_2$ = 444.96) |
| Sub2-P-3 | m/z = 444.14($C_{30}H_{21}ClN_2$ = 444.96) | Sub2-P-4 | m/z = 520.17($C_{36}H_{25}ClN_2$ = 521.06) |
| Sub2-P-5 | m/z = 520.17($C_{36}H_{25}ClN_2$ = 521.06) | Sub2-P-6 | m/z = 520.17($C_{36}H_{25}ClN_2$ = 521.06) |
| Sub2-P-7 | m/z = 499.19($C_{34}H_{18}D_5ClN_2$ = 500.05) | Sub2-P-8 | m/z = 520.17($C_{36}H_{25}ClN_2$ = 521.06) |
| Sub2-P-9 | m/z = 480.12($C_{30}H_{19}ClF_2N_2$ = 480.94) | Sub2-P-10 | m/z = 494.15($C_{34}H_{23}ClN_2$ = 495.02) |
| Sub2-P-11 | m/z = 520.17($C_{36}H_{25}ClN_2$ = 521.06) | Sub2-P-12 | m/z = 560.2($C_{39}H_{29}ClN_2$ = 561.13) |
| Sub2-P-13 | m/z = 494.15($C_{34}H_{23}ClN_2$ = 495.02) | Sub2-P-14 | m/z = 494.15($C_{34}H_{23}ClN_2$ = 495.02) |
| Sub2-P-15 | m/z = 494.15($C_{34}H_{23}ClN_2$ = 495.02) | Sub2-P-16 | m/z = 520.17($C_{36}H_{25}ClN_2$ = 521.06) |
| Sub2-P-17 | m/z = 520.17($C_{36}H_{25}ClN_2$ = 521.06) | Sub2-P-18 | m/z = 520.17($C_{36}H_{25}ClN_2$ = 521.06) |
| Sub2-P-19 | m/z = 520.17($C_{36}H_{25}ClN_2$ = 521.06) | Sub2-P-20 | m/z = 520.17($C_{36}H_{25}ClN_2$ = 521.06) |
| Sub2-P-21 | m/z = 534.15($C_{36}H_{23}ClN_2O$ = 535.04) | Sub2-P-22 | m/z = 534.15($C_{36}H_{23}ClN_2O$ = 535.04) |
| Sub2-P-23 | m/z = 550.13($C_{36}H_{23}ClN_2S$ = 551.1) | Sub2-P-24 | m/z = 550.13($C_{36}H_{23}ClN_2S$ = 551.1) |

III. Synthesis of Final Product 1

After dissolving Sub 1 (1 eq.) with Toluene in a round bottom flask, Sub 2 (1 eq.), $Pd_2(dba)_3$ (0.05 eq.), (t-Bu)$_3$P (0.1 eq.), and NaOt-Bu (3 eq.) were stirred at 100° C. When the reaction was completed, the resulting compound was extracted with $CH_2Cl_2$ and water, and the organic layer was dried over $MgSO_4$ and concentrated, and the resulting compound was recrystallized with a silica gel column to obtain Final product 1.

After dissolving Sub 1-1 (13.7 g, 20.5 mmol) with Toluene (180 in a round bottom flask, Sub 2-1 (3.48 g, 20.5 mmol), $Pd_2(dba)_3$ (0.56 g, 0.62 mmol), P(t-Bu)$_3$ (4.16 g, 20.5 mmol), NaOt-Bu (3.95 g, 41.1 mmol) were added and stirred at 120° C. When the reaction was completed, the resulting compound was extracted with $CH_2Cl_2$ and water, and the organic layer was dried over $MgSO_4$ and concentrated, and the resulting compound was recrystallized with a silica gel column to obtain P-1 (6 g, yield: 84%)

2. Synthesis Example of P-13
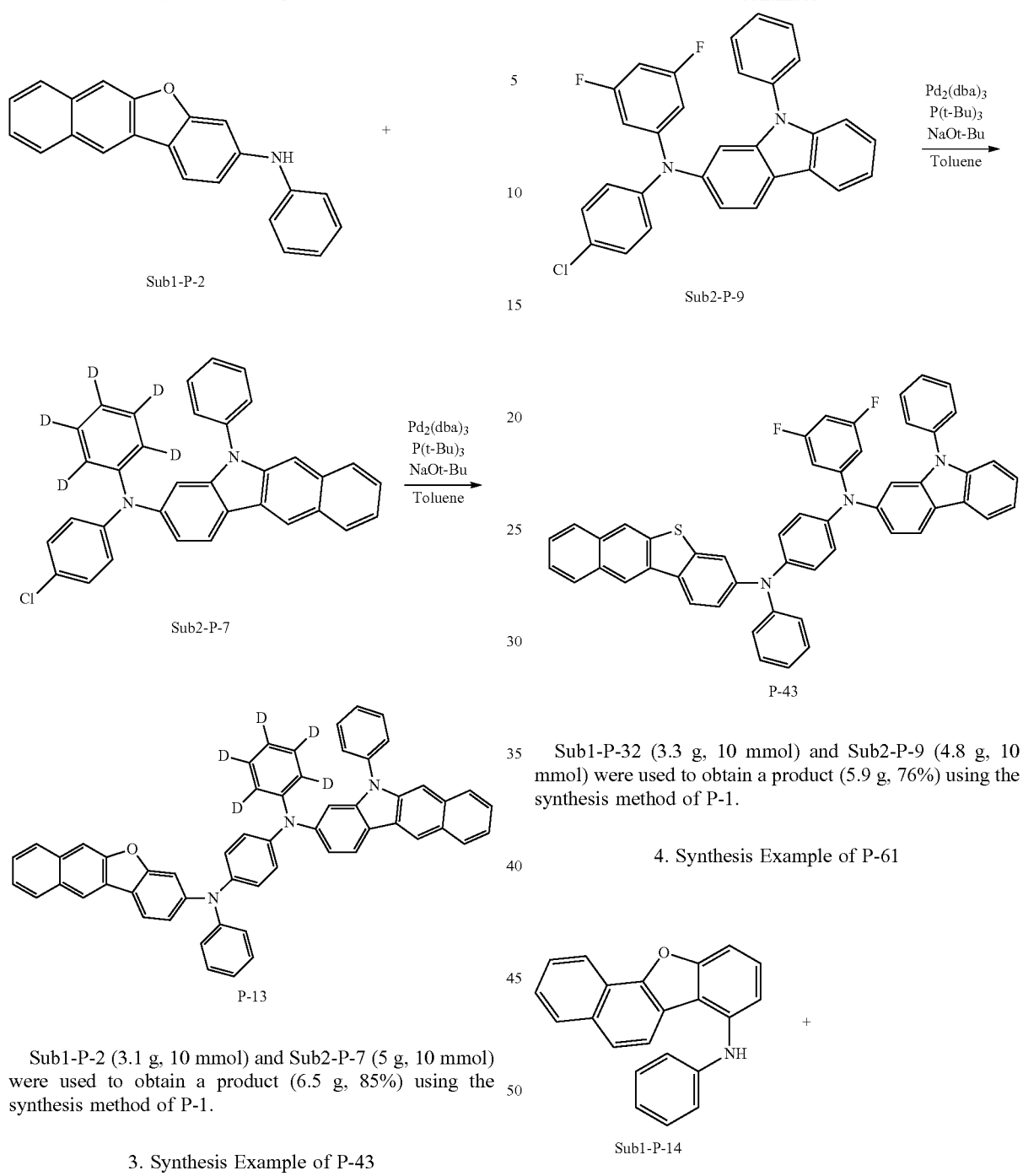
Sub1-P-2 (3.1 g, 10 mmol) and Sub2-P-7 (5 g, 10 mmol) were used to obtain a product (6.5 g, 85%) using the synthesis method of P-1.
3. Synthesis Example of P-43
Sub1-P-32 (3.3 g, 10 mmol) and Sub2-P-9 (4.8 g, 10 mmol) were used to obtain a product (5.9 g, 76%) using the synthesis method of P-1.
4. Synthesis Example of P-61
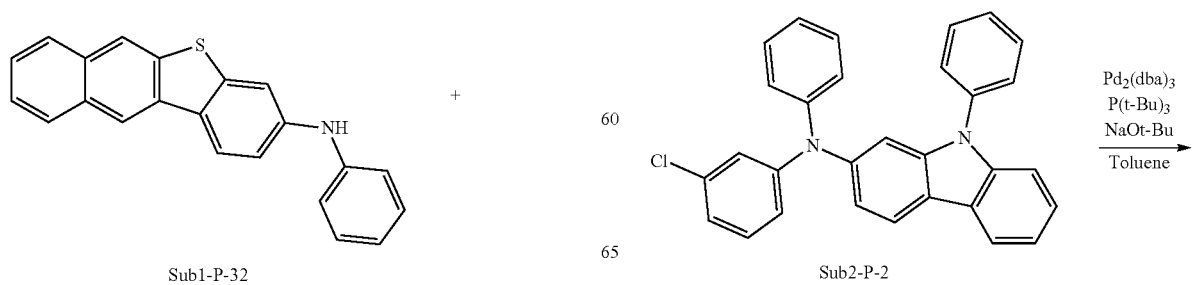

-continued
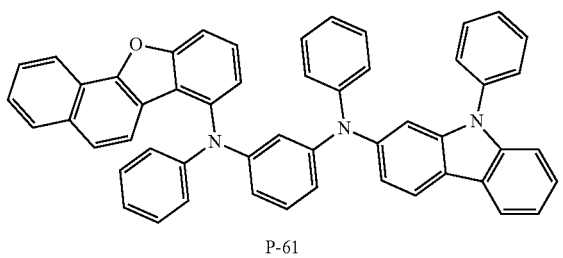
P-61
Sub1-P-14 (3.1 g, 10 mmol) and Sub2-P-2 (4.4 g, 10 mmol) were used to obtain a product (5.1 g, 71%) using the synthesis method of P-1.
5. Synthesis Example of P-97
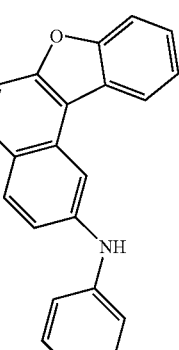
Sub1-P-35
6. Synthesis Example of P-109
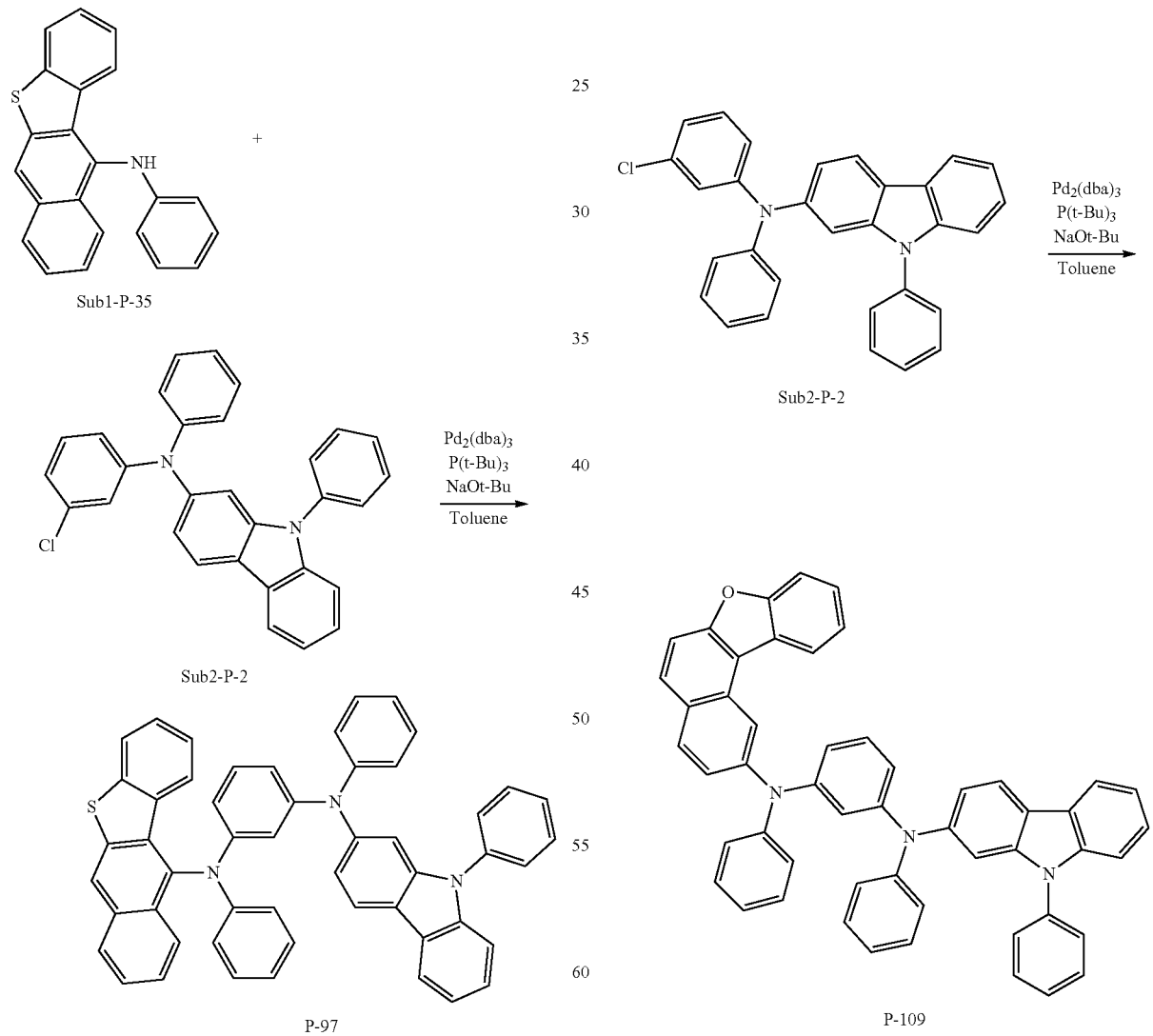
Sub1-P-35 (3.3 g, 10 mmol) and Sub2-P-2 (4.4 g, 10 mmol) were used to obtain a product (5.4 g, 74%) using the synthesis method of P-1.
Sub1-P-26 (3.1 g, 10 mmol) and Sub2-P-2 (4.4 g, 10 mmol) were used to obtain a product (4.8 g, 67%) using the synthesis method of P-1.

7. Synthesis Example of P-123

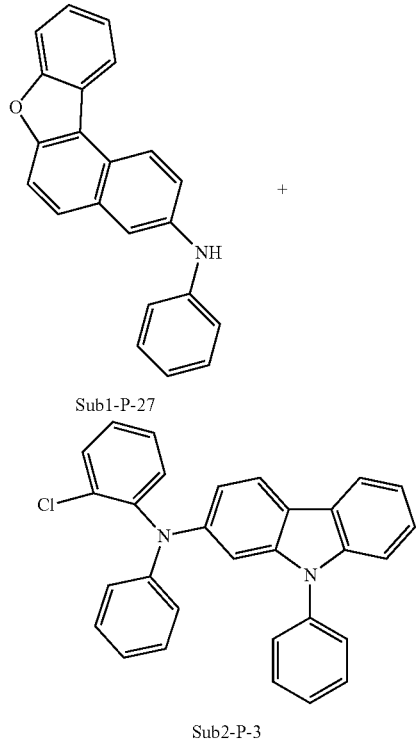

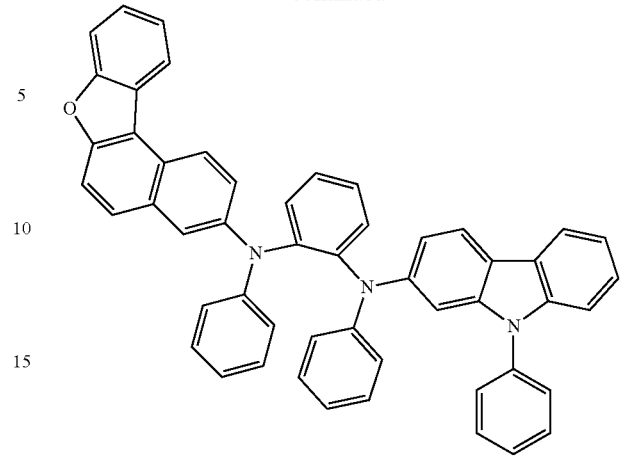

Sub1-P-27 (3.1 g, 10 mmol) and Sub2-P-3 (4.4 g, 10 mmol) were used to obtain a product (4 g, 56%) using the synthesis method of P-1.

Meanwhile, FD-MS values of the compounds P-1 to P-128 of the present invention prepared according to the synthesis example as described above are shown in Table 3.

TABLE 3

| compound | FD-MS | compound | FD-MS |
|---|---|---|---|
| P-1 | m/z = 717.28($C_{52}H_{35}N_3O$ = 717.87) | P-2 | m/z = 717.28($C_{52}H_{35}N_3O$ = 717.87) |
| P-3 | m/z = 717.28($C_{52}H_{35}N_3O$ = 717.87) | P-4 | m/z = 717.28($C_{52}H_{35}N_3O$ = 717.87) |
| P-5 | m/z = 717.28($C_{52}H_{35}N_3O$ = 717.87) | P-6 | m/z = 717.28($C_{52}H_{35}N_3O$ = 717.87) |
| P-7 | m/z = 717.28($C_{52}H_{35}N_3O$ = 717.87) | P-8 | m/z = 717.28($C_{52}H_{35}N_3O$ = 717.87) |
| P-9 | m/z = 717.28($C_{52}H_{35}N_3O$ = 717.87) | P-10 | m/z = 717.28($C_{52}H_{35}N_3O$ = 717.87) |
| P-11 | m/z = 793.31($C_{56}H_{39}N_3O$ = 793.97) | P-12 | m/z = 793.31($C_{56}H_{39}N_3O$ = 793.97) |
| P-13 | m/z = 772.33($C_{56}H_{32}D_5N_3O$ = 772.96) | P-14 | m/z = 767.29($C_{56}H_{37}N_3O$ = 767.93) |
| P-15 | m/z = 807.29($C_{58}H_{37}N_3O_2$ = 807.95) | P-16 | m/z = 823.27($C_{58}H_{37}N_3OS$ = 824.01) |
| P-17 | m/z = 833.34($C_{61}H_{43}N_3O$ = 834.04) | P-18 | m/z = 882.34($C_{64}H_{42}N_4O$ = 883.07) |
| P-19 | m/z = 767.29($C_{56}H_{37}N_3O$ = 767.93) | P-20 | m/z = 869.34($C_{64}H_{43}N_3O$ = 870.07) |
| P-21 | m/z = 717.28($C_{52}H_{35}N_3O$ = 717.87) | P-22 | m/z = 733.26($C_{52}H_{35}N_3S$ = 733.93) |
| P-23 | m/z = 717.28($C_{52}H_{35}N_3O$ = 717.87) | P-24 | m/z = 717.28($C_{52}H_{35}N_3O$ = 717.87) |
| P-25 | m/z = 733.26($C_{52}H_{35}N_3S$ = 733.93) | P-26 | m/z = 717.28($C_{52}H_{35}N_3O$ = 717.87) |
| P-27 | m/z = 717.28($C_{52}H_{35}N_3O$ = 717.87) | P-28 | m/z = 717.28($C_{52}H_{35}N_3O$ = 717.87) |
| P-29 | m/z = 717.28($C_{52}H_{35}N_3O$ = 717.87) | P-30 | m/z = 733.26($C_{52}H_{35}N_3S$ = 733.93) |
| P-31 | m/z = 717.28($C_{52}H_{35}N_3O$ = 717.87) | P-32 | m/z = 733.26($C_{52}H_{35}N_3S$ = 733.93) |
| P-33 | m/z = 717.28($C_{52}H_{35}N_3O$ = 717.87) | P-34 | m/z = 717.28($C_{52}H_{35}N_3O$ = 717.87) |
| P-35 | m/z = 733.26($C_{52}H_{35}N_3S$ = 733.93) | P-36 | m/z = 717.28($C_{52}H_{35}N_3O$ = 717.87) |
| P-37 | m/z = 793.31($C_{58}H_{39}N_3O$ = 793.97) | P-38 | m/z = 793.31($C_{58}H_{39}N_3O$ = 793.97) |
| P-39 | m/z = 809.29($C_{58}H_{39}N_3S$ = 810.03) | P-40 | m/z = 893.34($C_{66}H_{43}N_3O$ = 894.09) |
| P-41 | m/z = 733.26($C_{52}H_{35}N_3S$ = 733.93) | P-42 | m/z = 733.26($C_{52}H_{35}N_3S$ = 733.93) |
| P-43 | m/z = 769.24($C_{52}H_{33}F_2N_3S$ = 769.91) | P-44 | m/z = 733.26($C_{52}H_{35}N_3S$ = 733.93) |
| P-45 | m/z = 733.26($C_{52}H_{35}N_3S$ = 733.93) | P-46 | m/z = 783.27($C_{56}H_{37}N_3S$ = 783.99) |
| P-47 | m/z = 783.27($C_{56}H_{37}N_3S$ = 783.99) | P-48 | m/z = 733.26($C_{52}H_{35}N_3S$ = 733.93) |
| P-49 | m/z = 733.26($C_{52}H_{35}N_3S$ = 733.93) | P-50 | m/z = 733.26($C_{52}H_{35}N_3S$ = 733.93) |
| P-51 | m/z = 809.29($C_{58}H_{39}N_3S$ = 810.03) | P-52 | m/z = 859.3($C_{62}H_{41}N_3S$ = 860.09) |
| P-53 | m/z = 859.3($C_{62}H_{41}N_3S$ = 860.09) | P-54 | m/z = 858.28($C_{61}H_{38}N_4S$ = 859.06) |
| P-55 | m/z = 973.35($C_{71}H_{47}N_3S$ = 974.24) | P-56 | m/z = 859.3($C_{62}H_{41}N_3S$ = 860.09) |
| P-57 | m/z = 857.29($C_{62}H_{39}N_3S$ = 858.08) | P-58 | m/z = 885.32($C_{64}H_{43}N_3S$ = 886.13) |
| P-59 | m/z = 809.29($C_{58}H_{39}N_3S$ = 810.03) | P-60 | m/z = 809.29($C_{58}H_{39}N_3S$ = 810.03) |
| P-61 | m/z = 717.28($C_{52}H_{35}N_3O$ = 717.87) | P-62 | m/z = 717.28($C_{52}H_{35}N_3O$ = 717.87) |
| P-63 | m/z = 717.28($C_{52}H_{35}N_3O$ = 717.87) | P-64 | m/z = 717.28($C_{52}H_{35}N_3O$ = 717.87) |
| P-65 | m/z = 717.28($C_{52}H_{35}N_3O$ = 717.87) | P-66 | m/z = 717.28($C_{52}H_{35}N_3O$ = 717.87) |
| P-67 | m/z = 717.28($C_{52}H_{35}N_3O$ = 717.87) | P-68 | m/z = 717.28($C_{52}H_{35}N_3O$ = 717.87) |
| P-69 | m/z = 745.31($C_{54}H_{39}N_3O$ = 745.93) | P-70 | m/z = 717.28($C_{52}H_{35}N_3O$ = 717.87) |
| P-71 | m/z = 1047.38($C_{77}H_{49}N_3O_2$ = 1048.26) | P-72 | m/z = 807.29($C_{58}H_{37}N_3O_2$ = 807.95) |

TABLE 3-continued

| compound | FD-MS | compound | FD-MS |
|---|---|---|---|
| P-73 | m/z = 767.29($C_{56}H_{37}N_3O$ = 767.93) | P-74 | m/z = 767.29($C_{56}H_{37}N_3O$ = 767.93) |
| P-75 | m/z = 833.34($C_{61}H_{43}N_3O$ = 834.04) | P-76 | m/z = 807.29($C_{58}H_{37}N_3O_2$ = 807.95) |
| P-77 | m/z = 767.29($C_{56}H_{37}N_3O$ = 767.93) | P-78 | m/z = 843.32($C_{62}H_{41}N_3O$ = 844.03) |
| P-79 | m/z = 882.34($C_{64}H_{42}N_4O$ = 883.07) | P-80 | m/z = 793.31($C_{58}H_{39}N_3O$ = 793.97) |
| P-81 | m/z = 793.31($C_{58}H_{39}N_3O$ = 793.97) | P-82 | m/z = 717.28($C_{52}H_{35}N_3O$ = 717.87) |
| P-83 | m/z = 717.28($C_{52}H_{35}N_3O$ = 717.87) | P-84 | m/z = 717.28($C_{52}H_{35}N_3O$ = 717.87) |
| P-85 | m/z = 717.28($C_{52}H_{35}N_3O$ = 717.87) | P-86 | m/z = 717.28($C_{52}H_{35}N_3O$ = 717.87) |
| P-87 | m/z = 717.28($C_{52}H_{35}N_3O$ = 717.87) | P-88 | m/z = 717.28($C_{52}H_{35}N_3O$ = 717.87) |
| P-89 | m/z = 717.28($C_{52}H_{35}N_3O$ = 717.87) | P-90 | m/z = 717.28($C_{52}H_{35}N_3O$ = 717.87) |
| P-91 | m/z = 717.28($C_{52}H_{35}N_3O$ = 717.87) | P-92 | m/z = 717.28($C_{52}H_{35}N_3O$ = 717.87) |
| P-93 | m/z = 733.26($C_{52}H_{35}N_3S$ = 733.93) | P-94 | m/z = 733.26($C_{52}H_{35}N_3S$ = 733.93) |
| P-95 | m/z = 733.26($C_{52}H_{35}N_3S$ = 733.93) | P-96 | m/z = 867.36($C_{62}H_{49}N_3S$ = 868.16) |
| P-97 | m/z = 733.26($C_{52}H_{35}N_3S$ = 733.93) | P-98 | m/z = 733.26($C_{52}H_{35}N_3S$ = 733.93) |
| P-99 | m/z = 733.26($C_{52}H_{35}N_3S$ = 733.93) | P-100 | m/z = 733.26($C_{52}H_{35}N_3S$ = 733.93) |
| P-101 | m/z = 793.31($C_{58}H_{39}N_3O$ = 793.97) | P-102 | m/z = 793.31($C_{58}H_{39}N_3O$ = 793.97) |
| P-103 | m/z = 793.31($C_{58}H_{39}N_3O$ = 793.97) | P-104 | m/z = 859.3($C_{62}H_{41}N_3S$ = 860.09) |
| P-105 | m/z = 733.26($C_{52}H_{35}N_3S$ = 733.93) | P-106 | m/z = 733.26($C_{52}H_{35}N_3S$ = 733.93) |
| P-107 | m/z = 767.29($C_{56}H_{37}N_3O$ = 767.93) | P-108 | m/z = 733.26($C_{52}H_{35}N_3S$ = 733.93) |
| P-109 | m/z = 717.28($C_{52}H_{35}N_3O$ = 717.87) | P-110 | m/z = 733.26($C_{52}H_{35}N_3S$ = 733.93) |
| P-111 | m/z = 717.28($C_{52}H_{35}N_3O$ = 717.87) | P-112 | m/z = 733.26($C_{52}H_{35}N_3S$ = 733.93) |
| P-113 | m/z = 793.31($C_{58}H_{39}N_3O$ = 793.97) | P-114 | m/z = 793.31($C_{58}H_{39}N_3O$ = 793.97) |
| P-115 | m/z = 793.31($C_{58}H_{39}N_3O$ = 793.97) | P-116 | m/z = 843.32($C_{62}H_{41}N_3O$ = 844.03) |
| P-117 | m/z = 793.31($C_{58}H_{39}N_3O$ = 793.97) | P-118 | m/z = 733.26($C_{52}H_{35}N_3S$ = 733.93) |
| P-119 | m/z = 717.28($C_{52}H_{35}N_3O$ = 717.87) | P-120 | m/z = 733.26($C_{52}H_{35}N_3S$ = 733.93) |
| P-121 | m/z = 767.29($C_{56}H_{37}N_3O$ = 767.93) | P-122 | m/z = 783.27($C_{56}H_{37}N_3S$ = 783.99) |
| P-123 | m/z = 717.28($C_{52}H_{35}N_3O$ = 717.87) | P-124 | m/z = 783.27($C_{56}H_{37}N_3S$ = 783.99) |
| P-125 | m/z = 793.31($C_{58}H_{39}N_3O$ = 793.97) | P-126 | m/z = 793.31($C_{58}H_{39}N_3O$ = 793.97) |
| P-127 | m/z = 793.31($C_{58}H_{39}N_3O$ = 793.97) | P-128 | m/z = 793.31($C_{58}H_{39}N_3O$ = 793.97) |

Synthesis Example 2

The compound (final product 2) represented by Formula 2 according to the present invention may be prepared as shown in Scheme 4, but is not limited thereto.

<Reaction Scheme 4> ($Hal^4$ is I, Br, or Cl.)

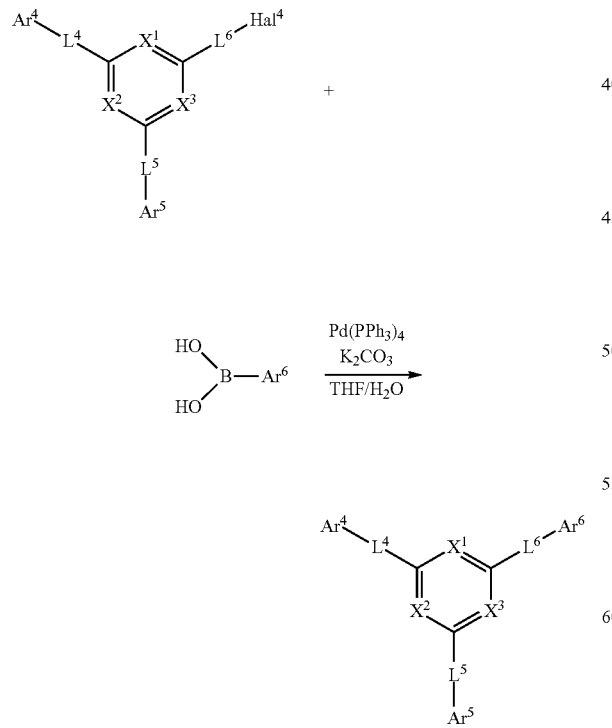

Final product 2

IV. Synthesis of Final Product 2

1. Synthesis Example of N-1

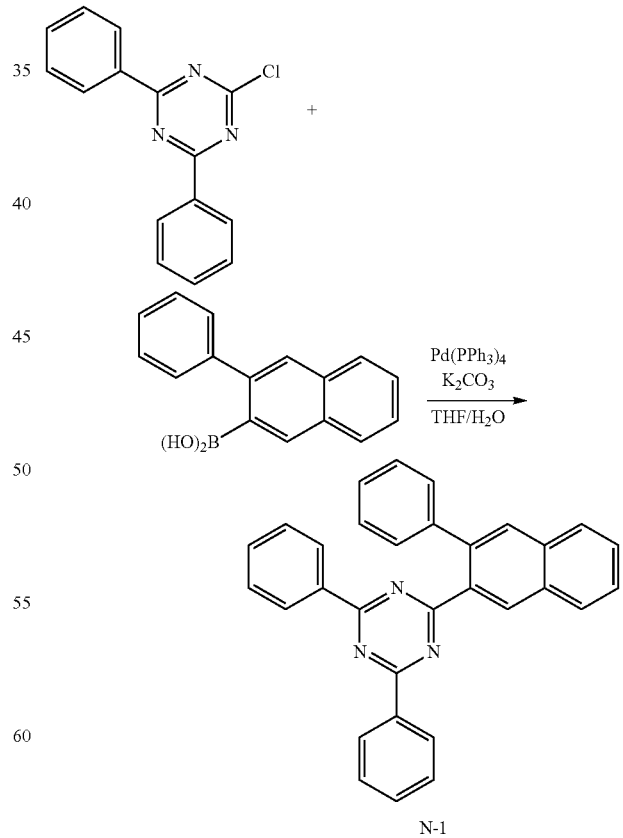

After placing 2-chloro-4,6-diphenyl-1,3,5-triazine (8 g, 30 mmol) and (3-phenylnaphthalen-2-yl)boronic acid (8.2 g, 33 mmol), K₂CO₃ (12.4 g, 90 mmol), Pd(PPh₃)₄ (1.7 g, 1.5 mmol) in a round bottom flask, THF and water were added to dissolve, and then refluxed at 80° C. for 12 hours. When the reaction was completed, the temperature of the reaction product was cooled to room temperature, extracted with CH₂Cl₂, and washed with water. The organic layer was dried over MgSO₄, concentrated, and the resulting organic material was separated using a silica gel column to obtain the desired product (9.54 g, 73%).

2. Synthesis Example of N-19

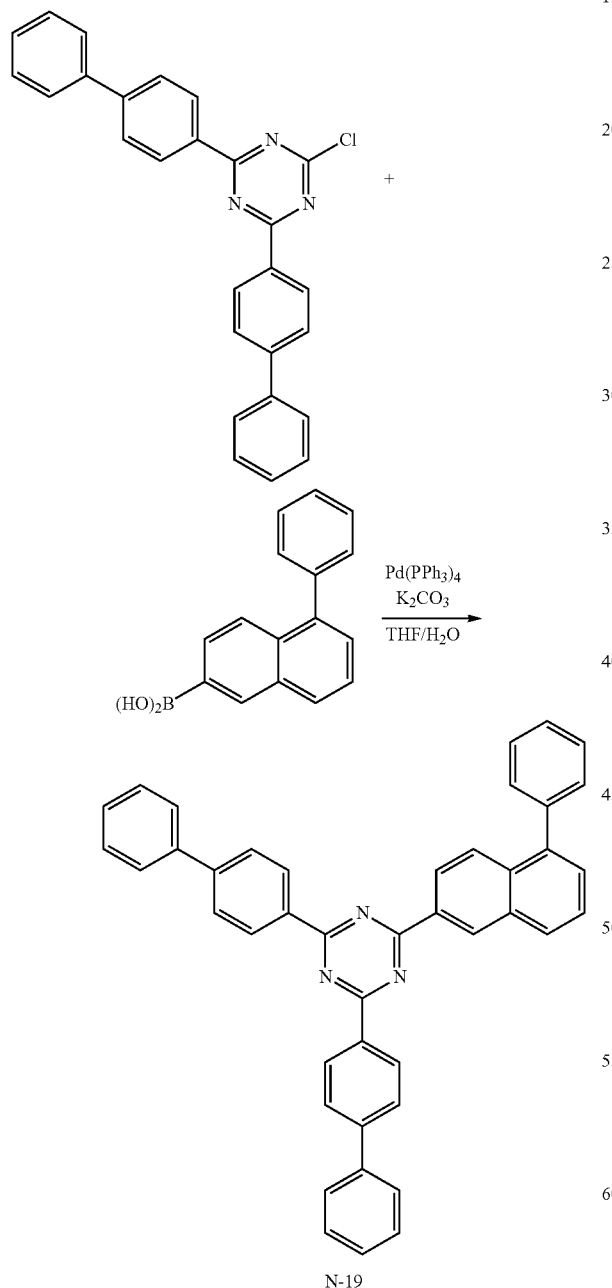

2,4-di([1,1'-biphenyl]-4-yl)-6-chloro-1,3,5-triazine (12.6 g, 30 mmol) and (5-phenylnaphthalen-2-yl)boronic acid (8.2 g, 33 mmol) were used to obtain a product (15.5 g, 88%) using the synthesis method of N-1.

3. Synthesis Example of N-33

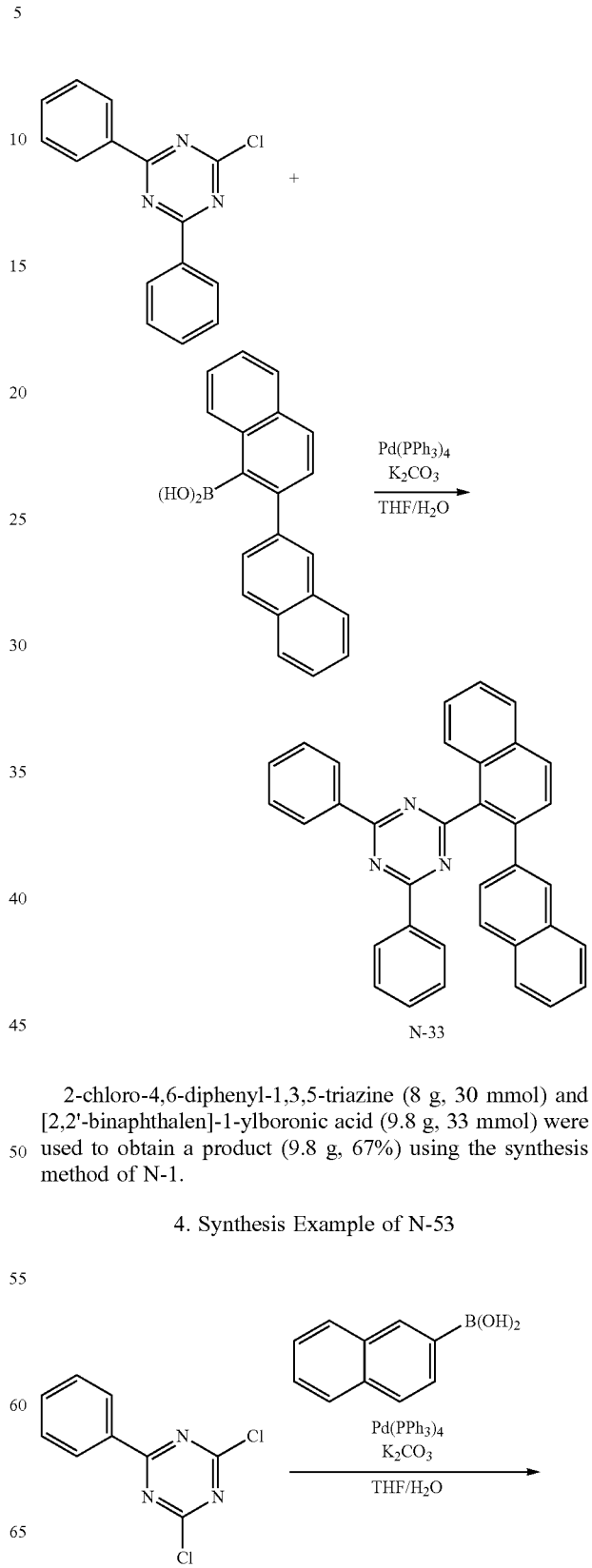

2-chloro-4,6-diphenyl-1,3,5-triazine (8 g, 30 mmol) and [2,2'-binaphthalen]-1-ylboronic acid (9.8 g, 33 mmol) were used to obtain a product (9.8 g, 67%) using the synthesis method of N-1.

4. Synthesis Example of N-53

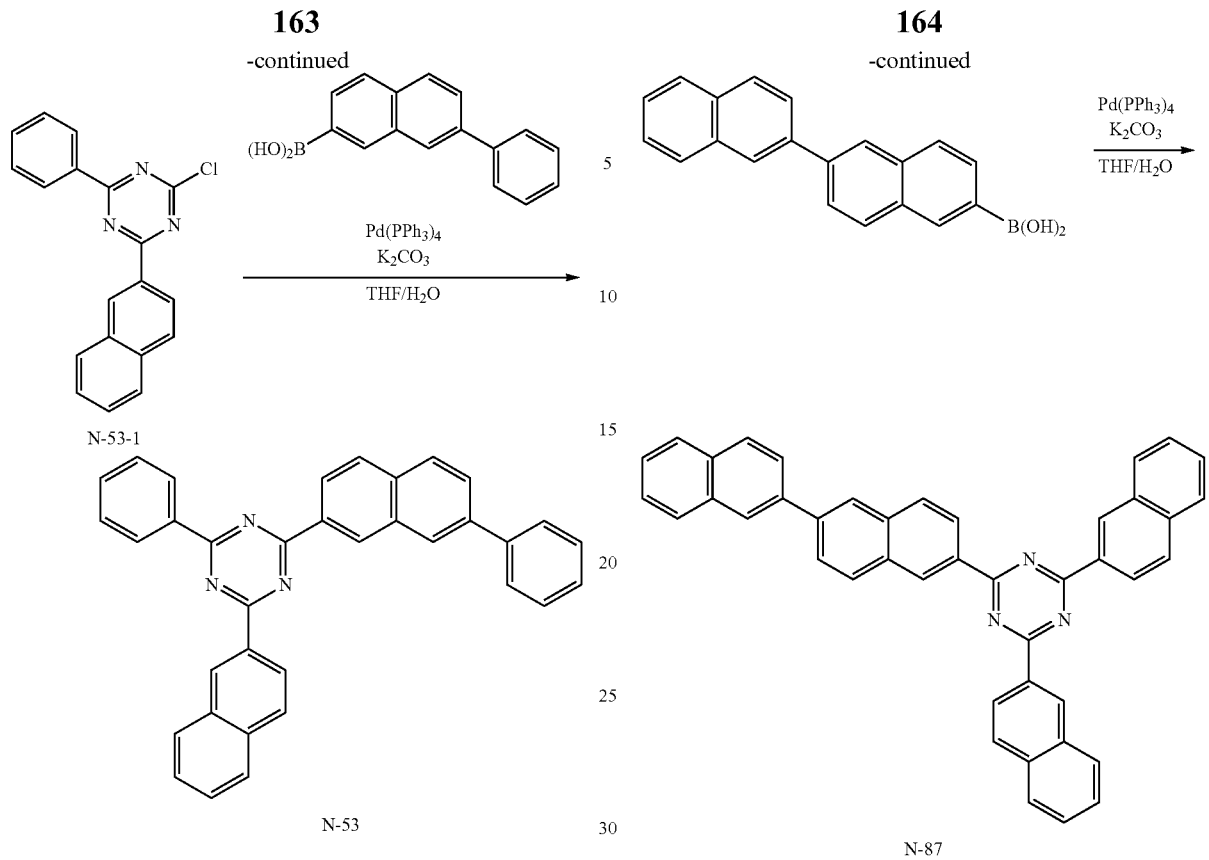

(1) Synthesis of N-53-1

2,4-dichloro-6-phenyl-1,3,5-triazine (6.8 g, 30 mmol) and naphthalen-2-ylboronic acid (5.1 g, 30 mmol) were used to obtain a product (6.7 g, 70%) using the synthesis method of N-1.

(2) Synthesis of N-53

2-chloro-4-(naphthalen-2-yl)-6-phenyl-1,3,5-triazine (9.5 g, 30 mmol) and (7-phenylnaphthalen-2-yl)boronic acid (8.2 g, 33 mmol) were used to obtain a product (12.4 g, 85%) using the synthesis method of N-1.

5. Synthesis Example of N-87

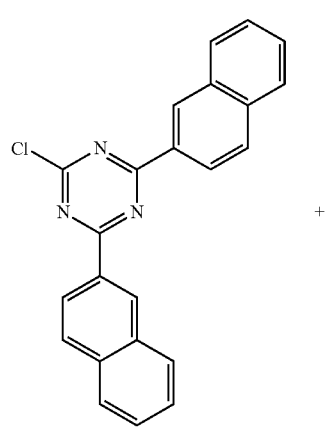

2-chloro-4,6-di(naphthalen-2-yl)-1,3,5-triazine (11 g, 30 mmol) and [2,2'-binaphthalen]-6-ylboronic acid (9.8 g, 33 mmol) were used to obtain a product (14.8 g, 84%) using the synthesis method of N-1.

6. Synthesis Example of N-113

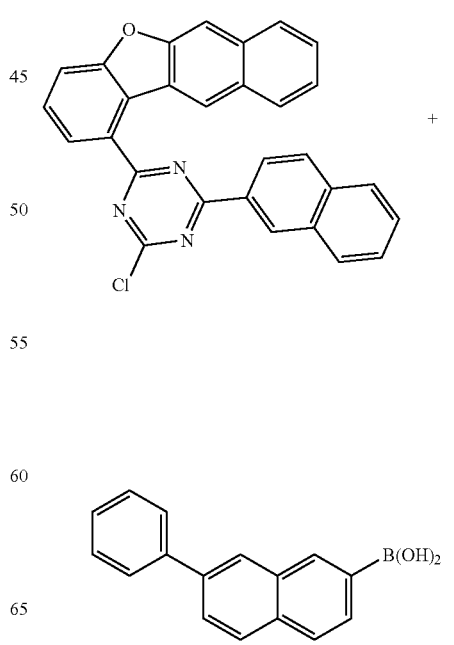

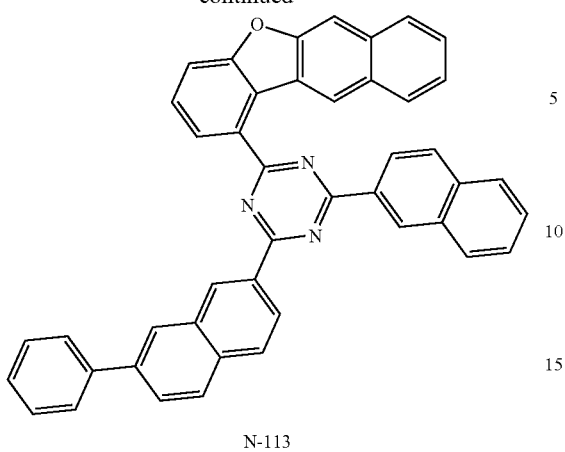

N-113

2-chloro-4-(naphthalen-2-yl)-6-(naphtho[2,3-b]benzofuran-1-yl)-1,3,5-triazine (13.7 g, 30 mmol) and (7-phenylnaphthalen-2-yl)boronic acid (8.2 g, 33 mmol) were used to obtain a product (14.5 g, 77%) using the synthesis method of N-1.

7. Synthesis Example of N-115

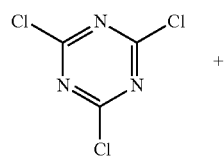

+

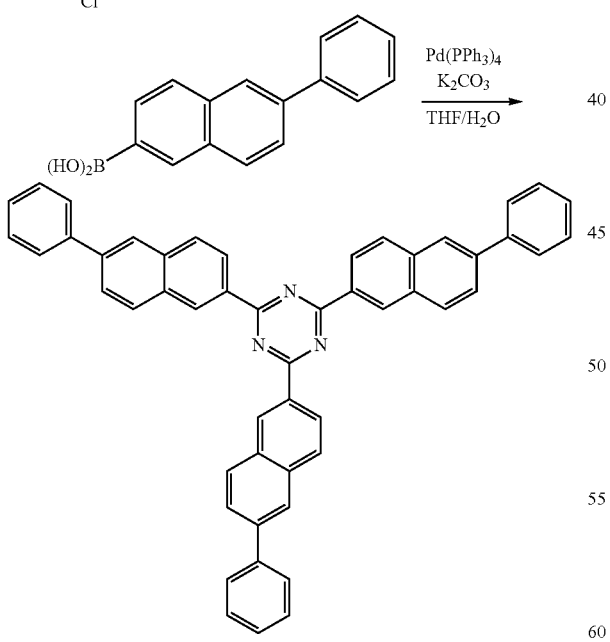

N-115

2,4,6-trichloro-1,3,5-triazine (5.5 g, 30 mmol) and (6-phenylnaphthalen-2-yl)boronic acid (23 g, 93 mmol) were used to obtain a product (15 g, 73%) using the synthesis method of N-1.

8. Synthesis Example of N-165

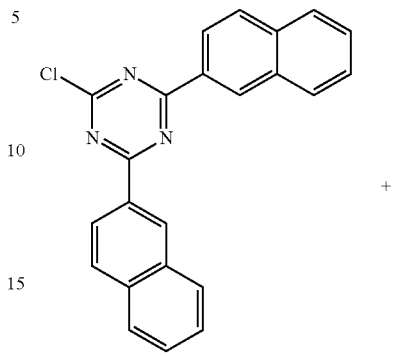

+

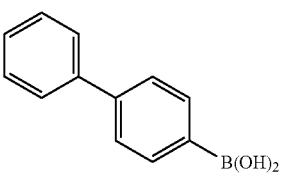

N-165

2-chloro-4,6-di(naphthalen-2-yl)-1,3,5-triazine (11 g, 30 mmol) and [1,1'-biphenyl]-4-ylboronic acid (5.9 g, 30 mmol) were used to obtain a product (11.9 g, 82%) using the synthesis method of N-1.

9. Synthesis Example of N-177

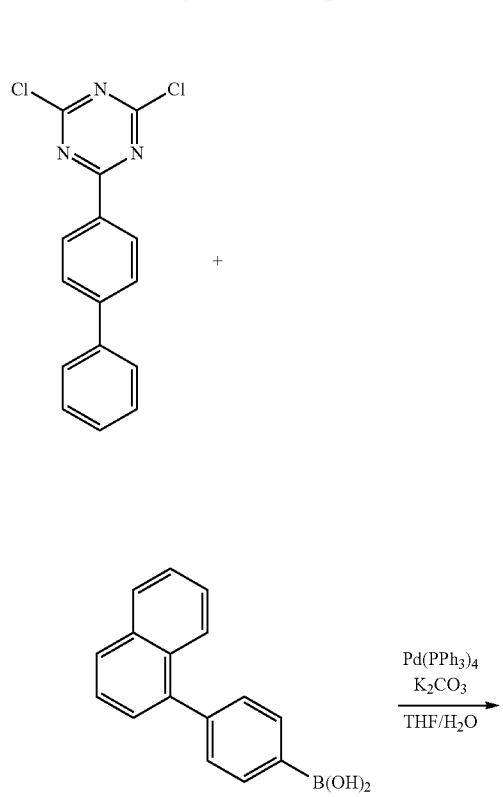

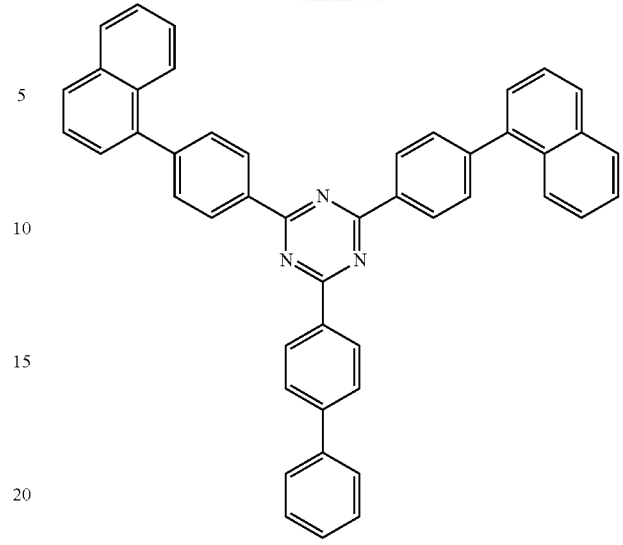

N-177

2-([1,1'-biphenyl]-4-yl)-4,6-dichloro-1,3,5-triazine (9 g, 30 mmol) and (4-(naphthalen-1-yl)phenyl)boronic acid (15.4 g, 62 mmol) were used to obtain a product (12.8 g, 67%) using the synthesis method of N-1.

Meanwhile, FD-MS values of compounds N-1 to N-148 of the present invention prepared according to the synthesis example as described above are shown in Table 4.

TABLE 4

| compound | FD-MS | compound | FD-MS |
|---|---|---|---|
| N-1 | m/z = 435.17($C_{31}H_{21}N_3$ = 435.53) | N-2 | m/z = 435.17($C_{31}H_{21}N_3$ = 435.53) |
| N-3 | m/z = 435.17($C_{31}H_{21}N_3$ = 435.53) | N-4 | m/z = 435.17($C_{31}H_{21}N_3$ = 435.53) |
| N-5 | m/z = 435.17($C_{31}H_{21}N_3$ = 435.53) | N-6 | m/z = 435.17($C_{31}H_{21}N_3$ = 435.53) |
| N-7 | m/z = 435.17($C_{31}H_{21}N_3$ = 435.53) | N-8 | m/z = 434.18($C_{32}H_{22}N_2$ = 434.54) |
| N-9 | m/z = 511.2($C_{37}H_{25}N_3$ = 511.63) | N-10 | m/z = 611.24($C_{45}H_{29}N_3$ = 611.75) |
| N-11 | m/z = 485.19($C_{35}H_{23}N_3$ = 485.59) | N-12 | m/z = 511.2($C_{37}H_{25}N_3$ = 511.63) |
| N-13 | m/z = 511.2($C_{37}H_{25}N_3$ = 511.63) | N-14 | m/z = 485.19($C_{35}H_{23}N_3$ = 485.59) |
| N-15 | m/z = 434.18($C_{32}H_{22}N_2$ = 434.54) | N-16 | m/z = 434.18($C_{32}H_{22}N_2$ = 434.54) |
| N-17 | m/z = 511.2($C_{37}H_{25}N_3$ = 511.63) | N-18 | m/z = 561.22($C_{41}H_{27}N_3$ = 561.69) |
| N-19 | m/z = 587.24($C_{43}H_{29}N_3$ = 587.73) | N-20 | m/z = 511.2($C_{37}H_{25}N_3$ = 511.63) |
| N-21 | m/z = 511.2($C_{37}H_{25}N_3$ = 511.63) | N-22 | m/z = 511.2($C_{37}H_{25}N_3$ = 511.63) |
| N-23 | m/z = 511.2($C_{37}H_{25}N_3$ = 511.63) | N-24 | m/z = 587.24($C_{43}H_{29}N_3$ = 587.73) |
| N-25 | m/z = 435.17($C_{31}H_{21}N_3$ = 435.53) | N-26 | m/z = 435.17($C_{31}H_{21}N_3$ = 435.53) |
| N-27 | m/z = 435.17($C_{31}H_{21}N_3$ = 435.53) | N-28 | m/z = 435.17($C_{31}H_{21}N_3$ = 435.53) |
| N-29 | m/z = 435.17($C_{31}H_{21}N_3$ = 435.53) | N-30 | m/z = 435.17($C_{31}H_{21}N_3$ = 435.53) |
| N-31 | m/z = 435.17($C_{31}H_{21}N_3$ = 435.53) | N-32 | m/z = 434.18($C_{32}H_{22}N_2$ = 434.54) |
| N-33 | m/z = 485.19($C_{35}H_{23}N_3$ = 485.59) | N-34 | m/z = 511.2($C_{37}H_{25}N_3$ = 511.63) |
| N-35 | m/z = 511.2($C_{37}H_{25}N_3$ = 511.63) | N-36 | m/z = 511.2($C_{37}H_{25}N_3$ = 511.63) |
| N-37 | m/z = 485.19($C_{35}H_{23}N_3$ = 485.59) | N-38 | m/z = 511.2($C_{37}H_{25}N_3$ = 511.63) |
| N-39 | m/z = 485.19($C_{35}H_{23}N_3$ = 485.59) | N-40 | m/z = 611.24($C_{45}H_{29}N_3$ = 611.75) |
| N-41 | m/z = 511.2($C_{37}H_{25}N_3$ = 511.63) | N-42 | m/z = 511.2($C_{37}H_{25}N_3$ = 511.63) |
| N-43 | m/z = 587.24($C_{43}H_{29}N_3$ = 587.73) | N-44 | m/z = 587.24($C_{43}H_{29}N_3$ = 587.73) |
| N-45 | m/z = 587.24($C_{43}H_{29}N_3$ = 587.73) | N-46 | m/z = 561.22($C_{41}H_{27}N_3$ = 561.69) |
| N-47 | m/z = 511.2($C_{37}H_{25}N_3$ = 511.63) | N-48 | m/z = 587.24($C_{43}H_{29}N_3$ = 587.73) |
| N-49 | m/z = 485.19($C_{35}H_{23}N_3$ = 485.59) | N-50 | m/z = 485.19($C_{35}H_{23}N_3$ = 485.59) |
| N-51 | m/z = 485.19($C_{35}H_{23}N_3$ = 485.59) | N-52 | m/z = 485.19($C_{35}H_{23}N_3$ = 485.59) |
| N-53 | m/z = 485.19($C_{35}H_{23}N_3$ = 485.59) | N-54 | m/z = 535.2($C_{39}H_{25}N_3$ = 535.65) |
| N-55 | m/z = 485.19($C_{35}H_{23}N_3$ = 485.59) | N-56 | m/z = 485.19($C_{35}H_{23}N_3$ = 485.59) |
| N-57 | m/z = 561.22($C_{41}H_{27}N_3$ = 561.69) | N-58 | m/z = 561.22($C_{41}H_{27}N_3$ = 561.69) |
| N-59 | m/z = 561.22($C_{41}H_{27}N_3$ = 561.69) | N-60 | m/z = 637.25($C_{47}H_{31}N_3$ = 637.79) |
| N-61 | m/z = 561.22($C_{41}H_{27}N_3$ = 561.69) | N-62 | m/z = 561.22($C_{41}H_{27}N_3$ = 561.69) |
| N-63 | m/z = 637.25($C_{47}H_{31}N_3$ = 637.79) | N-64 | m/z = 637.25($C_{47}H_{31}N_3$ = 637.79) |
| N-65 | m/z = 637.25($C_{47}H_{31}N_3$ = 637.79) | N-66 | m/z = 485.19($C_{35}H_{23}N_3$ = 485.59) |
| N-67 | m/z = 485.19($C_{35}H_{23}N_3$ = 485.59) | N-68 | m/z = 611.24($C_{45}H_{29}N_3$ = 611.75) |
| N-69 | m/z = 485.19($C_{35}H_{23}N_3$ = 485.59) | N-70 | m/z = 485.19($C_{35}H_{23}N_3$ = 485.59) |
| N-71 | m/z = 611.24($C_{45}H_{29}N_3$ = 611.75) | N-72 | m/z = 485.19($C_{35}H_{23}N_3$ = 485.59) |
| N-73 | m/z = 485.19($C_{35}H_{23}N_3$ = 485.59) | N-74 | m/z = 561.22($C_{41}H_{27}N_3$ = 561.69) |

TABLE 4-continued

| compound | FD-MS | compound | FD-MS |
|---|---|---|---|
| N-75 | m/z = 485.19($C_{35}H_{23}N_3$ = 485.59) | N-76 | m/z = 485.19($C_{35}H_{23}N_3$ = 485.59) |
| N-77 | m/z = 611.24($C_{45}H_{29}N_3$ = 611.75) | N-78 | m/z = 611.24($C_{45}H_{29}N_3$ = 611.75) |
| N-79 | m/z = 485.19($C_{35}H_{23}N_3$ = 485.59) | N-80 | m/z = 485.19($C_{35}H_{23}N_3$ = 485.59) |
| N-81 | m/z = 485.19($C_{35}H_{23}N_3$ = 485.59) | N-82 | m/z = 485.19($C_{35}H_{23}N_3$ = 485.59) |
| N-83 | m/z = 535.2($C_{39}H_{25}N_3$ = 535.65) | N-84 | m/z = 535.2($C_{39}H_{25}N_3$ = 535.65) |
| N-85 | m/z = 585.22($C_{43}H_{27}N_3$ = 585.71) | N-86 | m/z = 535.2($C_{39}H_{25}N_3$ = 535.65) |
| N-87 | m/z = 585.22($C_{43}H_{27}N_3$ = 585.71) | N-88 | m/z = 585.22($C_{43}H_{27}N_3$ = 585.71) |
| N-89 | m/z = 611.24($C_{45}H_{29}N_3$ = 611.75) | N-90 | m/z = 611.24($C_{45}H_{29}N_3$ = 611.75) |
| N-91 | m/z = 585.22($C_{43}H_{27}N_3$ = 585.71) | N-92 | m/z = 611.24($C_{45}H_{29}N_3$ = 611.75) |
| N-93 | m/z = 687.27($C_{51}H_{33}N_3$ = 687.85) | N-94 | m/z = 611.24($C_{45}H_{29}N_3$ = 611.75) |
| N-95 | m/z = 511.2($C_{37}H_{25}N_3$ = 511.63) | N-96 | m/z = 611.24($C_{45}H_{29}N_3$ = 611.75) |
| N-97 | m/z = 561.22($C_{41}H_{27}N_3$ = 561.69) | N-98 | m/z = 587.24($C_{43}H_{29}N_3$ = 587.73) |
| N-99 | m/z = 663.27($C_{49}H_{33}N_3$ = 663.82) | N-100 | m/z = 713.28($C_{53}H_{35}N_3$ = 713.88) |
| N-101 | m/z = 575.2($C_{41}H_{25}N_3O$ = 575.67) | N-102 | m/z = 601.22($C_{43}H_{27}N_3O$ = 601.71) |
| N-103 | m/z = 700.26($C_{51}H_{32}N_4$ = 700.85) | N-104 | m/z = 701.25($C_{51}H_{31}N_3O$ = 701.83) |
| N-105 | m/z = 667.21($C_{47}H_{29}N_3S$ = 667.83) | N-106 | m/z = 541.16($C_{37}H_{23}N_3S$ = 541.67) |
| N-107 | m/z = 612.23($C_{44}H_{28}N_4$ = 612.74) | N-108 | m/z = 562.22($C_{40}H_{26}N_4$ = 562.68) |
| N-109 | m/z = 689.26($C_{49}H_{31}N_5$ = 689.82) | N-110 | m/z = 639.24($C_{45}H_{29}N_5$ = 639.76) |
| N-111 | m/z = 701.25($C_{51}H_{31}N_3O$ = 701.83) | N-112 | m/z = 631.17($C_{43}H_{25}N_3OS$ = 631.75) |
| N-113 | m/z = 625.22($C_{45}H_{27}N_3O$ = 625.73) | N-114 | m/z = 591.18($C_{41}H_{25}N_3S$ = 591.73) |
| N-115 | m/z = 687.27($C_{51}H_{33}N_3$ = 687.85) | N-116 | m/z = 701.25($C_{51}H_{31}N_3O$ = 701.83) |
| N-117 | m/z = 619.3($C_{45}H_{37}N_3$ = 619.81) | N-118 | m/z = 601.25($C_{44}H_{31}N_3$ = 601.75) |
| N-119 | m/z = 667.23($C_{47}H_{29}N_3O_2$ = 667.77) | N-120 | m/z = 540.24($C_{39}H_{20}D_5N_3$ = 540.68) |
| N-121 | m/z = 521.17($C_{35}H_{21}F_2N_3$ = 521.57) | N-122 | m/z = 510.18($C_{36}H_{22}N_4$ = 510.6) |
| N-123 | m/z = 652.23($C_{46}H_{28}N_4O$ = 652.76) | N-124 | m/z = 527.24($C_{38}H_{29}N_3$ = 527.67) |
| N-125 | m/z = 535.2($C_{39}H_{25}N_3$ = 535.65) | N-126 | m/z = 535.2($C_{39}H_{25}N_3$ = 535.65) |
| N-127 | m/z = 535.2($C_{39}H_{25}N_3$ = 535.65) | N-128 | m/z = 535.2($C_{39}H_{25}N_3$ = 535.65) |
| N-129 | m/z = 587.24($C_{43}H_{29}N_3$ = 587.73) | N-130 | m/z = 612.23($C_{44}H_{28}N_4$ = 612.74) |
| N-131 | m/z = 561.22($C_{41}H_{27}N_3$ = 561.69) | N-132 | m/z = 687.27($C_{51}H_{33}N_3$ = 687.85) |
| N-133 | m/z = 663.27($C_{49}H_{33}N_3$ = 663.82) | N-134 | m/z = 601.22($C_{43}H_{27}N_3O$ = 601.71) |
| N-135 | m/z = 617.19($C_{43}H_{27}N_3S$ = 617.77) | N-136 | m/z = 752.29($C_{55}H_{36}N_4$ = 752.92) |
| N-137 | m/z = 651.23($C_{47}H_{29}N_3O$ = 651.77) | N-138 | m/z = 677.25($C_{49}H_{31}N_3O$ = 677.81) |
| N-139 | m/z = 541.16($C_{37}H_{23}N_3S$ = 541.67) | N-140 | m/z = 750.28($C_{55}H_{34}N_4$ = 750.91) |
| N-141 | m/z = 707.24($C_{59}H_{33}N_3S$ = 707.9) | N-142 | m/z = 651.23($C_{47}H_{29}N_3O$ = 651.77) |
| N-143 | m/z = 617.19($C_{43}H_{27}N_3S$ = 617.77) | N-144 | m/z = 667.21($C_{47}H_{29}N_3S$ = 667.83) |
| N-145 | m/z = 631.17($C_{43}H_{25}N_3OS$ = 631.75) | N-146 | m/z = 767.26($C_{55}H_{33}N_3O_2$ = 767.89) |
| N-147 | m/z = 647.15($C_{43}H_{25}N_3S_2$ = 647.81) | N-148 | m/z = 690.24($C_{49}H_{30}N_4O$ = 690.81) |
| N-149 | m/z = 511.2($C_{37}H_{25}N_3$ = 511.63) | N-150 | m/z = 587.24($C_{43}H_{29}N_3$ = 587.73) |
| N-151 | m/z = 511.2($C_{37}H_{25}N_3$ = 511.63) | N-152 | m/z = 511.2($C_{37}H_{25}N_3$ = 511.63) |
| N-153 | m/z = 511.2($C_{37}H_{25}N_3$ = 511.63) | N-154 | m/z = 511.2($C_{37}H_{25}N_3$ = 511.63) |
| N-155 | m/z = 511.2($C_{37}H_{25}N_3$ = 511.63) | N-156 | m/z = 561.22($C_{41}H_{27}N_3$ = 561.69) |
| N-157 | m/z = 485.19($C_{35}H_{23}N_3$ = 485.59) | N-158 | m/z = 561.22($C_{41}H_{27}N_3$ = 561.69) |
| N-159 | m/z = 611.24($C_{45}H_{29}N_3$ = 611.75) | N-160 | m/z = 561.22($C_{41}H_{27}N_3$ = 561.69) |
| N-161 | m/z = 535.2($C_{39}H_{25}N_3$ = 535.65) | N-162 | m/z = 561.22($C_{41}H_{27}N_3$ = 561.69) |
| N-163 | m/z = 611.24($C_{45}H_{29}N_3$ = 611.75) | N-164 | m/z = 561.22($C_{41}H_{27}N_3$ = 561.69) |
| N-165 | m/z = 485.19($C_{35}H_{23}N_3$ = 485.59) | N-166 | m/z = 561.22($C_{41}H_{27}N_3$ = 561.69) |
| N-167 | m/z = 611.24($C_{45}H_{29}N_3$ = 611.75) | N-168 | m/z = 561.22($C_{41}H_{27}N_3$ = 561.69) |
| N-169 | m/z = 485.19($C_{35}H_{23}N_3$ = 485.59) | N-170 | m/z = 561.22($C_{41}H_{27}N_3$ = 561.69) |
| N-171 | m/z = 535.2($C_{39}H_{25}N_3$ = 535.65) | N-172 | m/z = 535.2($C_{39}H_{25}N_3$ = 535.65) |
| N-173 | m/z = 561.22($C_{41}H_{27}N_3$ = 561.69) | N-174 | m/z = 637.25($C_{47}H_{31}N_3$ = 637.79) |
| N-175 | m/z = 587.24($C_{43}H_{29}N_3$ = 587.73) | N-176 | m/z = 687.27($C_{51}H_{33}N_3$ = 687.85) |
| N-177 | m/z = 637.25($C_{47}H_{31}N_3$ = 637.79) | N-178 | m/z = 561.22($C_{41}H_{27}N_3$ = 561.69) |
| N-179 | m/z = 499.17($C_{35}H_{21}N_3O$ = 499.57) | N-180 | m/z = 541.16($C_{37}H_{23}N_3S$ = 541.67) |
| N-181 | m/z = 611.24($C_{45}H_{29}N_3$ = 611.75) | N-182 | m/z = 687.27($C_{51}H_{33}N_3$ = 687.85) |
| N-183 | m/z = 676.26($C_{49}H_{32}N_4$ = 676.82) | N-184 | m/z = 525.22($C_{38}H_{27}N_3$ = 525.66) |

Evaluation of Manufacture of Organic Light Emitting Diode

[Example 1] to [Example 30] Manufacture and Evaluation of Red Organic Light Emitting Diode (Emitting Layer Mixed Phosphorescent Host)

First, on an ITO layer (anode) formed on a glass substrate, 4,4',4''-Tris[2-naphthyl(phenyl)amino]triphenylamine (hereinafter will be abbreviated as 2-TNATA) film was vacuum-deposited as a hole injection layer to form a thickness of 60 nm. Subsequently, N,N'-Bis(1-naphthalenyl)-N,N'-bis-phenyl-(1,1'-biphenyl)-4,4'-diamine (hereinafter abbreviated as NPB) was vacuum deposited to form a hole transport layer with a thickness of 60 nm.

The compound of the present invention (described in Table 5) represented by Formula 1 (first host compound) and Formula 2 (second host compound) as a host on the hole transport layer was mixed at 5:5, and as the dopant, an emitting layer having a thickness of 30 nm was deposited on the hole transport layer by doping (piq)2Ir(acac) [bis-(1-phenylisoquinolyl) iridium(III)acetylacetonate] with 5% weight.

(1,1'-bisphenyl)-4-oleato)bis(2-methyl-8-quinolinoleato) aluminum (abbreviated as BAlq) was vacuum deposited to a thickness of 10 nm as a hole blocking layer, and Tris(8-hydroxyquinolinato)aluminium (abbreviated as Alq3) was deposited to a thickness of 40 nm as an electron transport layer. Thereafter, as an electron injection layer, LiF, an alkali metal halide, was deposited to a thickness of 0.2 nm, subsequently, Al was deposited to a thickness of 150 nm and used as a cathode to manufacture an organic electronic element.

Comparative Example 1

An organic electronic element was manufactured in the same manner as in Example 1, except that Comparative Compound 2 was used as a single host.

Comparative Example 2 and Comparative Example 3

An organic electronic element was manufactured in the same manner as in Example 1, except that either P-81 or N-91 was used as a single host.

Comparative Example 4

An organic electronic element was manufactured in the same manner as in Example 1, except that Comparative Compound 1 and Comparative Compound 3 were mixed and used as a host.

Comparative Example 5

An organic electronic element was manufactured in the same manner as in Example 1, except that Comparative Compound 2 and N-137 were mixed and used as a host.

Comparative Example 6

An organic electronic element was manufactured in the same manner as in Example 1, except that P-81 and Comparative Compound 3 were mixed and used as a host.

Comparative example 1

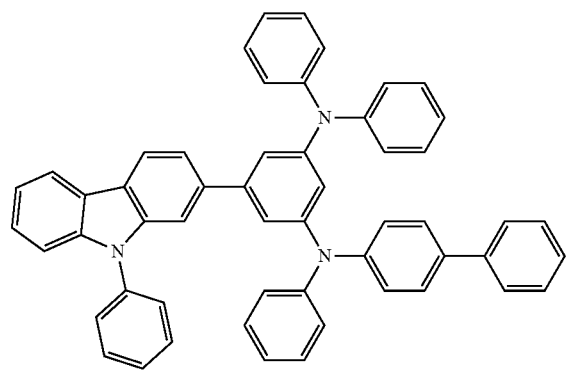

Comparative example 2

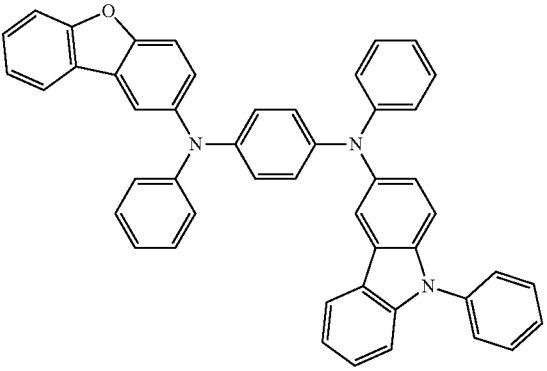

Commparative example 3

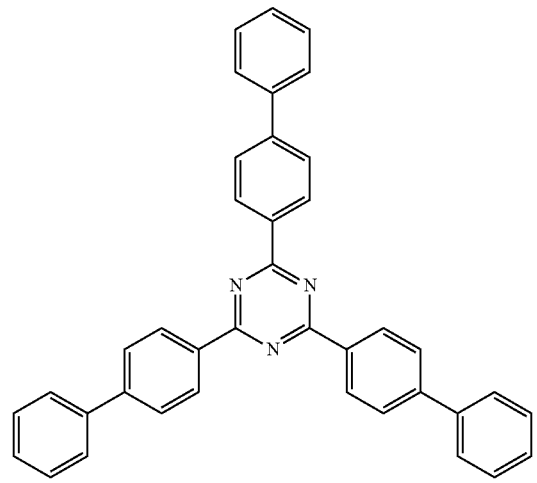

TABLE 5

| | First compound | Second compound | Voltage | Current Density (mA/cm$^2$) | Brightness (cd/m$^2$) | Efficiency (cd/A) | Lifespan |
|---|---|---|---|---|---|---|---|
| comparative example 1 | comparative compound2 | — | 6.3 | 22.3 | 2500.0 | 11.2 | 49.8 |
| comparative example 2 | P-81 | — | 6.1 | 18.0 | 2500.0 | 13.9 | 55.4 |
| comparative example 3 | N-91 | — | 5.9 | 17.2 | 2500.0 | 14.5 | 63.0 |
| comparative example 4 | comparative compound1 | comparative compound3 | 5.7 | 11.5 | 2500.0 | 21.6 | 57.1 |
| comparative example 5 | comparative compound2 | N-137 | 5.7 | 8.7 | 2500.0 | 28.6 | 71.9 |
| comparative example 6 | P-81 | comparative compound3 | 5.5 | 10.5 | 2500.0 | 23.9 | 75.9 |
| example1 | P-24 | N-65 | 5.2 | 7.0 | 2500.0 | 35.9 | 122.1 |
| example2 | P-82 | N-65 | 5.0 | 6.4 | 2500.0 | 38.8 | 130.7 |
| example3 | P-95 | N-65 | 5.1 | 6.9 | 2500.0 | 36.3 | 124.3 |
| example4 | P-114 | N-65 | 5.2 | 7.2 | 2500.0 | 34.9 | 122.2 |
| example5 | P-117 | N-65 | 5.1 | 7.0 | 2500.0 | 35.8 | 111.4 |

TABLE 5-continued

| | First compound | Second compound | Voltage | Current Density (mA/cm$^2$) | Brightness (cd/m$^2$) | Efficiency (cd/A) | Lifespan |
|---|---|---|---|---|---|---|---|
| example6 | P-24 | N-86 | 5.1 | 6.9 | 2500.0 | 36.4 | 113.5 |
| example7 | P-82 | N-86 | 4.9 | 6.2 | 2500.0 | 40.5 | 125.3 |
| example8 | P-95 | N-86 | 4.9 | 6.3 | 2500.0 | 39.4 | 123.1 |
| example9 | P-114 | N-86 | 5.0 | 6.5 | 2500.0 | 38.6 | 117.6 |
| example10 | P-117 | N-86 | 4.9 | 6.3 | 2500.0 | 39.9 | 105.9 |
| example11 | P-24 | N-93 | 5.0 | 7.0 | 2500.0 | 35.6 | 107.0 |
| example12 | P-82 | N-93 | 4.9 | 6.2 | 2500.0 | 40.6 | 117.2 |
| example13 | P-95 | N-93 | 5.0 | 6.3 | 2500.0 | 39.9 | 115.2 |
| example14 | P-114 | N-93 | 5.0 | 6.6 | 2500.0 | 38.0 | 105.3 |
| example15 | P-117 | N-93 | 5.0 | 6.4 | 2500.0 | 38.9 | 104.0 |
| example16 | P-24 | N-113 | 5.1 | 6.6 | 2500.0 | 37.8 | 120.4 |
| example17 | P-82 | N-113 | 4.9 | 6.1 | 2500.0 | 41.0 | 124.0 |
| example18 | P-95 | N-113 | 5.0 | 6.3 | 2500.0 | 39.8 | 124.5 |
| example19 | P-114 | N-113 | 5.1 | 6.8 | 2500.0 | 36.7 | 120.5 |
| example20 | P-117 | N-113 | 5.0 | 6.3 | 2500.0 | 39.5 | 115.2 |
| example21 | P-24 | N-129 | 5.1 | 6.9 | 2500.0 | 36.2 | 118.0 |
| example22 | P-82 | N-129 | 4.9 | 6.2 | 2500.0 | 40.6 | 118.7 |
| example23 | P-95 | N-129 | 4.9 | 6.8 | 2500.0 | 36.8 | 116.5 |
| example24 | P-114 | N-129 | 5.0 | 7.3 | 2500.0 | 34.3 | 114.7 |
| example25 | P-117 | N-129 | 4.9 | 6.4 | 2500.0 | 38.9 | 107.0 |
| example26 | P-24 | N-158 | 5.1 | 6.2 | 2500.0 | 40.1 | 97.9 |
| example27 | P-82 | N-158 | 4.8 | 5.9 | 2500.0 | 42.5 | 96.7 |
| example28 | P-95 | N-158 | 4.9 | 6.0 | 2500.0 | 41.8 | 97.6 |
| example29 | P-114 | N-158 | 5.1 | 6.4 | 2500.0 | 39.3 | 99.3 |
| example30 | P-117 | N-158 | 4.9 | 6.0 | 2500.0 | 41.7 | 99.3 |

As can be seen from the results of Table 5, when the material for an organic electroluminescent device of the present invention represented by Formula 1 and Formula 2 is mixed and used as a phosphorescent host (example 1-30); the efficiency and lifespan were significantly improved compared to devices using a single material (Comparative Examples 1-3) or devices mixed with a comparative compound (Comparative Examples 4-6).

That is, the device characteristics of Comparative Examples 4 to 6 used as a host by mixing two kinds of compounds were improved compared to the device characteristics of Comparative Examples 2 and 3 in which the compound of the present invention represented by Formula 1 or Formula 2 was used as a single host respectively, and in the case of the present invention using a mixture of substances corresponding to Formulas 1 and 2 of the present invention as a host, the efficiency and lifespan are significantly improved rather than Comparative Examples 4 to 6, When using a mixture as in the present invention, not only electrons and holes are moved through the energy level of each material, but also efficiency and lifespan are increased due to movement or energy transfer of electrons and holes due to mixing. As a result, when the compound represented by Formula 1 having fast hole characteristics and the compound represented by Formula 2 having strong electronic properties are mixed and used as a host, as in the present invention, the characteristics of the device are maximized because of a good electrochemical synergy effect.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

BRIEF DESCRIPTION OF THE DRAWINGS

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |

BRIEF DESCRIPTION OF THE DRAWINGS

| | |
|---|---|
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST1: second stack |

What is claimed is:

1. An organic electric element comprising a first electrode; a second electrode; and an organic material layer formed between the first electrode and the second electrode, wherein the organic material layer comprises an hole injection layer, an hole transport layer, an emitting auxiliary layer and an emitting layer, and wherein the emitting layer comprises a compound selected from the group consisting of the following compounds:

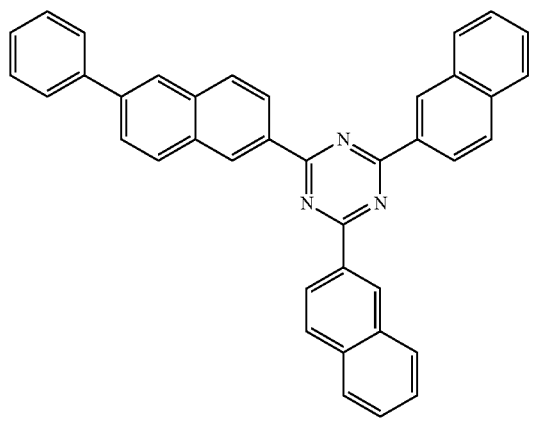

N-86

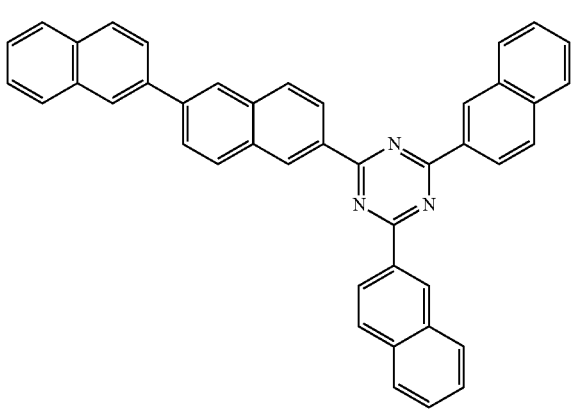

N-87

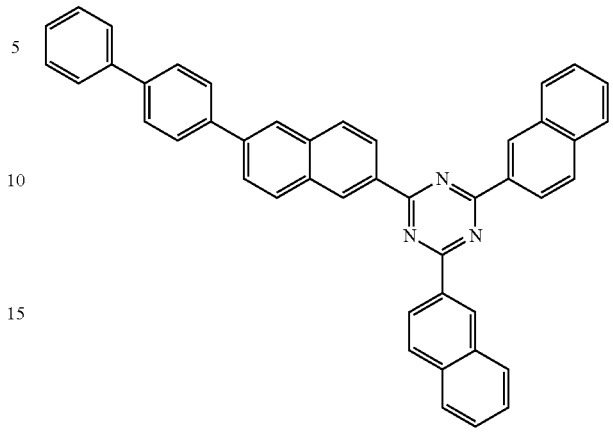

N-89

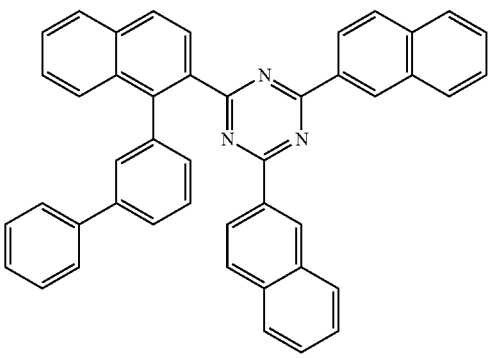

N-90

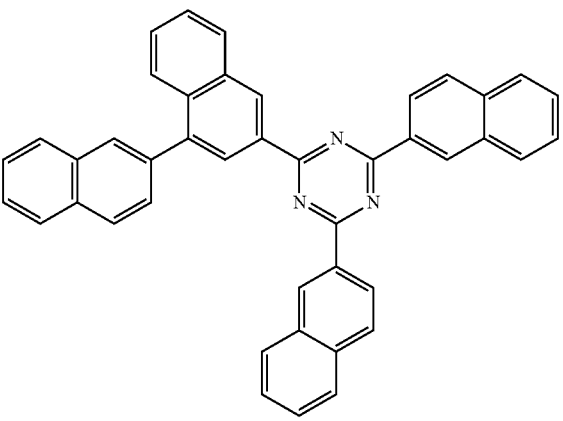

N-91

-continued
N-94
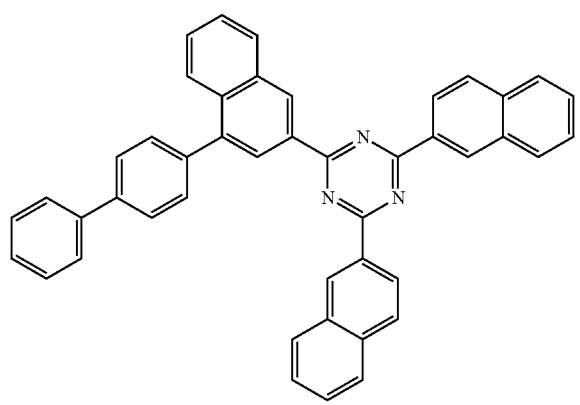
N-103
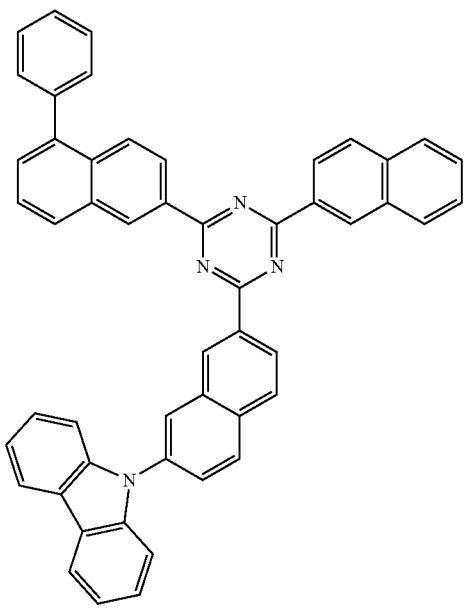
N-111
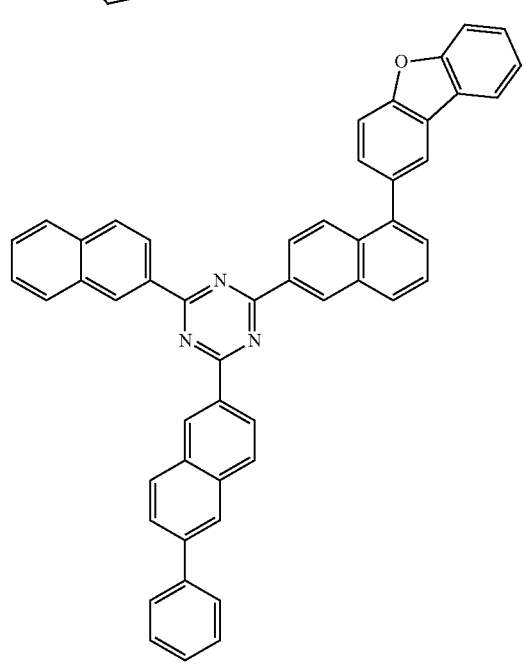
-continued
N-128
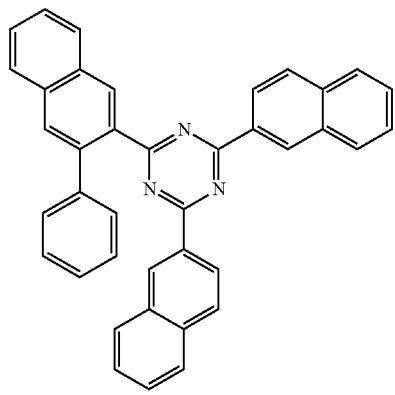
N-127
N-115
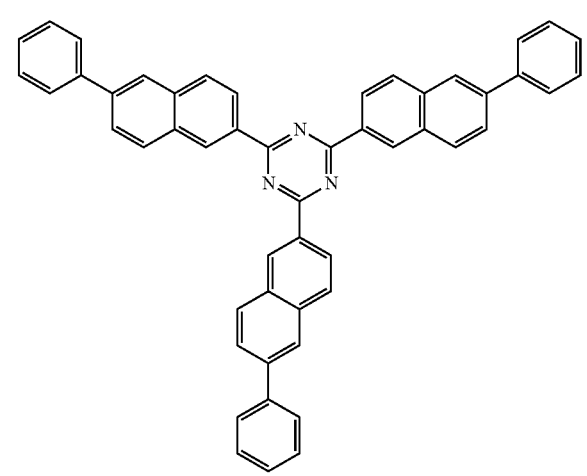

N-120

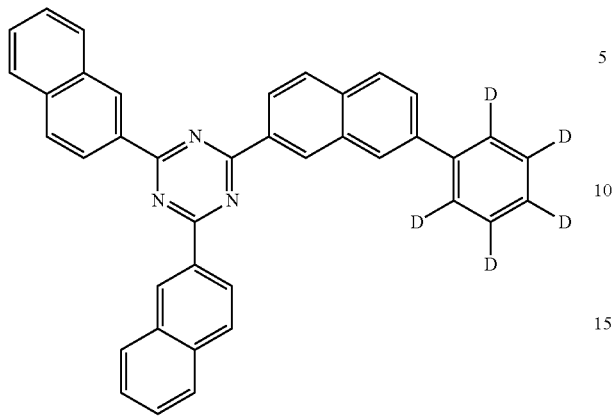

N-125

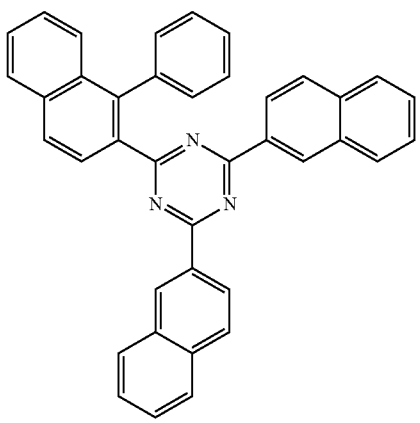

N-126

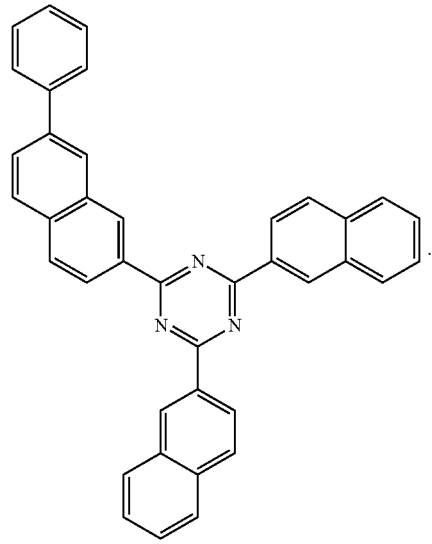

2. The organic electric element according to claim 1, further comprising a light efficiency enhancing layer formed on one side of the first electrode and/or one side of the second electrode, the side being located opposite to the organic material layer.

3. An electronic device comprising: a display device including the organic electronic element of claim 1; and a control unit for driving the display device.

4. The organic electronic device claim 3, wherein the organic electronic element is at least one of an OLED, an organic solar cell, an organic photo conductor, an organic transistor and an element for monochromic or white illumination.

\* \* \* \* \*